(12) United States Patent
Kanazawa et al.

(10) Patent No.: US 8,193,356 B2
(45) Date of Patent: Jun. 5, 2012

(54) HETEROCYCLE COMPOUND, AND PRODUCTION PROCESS AND APPLICATION THEREOF

(75) Inventors: Hashime Kanazawa, Hamura (JP);
Tomoji Aotsuka, Hamura (JP);
Kentarou Kumazawa, Hamura (JP);
Kouki Ishitani, Hamura (JP); Takashi Nose, Hamura (JP)

(73) Assignee: Aska Pharmaceutical Co., Ltd., Tokyo (JP)

( * ) Notice: Subject to any disclaimer, the term of this patent is extended or adjusted under 35 U.S.C. 154(b) by 1089 days.

(21) Appl. No.: 11/991,858

(22) PCT Filed: Sep. 15, 2006

(86) PCT No.: PCT/JP2006/318348
§ 371 (c)(1),
(2), (4) Date: Mar. 12, 2008

(87) PCT Pub. No.: WO2007/032466
PCT Pub. Date: Mar. 22, 2007

(65) Prior Publication Data
US 2009/0131467 A1  May 21, 2009

(30) Foreign Application Priority Data
Sep. 15, 2005 (JP) .................................. 2005-268527

(51) Int. Cl.
*C07D 471/04* (2006.01)
*A61K 31/437* (2006.01)
*A61P 11/00* (2006.01)
*A61P 11/06* (2006.01)

(52) U.S. Cl. ........................................ 546/82; 514/293

(58) Field of Classification Search ........................ None
See application file for complete search history.

(56) References Cited

U.S. PATENT DOCUMENTS

| 5,817,670 A | 10/1998 | Takayama |
| 6,331,548 B1 | 12/2001 | Shimamoto et al. |
| 2003/0036651 A1 | 2/2003 | Aotsuka et al. |
| 2003/0100576 A1 | 5/2003 | Bonjouklian et al. |
| 2006/0040972 A1 | 2/2006 | Kanazawa et al. |

FOREIGN PATENT DOCUMENTS

| EP | 0 526 840 | 2/1993 |
| EP | 1 559 716 | 8/2005 |
| JP | 4-226985 | 8/1992 |
| JP | 3016905 | 8/1992 |
| JP | 5-132484 | 5/1993 |
| JP | 5-194515 | 8/1993 |
| JP | 6-100561 | 4/1994 |
| JP | 7-10875 | 1/1995 |
| JP | 10-226647 | 8/1998 |
| JP | 11-106385 | 4/1999 |
| JP | 2001-354655 | 12/2001 |
| JP | 2001-527508 | 12/2001 |
| JP | 2002-138089 | 5/2002 |
| JP | 2006-045118 | 2/2006 |
| WO | 96/06843 | 3/1996 |
| WO | 96/40636 | 12/1996 |
| WO | 99/02527 | 1/1999 |
| WO | 99/06404 | 2/1999 |
| WO | 99/38867 | 8/1999 |
| WO | 01/42244 | 6/2001 |
| WO | 2004/041819 | 5/2004 |

OTHER PUBLICATIONS

Crespo et al., Synthesis and Biological Evaluation of 2,5-Dihydropyrazolo[4,3-c]quinolin-3-ones, a Novel Series of PDE 4 Inhibitors with Low Emetic Potential and Antiasthmatic Properties, 10 Bioorg. & Med. Chem. Letts., 2661-2664 (2000).*
Richard B. Silverman, The Organic Chemistry of Drug Design and Drug Action: Chapter 2, Drug Discovery, Design, and Development, Academic Press, p. 4-51 (1992).*
Supplementary European Search Report dated Jun. 16, 2010 in EP Application No. EP 06 81 0190.
G. Hojas et al., "Heteroelectrocyclic reaction of 4-Azido-3-hydrazonoalkyl-quinolines to 2-arylaminopyrazolo[4,3-c]quinolones [1]", J. Heterocyclic Chem., vol. 37, pp. 1559-1569, Nov.-Dec. 2000.
W. Stadlbauer et al., "Ring Closure Reactions of 3-Arylhydrazonoalkyl-quinolin-2-ones to 1-Aryl-pyrazzolo[4,3-c]quinolin-2-ones", J. Heterocyclic Chem., vol. 41, pp. 681-390, 2004.
A. Sayed et al., "The Behavior of Some 3-Substituted 4-hydroxy-1-alkyl (or Phenyl) Carbostyrils Towards Amines and Hydrazines", Database Chemical Abstracts, Abstract No. 91:193222j, 1979.
International Search Report issued Nov. 28, 2006 in the International (PCT) Application of which the present application is the U.S. National Stage.
A. J. Dunplantier et al., "7-Oxo-4,5,6,7-tetrahydro-1H-pyrazolo[3,4-c]pyridines as Novel Inhibitors of Human Eosinophil Phosphodiesterase", J. Med. Chem., vol. 41, pp. 2268-2277, 1998.
M. S. Barnette, Phosphodiesterase 4 (PDE4) Inhibitors in Asthma and Chronic Obstructive Pulmonary Disease (COPD), Progress in Drug Research, vol. 53, pp. 193-229, 1999.

* cited by examiner

*Primary Examiner* — Janet Andres
*Assistant Examiner* — Timothy R Rozof
(74) *Attorney, Agent, or Firm* — Wenderoth, Lind & Ponack, L.L.P.

(57) ABSTRACT

The compound of the present invention is a novel compound which has a specific heterocycle skeleton, particularly a pyrazolonaphthyridine or pyrazoloquinoline skeleton having an organic group (e.g., a carbocycle and a heterocycle) bonding through an alkylene group at 3-position and a carbocycle bonding at 5-position and has a phosphodiesterase IV inhibitory activity. At least one of the ring (the carbocycle or the heterocycle) bonding at 3-position of the pyrazolonaphthyridine skeleton and the carbocycle bonding at 5-position may have a halogenated alkyl group and/or a halogenated alkoxy group as a substituent. Such a compound or a salt thereof is useful as a phosphodiesterase IV inhibitor and the like. According to the present invention, a novel compound having a high phosphodiesterase IV inhibitory effect can be provided.

8 Claims, No Drawings

HETEROCYCLE COMPOUND, AND PRODUCTION PROCESS AND APPLICATION THEREOF

TECHNICAL FIELD

This application is a U.S. national stage of International Application No. PCT/JP2006/318348 filed Sep. 15, 2006.

The present invention relates to a novel heterocycle compound having a phosphodiesterase IV inhibitory activity or a salt thereof, a production process thereof, and an application thereof (e.g., a pharmaceutical composition). Hereinafter, the term "phosphodiesterase" will be sometimes abbreviated PDE.

BACKGROUND ART

A phosphodiesterase (PDE) is an enzyme that hydrolyzes intracellular cyclic AMP (cAMP) and cyclic GMP (cGMP). As the PDE, eleven isozymes (types I to XI) have been known depending on the differences in characteristics thereof. It is known that, among these phosphodiesterases, phosphodiesterase (PDE) IV exists in large quantity in airway smooth muscle cells and inflammatory cells (e.g., neutrophils, eosinophils, and lymphocytes) and is an enzyme that selectively decomposes cAMP.

An increase of cAMP in airway smooth muscle cells ensures relaxation of the smooth muscle cells. On the other hand, an increase of cAMP in inflammatory cells ensures inhibition of release of cytotoxic proteins fromeosinophils and inhibition of activation of inflammatory cells. Therefore, if PDE IV that exists in large quantity in airway smooth muscle cells and inflammatory cells is inhibited by an inhibitor selectively inhibiting the isozyme, cAMP in these cells increases, so that expressions of a bronchodilator action due to airway smooth muscular relaxation and an anti-inflammatory action due to inhibition of inflammatory cell activation are expected. For example, as found in Barnette's review (see Non-patent Document 1), such a PDE IV inhibitor is expected as an excellent antasthmatic or an excellent therapeutic agent for chronic obstructive pulmonary disease (sometimes abbreviated COPD).

As the PDE IV inhibitor, theophylline that is a xanthine derivative, rolipram that is a catechol derivative, and others have been known. Theophylline inhibits PDE in various tissues due to isozyme non-selectivity thereof and causes not only an objective bronchodilator action but also unwanted actions on the heart, the central nervous system, or others. Rolipram has PDE IV selectivity, although rolipram tends to be transferred to the central nervous system due to an absorption characteristic thereof and has a shortcoming of causing central side effect(s) such as an emetic action. Further, a large number of pharmaceutical companies have focused attention on the inhibition of PDE IV for an asthma therapy or treatment over the past ten years, and biological studies of PDE IV isozyme and relationships between the structure and the activity of the PDE IV inhibitor have reviewed in some documents. In the process, it has been pointed out that the clinical utility of a selective PDE IV inhibitor such as rolipram that is a typical active substance is usually decreased by nausea and emesis which restrict clinical applications of the inhibitor (see Non-patent Document 2). Further, in these years, it has been understood that a PDE IV inhibitor inhibits drug metabolizing enzyme(s) such as CYP2D6 or CYP3A4 and express various side effects. Therefore, a development of a PDE IV inhibitor that has no effect on drug metabolizing enzyme(s) has been expected.

From such a situation, for developing an agent which keeps undesired side effects in tissues and organs other than bronchiolar smooth muscle and inflammatory cells to a minimum and is excellent in an antasthmatic effect and a COPD-preventing and/or-therapeutic effect, the development of various PDE IV inhibitors has been tried.

For example, with the aim of an inhibitor having a higher PDE IV selectivity, an aphthalene derivative (e.g., see Patent Document 1), a catechol diether derivative (e.g., see Patent Document 2), a 2,3-di-substituted pyridine derivative (e.g., see Patent Document 3), and others have been proposed. Further, for the development of not only an antasthmatic but also a preventive and/or therapeutic agent for a wider range of diseases, a compound having a naphthyridine skeleton and showing a PDE IV inhibitory action has been proposed (e.g., see Patent Document 4, Patent Document 5, Patent Document 6, Patent Document 7, Patent Document 8, Patent Document 9, and Patent Document 10).

On the other hand, as a compound having a fused ring in which naphthyridine and a heterocycle are fused together, a compound having an anti-inflammatory action, an immunomodulator action, an analgesic action, and an antipyretic action (e.g., see Patent Document 11 and Patent Document 12) and a compound having an anti-inflammatory action, an immunomodulator action, a bronchodilator action, and a pilatory action (e.g., see Patent Document 13 and Patent Document 14) are disclosed. However, none of these documents discloses a PDE IV inhibitory action.

International Publication No. 04/041819 pamphlet (Patent Document 15) discloses, as a compound having a high PDE IV inhibitory activity, a pyrazolonaphthyridine derivative having a phenyl-alkyl group, which may have a substituent, at 3-position of pyrazolonaphthyridine and phenyl group, which may have a substituent, at 5-position thereof. The compound described in this document has a high PDE IV inhibitory activity and a high safety, however, further useful active compounds have been required.

Moreover, Japanese Patent Application Laid-Open No. 45118/2006 (JP-2006-45118A, Patent Document 16) discloses a pyrazoloquinolone derivative having a $C_{1-6}$aliphatic hydrocarbon group on a nitrogen atom constituting a quinolone ring thereof. However, the Patent Document 16 does not mention a compound having a cyclic hydrocarbon group on the nitrogen atom.

[Patent Document 1] Japanese Patent Application Laid-Open No. 226647/1998 (JP-10-226647A)
[Patent Document 2] Japanese Patent Application Laid-Open No. 527508/2001 (JP-2001-527508A)
[Patent Document 3] Japanese Patent Application Laid-Open No. 354655/2001 (JP-2001-354655A)
[Patent Document 4] Japanese Patent Application Laid-Open No. 10875/1995 (JP-7-10875A)
[Patent Document 5] International Publication No. 96/06843 pamphlet
[Patent Document 6] Japanese Patent Application Laid-Open No. 106385/1999 (JP-11-106385A)
[Patent Document 7] Japanese Patent Application Laid-Open No. 138089/2002 (JP-2002-138089A)
[Patent Document 8] International Publication No. 99/02527 pamphlet
[Patent Document 9] International Publication No. 99/38867 pamphlet
[Patent Document 10] International Publication No. 01/42244 pamphlet
[Patent Document 11] Japanese Patent Application Laid-Open No. 132484/1993 (JP-5-132484A)
[Patent Document 12] Japanese Patent Application Laid-Open No. 100561/1994 (JP-6-100561A)
[Patent Document 13] Japanese Patent Application Laid-Open No. 194515/1993 (JP-5-194515A)
[Patent Document 14] Japanese Patent No. 3016905B
[Patent Document 15] International Publication No. 04/041819 pamphlet

[Patent Document 16] Japanese Patent Application Laid-Open No. 45118/2006 (JP-2006-45118A) (claim 1)
[Non-patent Document 1] "PROGRESS IN DRUG RESEARCH", (United States), 53, 1999, p193-2277
[Non-patent Document 2] "JOURNAL OF MEDICINAL CHEMISTRY", (United States), 41, 1998, p2268-2277

DISCLOSURE OF THE INVENTION

Problems to be Solved by the Invention

It is therefore an object of the present invention to provide a novel heterocycle compound having a high phosphodiesterase IV inhibitory activity or a salt thereof, a production process thereof, and an application thereof.

It is another object of the present invention to provide a novel heterocycle compound which effectively acts on bronchiolar smooth muscle and inflammatory cells and has an extremely high phosphodiesterase IV inhibitory activity or a salt thereof, a production process thereof, and an application thereof.

It is still another object of the present invention to provide a novel heterocycle compound having a high safety and being useful for an antasthmatic and a preventing and/or therapeutic agent for chronic obstructive pulmonary disease (COPD) or a salt thereof, a production process thereof, and an application thereof.

Means to Solve the Problems

The inventors of the present invention made intensive studies to achieve the above objects and finally found that a specific heterocycle compound shows a high phosphodiesterase IV inhibitory effect, particularly, that introduction of a specific substituent into a pyrazolonaphthyridine derivative (for example, introduction of a halogenated alkyl group or a halogenated alkoxy group into at least one of an aryl group constituting an arylalkyl group bonding at 3-position of the pyrazolonaphthyridine derivative and an aryl group of 5-position of the derivative) remarkably increases a phosphodiesterase IV inhibitory activity. The present invention was accomplished based on the above findings.

That is, the heterocycle compound (or heterocyclic compound) of the present invention is represented by the following formula (1):

[Formula 1]

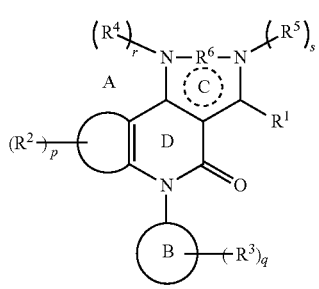

(1)

wherein the ring A represents a heterocycle (or a heterocyclic ring) containing a nitrogen atom as a heteroatom or a carbocycle (or a carbocyclic ring);
the ring B represents a carbocycle;
—$R^6$— represents a direct bond (or a single bond), an aliphatic divalent group which may have a substituent (e.g., an alkylene group, an alkenylene group, and an alkynylene group), an alicyclic divalent group which may have a substituent, an aromatic divalent group which may have a substituent, or a trivalent group represented by the following formula (r6-1) or (r6-2):

[Formula 2]

wherein $R^6$ represents a hydrogen atom, an alkyl group, an alkenyl group, an alkynyl group, or an aryl group;
the ring C is an aromatic or nonaromatic ring and represents a heterocycle represented by the following formula (1c-1) or (1c-2):

[Formula 3]

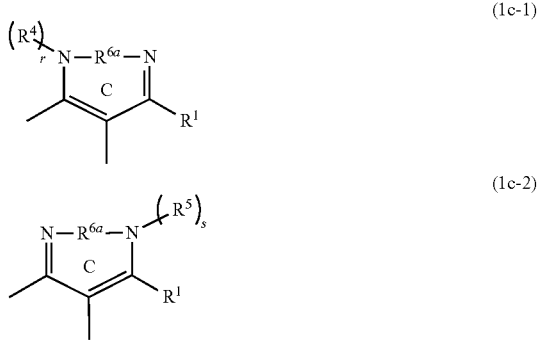

wherein $R^4$ and $R^5$ are the same or different and each represents a hydrogen atom, an alkyl group, an aryl group, an aralkyl group, or an acyl group;
each of —$R^{6a}$— and —$R^{6b}$— corresponds to the —$R^6$—,
the —$R^{6a}$— represents a direct bond (or a single bond), an aliphatic divalent group which may have a substituent, an alicyclic divalent group which may have a substituent, an aromatic divalent group which may have a substituent, or a trivalent group represented by the formula (r6-1), and
the —$R^{6b}$— represents a direct bond (or a single bond), an aliphatic divalent group which may have a substituent, an alicyclic divalent group which may have a substituent, an aromatic divalent group which may have a substituent, or a trivalent group represented by the formula (r6-2);
r denotes 0 or 1 depending on the species of the —$R^6$— and the —$R^{6a}$—, and s denotes 0 or 1 depending on the species of the —$R^6$— and the —$R^{6b}$—;
when the —$R^6$— and the —$R^{6a}$— are the direct bond or the divalent group, r is 1, or
when the —$R^6$— and the —$R^{6a}$— are the trivalent group (r6-1), r is 0; and
when the —$R^6$— and the —$R^{6b}$— are the direct bond or the divalent group, s is 1, or
when the —$R^6$— and the —$R^{6b}$— are the trivalent group (r6-2), s is 0;

the ring D represents a nitrogen atom-containing unsaturated 6-membered ring having an oxo group at 2-position;

$R^1$ represents an alkyl group or an alkyl group having a substituent, and the substituent of the alkyl group represents a hydroxyl group, a halogen atom, a nitro group, an amino group, an N-substituted amino group, an alkoxy group which may have a substituent, or a group represented by the following formula (1e):

[Formula 4]

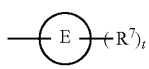

(1e)

wherein the ring E represents a heterocycle containing at least one heteroatom selected from the group consisting of a nitrogen atom, an oxygen atom, and a sulfur atom, or a carbocycle;

$R^7$ represents a substituent selected from the group consisting of a halogen atom, a hydroxyl group, a cyano group, a nitro group, an alkyl group which may have a substituent, an alkoxy group which may have a substituent, a carboxyl group, an alkoxycarbonyl group which may have a substituent, an acyl group which may have a substituent, an acyloxy group which may have a substituent, a carboxyalkyl group, an alkoxycarbonylalkyl group which may have a substituent, an amino group, an N-substituted amino group, a ureido group, a sulfonic acid group, a sulfinic acid group, an alkylsulfonyl group which may have a substituent, and a sulfonamide group, and the species of a plurality of $R^7$s may be the same or different; and the number t denotes an integer of 0 to 5;

$R^2$ represents a halogen atom, an alkyl group which may have a substituent, a hydroxyl group, an alkoxy group which may have a substituent, or an alkylthio group, and the species of a plurality of $R^2$s may be the same or different;

$R^3$ represents a substituent selected from the group consisting of a halogen atom, a hydroxyl group, a cyano group, a nitro group, an alkyl group which may have a substituent, an alkoxy group which may have a substituent, a carboxyl group, an alkoxycarbonyl group which may have a substituent, an acyl group which may have a substituent, an acyloxy group which may have a substituent, a carboxyalkyl group, an alkoxycarbonylalkyl group which may have a substituent, an amino group, an N-substituted amino group, a ureido group, a sulfonic acid group, a sulfinic acid group, an alkylsulfonyl group which may have a substituent, and a sulfonamide group, and the species of a plurality of $R^3$s may be the same or different;

p and q are the same or different and each denotes an integer of 0 to 5;

when the group $R^1$ is a straight chain $C_{1-3}$alkyl group having a benzene ring, a thiophene ring, or a pyridine ring as the ring E, the ring B is a benzene ring, the number p is 0, the —$R^6$— is a direct bond (or a single bond), and a fused ring comprising the ring A and the ring D is a fused ring represented by the following formula:

[Formula 5]

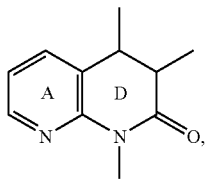

at least one of the ring B and the ring E has at least one member selected from the group consisting of a halogen-containing alkyl group and a halogen-containing alkoxy group as the substituent $R^3$ and/or $R^7$;

when the group $R^1$ is an alkyl group having no substituent, the ring B has at least one member selected from the group consisting of a halogen-containing alkyl group and a halogen-containing alkoxy group as the substituent $R^3$; and $R^4$, $R^5$, —$R^6$—, r, s, and t have the same meanings as defined above.

In the above-mentioned formula (1), the group $R^1$ may be an alkyl group (e.g., a $C_{1-6}$alkyl group), a nitroalkyl group, an aminoalkyl group, an N-substituted aminoalkyl group, a halogen-containing alkyl group (e.g., a halogen-containing $C_{1-6}$alkyl group), an alkoxyalkyl group (e.g., a $C_{1-6}$alkoxy-$C_{1-6}$alkyl group), an alkyl group having a halogen-containing alkoxy group (e.g., a halogen-containing $C_{1-6}$alkoxy-$C_{1-6}$ alkyl group), or an alkyl group having a group represented by the formula (1e) (e.g., a $C_{1-6}$alkyl group). Incidentally, in the above-mentioned formula (1e), the ring E may be a cycloalkane ring or an arene ring, the group $R^7$ may be a substituent selected from the group consisting of a halogen atom, an alkyl group (e.g., a $C_{1-6}$alkyl group), a halogen-containing alkyl group (e.g., a halogen-containing $C_{1-6}$alkyl group), an alkoxy group (e.g., a $C_{1-6}$alkoxy group), and a halogen-containing alkoxy group (e.g., a halogen-containing $C_{1-6}$alkoxy group), and the number t may be an integer of 0 to 4 (preferably an integer of 0 to 3).

At least one of the ring B and the ring E may have at least one member selected from the group consisting of a fluoroalkyl group (e.g., a straight chain or branched chain fluoro $C_{1-6}$alkyl group) and a fluoroalkoxy group (e.g., a straight chain or branched chain fluoro $C_{1-6}$alkoxy group) as the substituent $R^3$ and/or $R^7$.

The compound of the above-mentioned formula (1) also includes a compound in which the ring A is an aromatic 6-membered heterocycle having a nitrogen atom as a heteroatom or a $C_{6-10}$arene ring;

the ring B is a $C_{6-10}$arene ring;

the group $R^1$ is a group represented by the following formula:

[Formula 6]

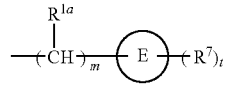

wherein $R^{1a}$ is a hydrogen atom or a $C_{1-3}$alkyl group, and the species of a plurality of $R^{1a}$ may be the same or different, m denotes an integer of 1 to 10, the ring E is a $C_{6-10}$arene ring, $R^7$ is a substituent selected from the group consisting of a halogen atom, a straight chain or branched chain $C_{1-6}$alkyl group, a straight chain or branched chain fluoro$C_{1-6}$alkyl group, a straight chain or branched chain $C_{1-6}$alkoxy group, and a straight chain or branched chain fluoro$C_{1-6}$alkoxy group, and the number t has the same meaning as defined above;

the group $R^3$ is a substituent selected from the group consisting of a halogen atom, a straight chain or branched chain $C_{1-6}$alkyl group, a straight chain or branched chain fluoro$C_{1-6}$alkyl group, a straight chain or branched chain $C_{1-6}$alkoxy group, and a straight chain or branched chain fluoro$C_{1-6}$alkoxy group;

the groups $R^4$ and $R^5$ are the same or different and each represents a hydrogen atom or a straight chain or branched chain $C_{1-6}$alkyl group;

the —R⁶— represents a direct bond (or a single bond), a straight chain or branched chain $C_{1-6}$alkylene group which may have a substituent, a straight chain or branched chain $C_{2-6}$alkenylene group which may have a substituent, a $C_{6-10}$arylene group which may have a substituent, or a trivalent group represented by the formula (r6-1) or (r6-2), and in these trivalent groups (r6-1) and (r6-2), the group $R^{6c}$ represents a hydrogen atom, a $C_{1-6}$alkyl group, or a $C_{6-10}$aryl group; and the number p denotes an integer of 0 to 4.

Moreover, in the above-mentioned formula (1), the ring A may be a pyridine ring or a benzene ring;

the ring B may be a benzene ring;

the group $R^1$ may be a straight chain or branched chain $C_{1-4}$alkyl group having a group represented by the formula (1e), and in the formula, (1e), the ring E may be a benzene ring, the group $R^7$ may be a substituent selected from the group consisting of a halogen atom, a $C_{1-4}$alkyl group, a fluoro$C_{1-4}$alkyl group, a $C_{1-4}$alkoxy group, and a fluoro$C_{1-4}$alkoxy group;

the group $R^3$ may be a substituent selected from the group consisting of a halogen atom, a $C_{1-4}$alkyl group, a fluoro$C_{1-4}$alkyl group, a $C_{1-4}$alkoxy group, and a fluoro$C_{1-4}$alkoxy group;

the groups $R^4$ and $R^5$ may be the same or different and each represents a hydrogen atom or a $C_{1-4}$alkyl group;

the —R⁶— may represent a direct bond (or a single bond), a straight chain or branched chain $C_{1-4}$alkylene group which may have a substituent, a straight chain or branched chain $C_{2-4}$alkenylene group which may have a substituent, a phenylene group which may have a substituent, or a trivalent group represented by the formula (r6-1) or (r6-2), and in these trivalent groups (r6-1) and (r6-2), the group $R^{6c}$ may represent a hydrogen atom, a $C_{1-4}$alkyl group, or a phenyl group;

the number p may be 0; and at least one of the ring B and the ring E may have at least one member selected from the group consisting of a fluoro $C_{1-6}$alkyl group and a fluoro$C_{1-6}$alkoxy group as the substituent $R^3$ and/or $R^7$.

In the above-mentioned formula (1), the ring C may be a 5- to 7-membered heterocycle represented by the following formulae (1c-3) to (1c-7):

[Formula 7]

(1c-3)

(1c-4)

(1c-5)

(1c-6)

(1c-7)

wherein $R^{6d}$ and $R^{6e}$ are the same or different and each represents a hydrogen atom, a halogen atom, an alkyl group, an aryl group, an aralkyl group, an alkoxy group, an acyl group, an amino group, or an N-substituted amino group, the groups $R^{6d}$ and $R^{6e}$ may bond together to form an aromatic or nonaromatic ring, the aromatic or nonaromatic ring may have at least one substituent selected from the group consisting of a halogen atom, a hydroxyl group, a cyano group, a nitro group, an alkyl group which may have a substituent, an alkoxy group which may have a substituent, a carboxyl group, an alkoxycarbonyl group which may have a substituent, an acyl group which may have a substituent, an acyloxy group which may have a substituent, a carboxyalkyl group, an alkoxycarbonylalkyl group which may have a substituent, an amino group, an N-substituted amino group, a ureido group, a sulfonic acid group, a sulfinic acid group, an alkylsulfonyl group which may have a substituent, and a sulfonamide group; and the groups $R^1$, $R^4$, $R^5$ and $R^{6c}$ have the same meanings as defined above.

Moreover, in the above-mentioned formula (1), the ring A may be any one of the rings represented by the following formulae.

[Formula 8]

Representative compounds represented by the above-mentioned formula (1) include, for example, a 3-($C_{1-4}$alkoxy-$C_{1-3}$alkyl)-5-phenyl-1H-pyrazolo[4,3-c][1,8]-naphthyridin-4(5H)-one, a 3-($C_{1-4}$alkoxy-$C_{1-3}$alkyl)-5-(fluoro$C_{1-4}$alkyl-phenyl)-1H-pyrazolo[4,3-c][1,8]-naphthyridin-4(5H)-one, a 3-($C_{1-4}$alkoxy-$C_{1-3}$alkyl)-5-(fluoro$C_{1-4}$alkoxy-phenyl)-1H-pyrazolo[4,3-c][1,8]-naphthyridin-4(5H)-one, a 3-($C_{4-10}$cycloalkyl-$C_{1-3}$alkyl)-5-phenyl-1H-pyrazolo[4,3-c][1,8]-naphthyridin-4(5H)-one, a 3-($C_{4-10}$cycloalkyl-$C_{1-3}$alkyl)-5-

(fluoroC$_{1-4}$alkyl-phenyl)-1H-pyrazolo[4,3-c][1,8]-naphthyridin-4(5H)-one, a 3-(C$_{4-10}$cycloalkyl-C$_{1-3}$alkyl)-5-(fluoroC$_{1-4}$alkoxy-phenyl)-1H-pyrazolo[4,3-c][1,8]-naphthyridin-4(5H)-one, a 3-(fluoroC$_{1-10}$alkyl)-5-phenyl-1H-pyrazolo[4,3-c][1,8]-naphthyridin-4(5H)-one, a 3-(fluoroC$_{1-10}$alkyl)-5-(fluoroC$_{1-4}$alkyl-phenyl)-1H-pyrazolo[4,3-c][1,8]-naphthyridin-4(5H)-one, a 3-(fluoroC$_{1-10}$alkyl)-5-(fluoroC$_{1-4}$alkoxy-phenyl)-1H-pyrazolo[4,3-c][1,8]-naphthyridin-4(5H)-one, a 3-(phenyl-C$_{1-6}$alkyl)-5-phenyl-1H-pyrazolo[4,3-c][1,8]-naphthyridin-4(5H)-one, a 3-(phenyl-C$_{1-3}$alkyl)-5-(fluoroC$_{1-4}$alkyl-phenyl)-1H-pyrazolo[4,3-c][1,8]-naphthyridin-4(5H)-one, a 3-(phenyl-C$_{1-3}$alkyl)-5-(fluoroC$_{1-4}$alkoxy-phenyl)-1H-pyrazolo[4,3-c][1,8]-naphthyridin-4(5H)-one, a 3-(phenyl-branched C$_{2-4}$alkyl)-5-phenyl-1H-pyrazolo[4,3-c][1,8]-naphthyridin-4(5H)-one, a 3-(phenyl-branched C$_{2-4}$alkyl)-5-(fluoroC$_{1-4}$alkyl-phenyl)-1H-pyrazolo[4,3-c][1,8]-naphthyridin-4(5H)-one, a 3-(phenyl-branched C$_{2-4}$alkyl)-5-(fluoroC$_{1-4}$alkoxy-phenyl)-1H-pyrazolo[4,3-c][1,8]-naphthyridin-4(5H)-one, a 3-(phenyl-C$_{1-3}$alkyl)-5-phenyl-1H-pyrazolo[4,3-c][1,7]-naphthyridin-4(5H)-one, a 3-(phenyl-C$_{1-3}$alkyl)-5-phenyl-1H-pyrazolo[4,3-c][1,6]-naphthyridin-4(5H)-one, a 3-(phenyl-C$_{1-3}$alkyl)-5-phenyl-1H-pyrazolo[4,3-c][1,5]-naphthyridin-4(5H)-one, a 3-(phenyl-C$_{1-3}$alkyl)-5-phenyl-1H-pyrazolo[4,3-c]quinolin-4(5H)-one, a 3-[(fluoroC$_{1-4}$alkyl-phenyl)C$_{1-3}$alkyl]-5-phenyl-1H-pyrazolo[4,3-c][1,8]-naphthyridin-4(5H)-one, a 3-[(fluoroC$_{1-4}$alkyl-phenyl)C$_{1-3}$alkyl]-5-(fluoroC$_{1-4}$alkyl-phenyl)-1H-pyrazolo[4,3-c][1,8]-naphthyridin-4(5H)-one, a 3-[(fluoroC$_{1-4}$alkyl-phenyl)C$_{1-3}$alkyl]-5-(fluoroC$_{1-4}$alkoxy-phenyl)-1H-pyrazolo[4,3-c][1,8]-naphthyridin-4(5H)-one, a 3-[(fluoroC$_{1-4}$alkyl-phenyl) branched C$_{2-4}$alkyl]-5-phenyl-1H-pyrazolo[4,3-c][1,8]-naphthyridin-4(5H)-one, a 3-[(fluoroC$_{1-4}$alkyl-phenyl) branched C$_{2-4}$alkyl]-5-(fluoroC$_{1-4}$alkyl-phenyl)-1H-pyrazolo[4,3-c][1,8]-naphthyridin-4(5H)-one, a 3-[(fluoroC$_{1-4}$alkyl-phenyl) branched C$_{2-4}$alkyl]-5-(fluoroC$_{1-4}$alkoxy-phenyl)-1H-pyrazolo[4,3-c][1,8]-naphthyridin-4(5H)-one, a 3-[(fluoroC$_{1-4}$alkoxy-phenyl)C$_{1-3}$alkyl]-5-phenyl-1H-pyrazolo[4,3-c][1,8]-naphthyridin-4(5H)-one, a 3-[(fluoroC$_{1-4}$alkoxy-phenyl)C$_{1-3}$alkyl]-5-(fluoroC$_{1-4}$alkyl-phenyl)-1H-pyrazolo[4,3-c][1,8]-naphthyridin-4(5H)-one, a 3-[(fluoroC$_{1-4}$alkoxy-phenyl)C$_{1-3}$alkyl]-5-(fluoroC$_{1-4}$alkoxy-phenyl)-1H-pyrazolo[4,3-c][1,8]-naphthyridin-4(5H)-one, a 3-[(fluoroC$_{1-4}$alkoxy-phenyl) branched C$_{2-4}$alkyl]-5-phenyl-1H-pyrazolo[4,3-c][1,8]-naphthyridin-4(5H)-one, a 3-[(fluoroC$_{1-4}$alkoxy-phenyl) branched C$_{2-4}$alkyl]-5-(fluoroC$_{1-4}$alkyl-phenyl)-1H-pyrazolo[4,3-c][1,8]-naphthyridin-4(5H)-one, a 3-[(fluoroC$_{1-4}$alkoxy-phenyl) branched C$_{2-4}$alkyl]-5-(fluoroC$_{1-4}$alkoxy-phenyl)-1H-pyrazolo[4,3-c][1,8]-naphthyridin-4(5H)-one, a 3-(C$_{1-4}$alkyl-phenyl-C$_{1-3}$alkyl)-5-(fluoroC$_{1-4}$alkyl-phenyl)-1H-pyrazolo[4,3-c][1,8]-naphthyridin-4(5H)-one, a 3-(C$_{1-4}$alkyl-phenyl-C$_{1-3}$alkyl)-5-(fluoroC$_{1-4}$alkoxy-phenyl)-1H-pyrazolo[4,3-c][1,8]-naphthyridin-4(5H)-one, a 3-(nitrophenyl-C$_{1-3}$alkyl)-5-(fluoroC$_{1-4}$alkyl-phenyl)-1H-pyrazolo[4,3-c][1,8]-naphthyridin-4(5H)-one, a 3-(nitrophenyl-C$_{1-3}$alkyl)-5-(fluoroC$_{1-4}$alkoxy-phenyl)-1H-pyrazolo[4,3-c][1,8]-naphthyridin-4(5H)-one, a 3-(C$_{1-4}$alkoxy-phenyl-C$_{1-3}$alkyl)-5-(fluoroC$_{1-4}$alkyl-phenyl)-1H-pyrazolo[4,3-c][1,8]-naphthyridin-4(5H)-one, a 3-(C$_{1-4}$alkoxy-phenyl-C$_{1-3}$alkyl)-5-(fluoroC$_{1-4}$alkoxy-phenyl)-1H-pyrazolo[4,3-c][1,8]-naphthyridin-4(5H)-one, a 3-(halophenyl-C$_{1-3}$alkyl)-5-(fluoroC$_{1-4}$alkyl-phenyl)-1H-pyrazolo[4,3-c][1,8]-naphthyridin-4(5H)-one, a 3-(halophenyl-C$_{1-3}$alkyl)-5-(fluoroC$_{1-4}$alkoxy-phenyl)-1H-pyrazolo[4,3-c][1,8]-naphthyridin-4(5H)-one, a 5-phenyl-3-(tetrahydro-2H-pyran-4-ylC$_{1-3}$alkyl)-1H-pyrazolo[4,3-c][1,8]naphthyridin-4(5H)-one which may have a fluoroC$_{1-4}$alkyl group or a fluoroC$_{1-4}$alkoxy group at the phenyl group of 5-position, a 3-(thienylC$_{1-3}$alkyl)-5-(fluoroC$_{1-4}$alkyl-phenyl)-1H-pyrazolo[4,3-c][1,8]-naphthyridin-4(5H)-one, and 3-(thienylC$_{1-3}$alkyl)-5-(fluoroC$_{1-4}$alkoxy-phenyl)-1H-pyrazolo[4,3-c][1,8]-naphthyridin-4(5H)-one.

The present invention also includes a salt of a compound represented by the above-mentioned formula (1) (a physiologically or pharmaceutically acceptable salt).

The compound (1) or a salt thereof may be produced by, for example, allowing a compound represented by the following formula (3) to react with a compound represented by the following formula (4), a hydrate thereof, or a salt thereof:

[Formula 1]

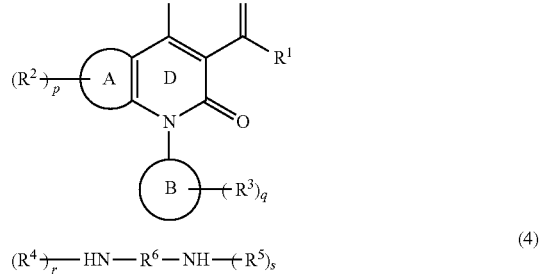

wherein the ring A, the ring B, the ring D, R$^1$, R$^2$, R$^3$, R$^4$, R$^5$, —R$^6$—, p, q, r and s have the same meanings as defined above, provided that the compound represented by the formula (4) is a compound represented by the following formula (4a) or (4b):

[Formula 10]

wherein R$^4$, R$^5$, R$^{6a}$— —R$^{6b}$—, r, and s have the same meanings as defined above.

The present invention includes a pharmaceutical (or medical) composition containing the compound (1) or a salt thereof and a phosphodiesterase IV inhibitor comprising the compound (1) or a salt thereof. Further, the present invention includes an agent (or a preparation) for preventing and/or treating a disease in which phosphodiesterase IV directly or indirectly participates (that is, a preventive and/or therapeutic agent), which comprises the compound (1) or a salt thereof and an agent (or a preparation) for preventing and/or treating a respiratory disease (that is, a preventive and/or therapeutic agent), which comprises the compound (1) or a salt thereof. The respiratory disease may be a bronchial asthma including chronic bronchial asthma and atopic asthma, acute bronchitis, chronic bronchitis, asthmatic bronchitis, pneumonic disease, pulmonary emphysema, chronic obstructive pulmonary disease (COPD), acute respiratory distress syndrome (ARDS), and others. The compound (1) or the salt thereof of the present invention is useful as a component of an antasthmatic. Incidentally, the present invention further includes a method for treating (or curing) the above-mentioned various diseases by using the compound (1) or a salt thereof.

Effects of the Invention

The heterocycle compound or the salt thereof of the present invention has a higher phosphodiesterase IV inhibitory activity. In particular, the compound or the salt thereof effectively acts on bronchiolar smooth muscle and inflammatory cells and have an extremely high phosphodiesterase IV inhibitory activity. In addition, the compound or the salt thereof has few side effects and high safety. Therefore, the compound or the salt thereof is useful as an antasthmatic and a preventive and/or therapeutic agent for COPD.

DETAILED DESCRIPTION OF THE INVENTION

Heterocycle Compound or Salt Thereof

In the heterocycle compound represented by the above-mentioned formula (1), the ring A is a heterocycle containing a nitrogen atom as a heteroatom or a carbocycle. The ring A is usually an aromatic ring in practical cases. Moreover, the heterocycle is not limited to a heterocycle having one nitrogen atom and may be a heterocycle having a plurality of nitrogen atoms. Further, the heterocycle may be a 4- to 10-membered ring and is usually a 6-membered ring in practical cases.

Such a heterocycle may include a nitrogen atom-containing 6-membered ring such as a pyridine ring, a pyrazine ring, a pyrimidine ring, or a pyridazine ring, and others. These heterocycles may be a fused (or condensed) heterocycle in which heterocycle(s) and benzene ring(s) are fused (or condensed) together. The heterocycle is often an aromatic 6-membered heterocycle such as a pyridine ring.

The carbocycle may include an aromatic carbocycle, for example, an arene ring such as a benzene ring or a naphthalene ring (e.g., a $C_{6-14}$arene ring). The carbocycle is usually a $C_{6-10}$arene ring, particularly a benzene ring, in practical cases.

As the ring A, for example, rings represented by the following formulae are preferred.

[Formula 11]

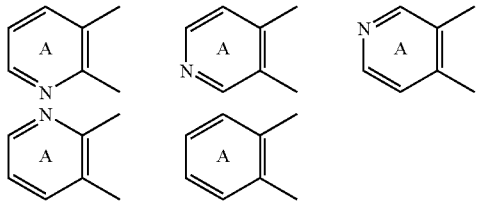

The substituent $R^2$ of the ring A may include a halogen atom (e.g., fluorine, chlorine, bromine, or iodine atom), an alkyl group which may have a substituent, a hydroxyl group, an alkoxy group which may have a substituent, or an alkylthio group (e.g., a straight chain or branched chain $C_{1-6}$alkylthio group such as methylthio group or ethylthio group), and others.

The alkyl group represented by $R^2$ may include a straight chain or branched chain $C_{1-10}$alkyl group such as methyl group, ethyl group, propyl group, isopropyl group, butyl group, isobutyl group, s-butyl group, t-butyl group, pentyl group, isopentyl group, hexyl group, or isohexyl group, and others. The alkyl group may be a $C_{1-6}$alkyl group (preferably a $C_{1-4}$alkyl group, and more preferably a $C_{1-3}$alkyl group). These alkyl groups may have a substituent. The substituent of the alkyl group may include a halogen atom (e.g., chlorine, bromine, or fluorine atom etc.), an alkoxy group (a straight chain or branched chain $C_{1-4}$alkoxy group such as methoxy group), and others. The preferred substituent includes a halogen atom (particularly chlorine atom and/or fluorine atom).

The alkoxy group represented by $R^2$ may include, for example, a straight chain or branched chain $C_{1-10}$alkoxy group such as methoxy group, ethoxy group, propoxy group, isopropoxy group, butoxy group, s-butoxy group, t-butoxy group, pentyloxy group, isopentyloxy group, hexyloxy group, isohexyloxy group, heptyloxy group, or octyloxy group. The preferred alkoxy group includes a $C_{1-6}$alkoxy group (e.g., a $C_{1-4}$alkoxy group), and more preferably a $C_{1-3}$alkoxy group (e.g., a $C_{1-2}$alkoxy group). The alkoxy group may have a substituent. The substituent of the alkoxy group may include a halogen atom (e.g., chlorine, bromine, or fluorine atom etc.), an alkoxy group (a straight chain or branched chain $C_{1-4}$alkoxy group such as methoxy group), and others. The preferred substituent includes a halogen atom (particularly chlorine atom and/or fluorine atom).

Among these substituents $R^2$, the particularly preferred one includes an alkyl group (e.g., a straight chain or branched chain $C_{1-6}$alkyl group), a halogen-containing alkyl group (e.g., a straight chain or branched chain $C_{1-6}$alkyl group containing a halogen), a hydroxyl group, an alkoxy group (e.g., a straight chain or branched chain $C_{1-6}$alkoxy group), a halogen-containing alkoxy group (e.g., a straight chain or branched chain $C_{1-6}$alkoxy group containing a halogen), and others.

The number p of the substituents $R^2$ is an integer of 0 to 5, preferably an integer of 0 to 4 (e.g., an integer of 0 to 3), more preferably an integer of 0 to 2, and particularly 0 or 1. The ring A having no substituent $R^2$ (that is, p=0) is also preferred. Incidentally, when the number p is not less than 2, the species of the substituents $R^2$ may be different or the same.

The carbocycle represented by the ring B may be a cycloalkane ring (e.g., a $C_{3-10}$cycloalkane ring such as a cyclobutane ring, a cyclopentane ring, a cyclohexane ring, a cycloheptane ring, or a cyclooctane ring) or an arene ring (e.g., a $C_{6-14}$arene ring such as a benzene ring or a naphthalene ring). The carbocycle is usually an aromatic carbocycle (e.g., an arene ring), for example, a $C_{6-10}$arene ring, particularly a benzene ring, in practical cases.

The substituent $R^3$ of the ring B may include a halogen atom (the halogen atom exemplified in the paragraph of the above-mentioned $R^2$), a hydroxyl group, a cyano group, a nitro group, an alkyl group which may have a substituent (e.g., the alkyl group which may have a substituent, exemplified in the paragraph of the above-mentioned $R^2$), an alkoxy group which may have a substituent (e.g., the alkoxy group which may have a substituent, exemplified in the paragraph of the above-mentioned $R^2$), a carboxyl group, an alkoxycarbonyl group which may have a substituent (for example, the alkoxycarbonyl group which may have a substituent, exemplified in the paragraph of the above-mentioned $R^2$, e.g., a straight chain or branched chain $C_{1-10}$alkoxy-carbonyl group such as methoxycarbonyl group, ethoxycarbonyl group, propoxycarbonyl group, butoxycarbonyl group, t-butoxycarbonyl group, pentyloxycarbonyl, or hexyloxycarbonyl group), an acyl group which may have a substituent (for example, the acyl group which may have a substituent, exemplified in the paragraph of the above-mentioned $R^2$, e.g., a straight chain or branched chain $C_{1-10}$acyl group such as formyl group, acetyl group, propionyl group, butyryl group, isobutyryl group, or valeryl group), an acyloxy group (e.g., a $C_{1-10}$acyloxy group corresponding to the above-mentioned acyl group, such as acetoxy group), a carboxyalkyl group (e.g., a carboxyalkyl group corresponding to the above-mentioned alkyl group), an alkoxycarbonylalkyl group which may have a substituent (for example, the alkoxycarbonylalkyl group which may have a substituent, exemplified in the paragraph of the above-mentioned $R^2$, e.g., an alkyl group corresponding to the above-mentioned alkyl group and having a $C_{1-6}$alkoxy-carbonyl group such as methoxycarbonyl group or ethoxycarbonyl group), an amino group, an N-substituted amino group (e.g., a straight chain or branched chain $C_{1-6}$alkylamino group such as methylamino group or dimethylamino group; a $C_{1-6}$acylamino group such as acetylamino group; and a straight chain or branched chain $C_{1-6}$alkylsulfonylamino group such as methylsulfonylamino group or ethylsulfonylamino group), a ureido group, a sulfonic acid group ($-SO_3H$), a sulfinic acid group ($-SO_2H$), an alkylsulfonyl group which may have a substituent (for example, the alkylsulfonyl group which may have a substituent, exemplified in the paragraph of the above-mentioned $R^2$, e.g., a straight chain or branched chain $C_{1-6}$alkylsulfonyl group such as methylsulfonyl group or ethylsulfonyl group), a sulfonamide group, and others. Incidentally, the number q of the substituents $R^3$ may be selected from the same range as that of the number p of the substituents $R^2$.

Among these substituents, the preferred one includes a halogen atom, an alkyl group (e.g., a straight chain or branched chain $C_{1-6}$alkyl group), a halogen-containing alkyl group (e.g., a straight chain or branched chain fluoro $C_{1-6}$alkyl group), an alkoxy group (e.g., a straight chain or branched chain $C_{1-6}$alkoxy group), a halogen-containing alkoxy group (e.g., a straight chain or branched chain fluoro$C_{1-6}$alkoxy group), and others. Moreover, the ring B having no substituent $R^3$ (that is, q=0) is also preferred. Incidentally, when the number q is not less than 2, the species of the substituents $R^3$ may be different or the same.

In the heterocycle C, the $-R^6-$ that connects two nitrogen atoms is a direct bond (or a single bond), a divalent group (e.g., an aliphatic divalent group which may have a substituent, an alicyclic divalent group which may have a substituent, and an aromatic divalent group which may have a substituent), or a trivalent group represented by the following formula (r6-1) or (r6-2).

[Formula 12]

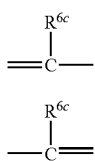

(r6-1)

(r6-2)

In the formulae, $R^{6c}$ represents a hydrogen atom or a substituent.

Incidentally, in the $-R^6-$, the direct bond shows a state that two nitrogen atoms of the heterocycle C directly link together.

In the $-R^6-$, the aliphatic divalent group may include a divalent saturated or unsaturated aliphatic hydrocarbon group such as an alkylene group (including an alkylidene group), an alkenylene group, or an alkynylene group, and others. The alkylene group may include a straight chain or branched chain $C_{1-6}$alkylene group (or a $C_{1-6}$alkylidene group) such as methylene group, ethylene group, ethylidene group, propylene group, trimethylene group, tetramethylene group, or hexamethylene group, preferably a $C_{1-4}$alkylene group (e.g., a $C_{1-3}$alkylene group), and others. The alkenylene group may include a straight chain or branched chain $C_{2-6}$alkenylene group such as vinylene group or propenylene group, preferably a $C_{2-4}$alkenylene group (e.g., a $C_{2-3}$alkenylene group), and others. The alkynylene group may include a $C_{2-6}$alkynylene group such as ethynylene group, preferably a $C_{2-4}$alkynylene group, and others.

The alicyclic divalent group may include a cycloalkylene group such as cyclohexylene group (e.g., a $C_{6-10}$cycloalkylene group), a cycloalkenylene group such as cyclohexenylene group (e.g., a $C_{6-10}$cycloalkenylene group), a divalent group corresponding to a dialkylcycloalkane such as cyclohexanedimethylene group or 1,1-dimethyl-3-methylcyclohexan-5-yl-3-methylene group (e.g., a divalent group corresponding to a di$C_{1-4}$alkyl$C_{6-10}$cycloalkane), and others.

The aromatic divalent group may include an arylene group such as a phenylene group (e.g., o-, m-, or p-phenylene group) or a naphthylene group (e.g., a $C_{6-10}$arylene group), an arenedialkylene group such as a xylylene group (e.g., a $C_{6-10}$arenedi$C_{1-4}$alkylene group), and others.

The substituent of these divalent groups may include a halogen atom (e.g., the halogen atom exemplified in the paragraph of the above-mentioned $R^2$), an alkyl group (e.g., the alkyl group exemplified in the paragraph of the above-mentioned $R^2$), an aryl group (e.g., a $C_{6-10}$aryl group such as phenyl group), an aralkyl group (e.g., a $C_{6-10}$aryl-$C_{1-4}$alkyl group such as benzyl group), an alkoxy group (e.g., the alkoxy group exemplified in the paragraph of the above-mentioned $R^2$), an acyl group (e.g., the acyl group exemplified in the paragraph of the above-mentioned $R^3$), an amino group, or an N-substituted amino group (e.g., the N-substituted amino group exemplified in the paragraph of the above-mentioned $R^3$), and others. The divalent group may have one or a plurality of these substituents. When the divalent group has a plurality of substituents, the species of the substituents may be the same or different.

In the $-R^6-$, the substituent $R^{6a}$ of the trivalent group represented by the formula (r6-1) or (r6-2) may include an alkyl group (e.g., the alkyl group exemplified in the paragraph of the above-mentioned $R^2$), an aryl group (e.g., a $C_{6-10}$aryl group such as phenyl group), and others.

In the formula (1), the heterocycle represented by the ring C may be either an aromatic heterocycle or a nonaromatic heterocycle and is usually represented by the following formula (1c-1) or (1c-2) in practical cases.

[Formula 13]

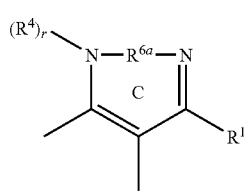

(1c-1)

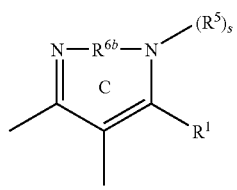

(1c-2)

In the formulae, $R^1$, $R^4$, $R^5$, $-R^{6a}-$, $-R^{6b}-$, r, and s have the same meanings as defined above.

Incidentally, the number r of $R^4$ denotes 0 or 1 depending on the species of the —$R^6$— and —$R^{6a}$—, the number of $R^5$ denotes 0 or 1 depending on the species of the —$R^6$— and —$R^{6b}$—. That is, when the heterocycle C in formula (1) is represented by the formula (1c-1) and (i) the —$R^6$— (and the —$R^{6a}$—) is a direct bond (or a single bond) or a divalent group, the number r of $R^4$ is 1; when the heterocycle C in formula (1) is represented by the formula (1c-1) and (ii) the —$R^6$— (and the —$R^{6a}$—) is a trivalent group (r6-1), the number r of $R^4$ is 0. Moreover, when the heterocycle C in the formula (1) is represented by the formula (1c-2) and (i) the —$R^6$—(and the —$R^{6b}$—) is a direct bond (or a single bond) or a divalent group, the number s of $R^5$ is 1; and when the heterocycle C in the formula (1) is represented by the formula (1c-2) and the —$R^6$— (and the —$R^{6b}$—) is the trivalent group (r6-2), the number s of $R^5$ is 0.

In the formula (1), the heterocycle C contains two nitrogen atoms and the group —$R^6$—. Depending on the species of the group —$R^6$—, the heterocycle C is usually a 5- to 10-membered ring (e.g., a 5- to 8-membered ring), preferably a 5- to 7-membered ring, and more preferably a 5- or 6-membered ring. The representative ring C includes a 5-membered ring such as a pyrazole ring, a 6-membered ring such as a pyrimidine ring, a 7-membered ring such as a diazepine ring, and others.

The preferred heterocycle C includes a 5- to 7-membered heterocycle, for example, heterocycles represented by the following formulae (1c-3) to (1c-7).

[Formula 14]

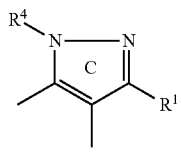
(1c-3)

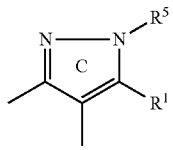
(1c-4)

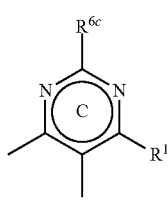
(1c-5)

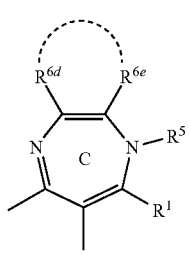
(1c-6)

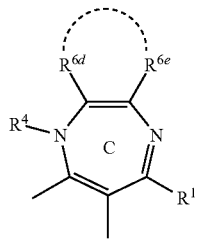
(1c-7)

In the formulae, $R^1$, $R^4$, $R^5$, $R^{6c}$ $R^{6d}$ and $R^{6e}$ have the same meanings as defined above.

In the substituents $R^4$ and $R^5$ on the nitrogen atoms constituting the heterocycle C, the alkyl group may include a straight chain or branched chain $C_{1-10}$alkyl group such as methyl group, ethyl group, propyl group, isopropyl group, butyl group, isobutyl group, s-butyl group, t-butyl group, pentyl group, isopentyl group, hexyl group, isohexyl group, heptyl group, or octyl group, and others. The alkyl group is usually a $C_{1-6}$alkyl group (e.g., a $C_{1-4}$alkyl group) and preferably a $C_{1-3}$alkyl group (e.g., a $C_{1-2}$alkyl group). The aryl group may include a $C_{6-10}$aryl group such as phenyl group or naphthyl group. The aralkyl group may include a $C_{6-10}$aryl-$C_{1-4}$alkyl group such as benzyl group or phenethyl group, and others. In the substituents $R^4$ and $R^5$, the acyl group may include a straight chain or branched chain $C_{1-10}$acyl group such as formyl group, acetyl group, propionyl group, butyryl group, isobutyryl group, valeryl group, pivaloyl group, or lauroyl group, and others. The acyl group is often a $C_{1-6}$acyl group and preferably a $C_{1-4}$acyl group (particularly a $C_{1-3}$acyl group).

In each of the substituents $R^4$ and $R^5$, the preferred one includes a hydrogen atom or an alkyl group.

In the formulae (r6-1), (r6-2), and (1c-5), the substituent represented by $R^{6c}$ may include an alkyl group (e.g., a $C_{1-6}$alkyl group such as methyl group), an alkenyl group (e.g., a $C_{2-6}$alkenyl group such as vinyl group), an alkynyl group (e.g., a $C_{2-6}$alkynyl group such as ethynyl group), an aryl group (e.g., a $C_{6-10}$aryl group which may have an alkyl group, such as phenyl group or tolyl group), and others.

In the formulae (1c-6) and (1c-7), the substituents represented by $R^{6d}$ and $R^{6e}$ may include a substituent similar to the substituent $R^3$ of the ring B. The preferred substituents $R^{6d}$ and $R^{6e}$ include a substituent similar to the above-mentioned preferred substituent $R^3$.

The groups $R^{6d}$ and $R^{6e}$ may bond together to form an aromatic or nonaromatic ring. Such an aromatic ring corresponds to the above-mentioned —$R^6$— and may include an arene ring such as a benzene ring or a naphthalene ring (e.g., a $C_{6-10}$arene ring), and others. Moreover, the nonaromatic ring corresponds to the above-mentioned —$R^6$— and may include a cycloalkane ring such as a cyclohexane (e.g., a $C_{6-8}$cycloalkane ring), a cycloalkene ring such as a cyclohexene ring (e.g., a $C_{6-8}$cycloalkene ring), and others. Among others, the arene ring such as a benzene ring is particularly preferred. The ring formed by bonding the groups $R^{6d}$ and $R^{6e}$ together may have a substituent.

When the aromatic ring formed by bonding the groups $R^{6d}$ and $R^{6e}$ together is a benzene ring, the formulae (1c-6) and (1c-7) may be represented by the following formulae (1c-8) and (1c-9), respectively.

[Formula 15]

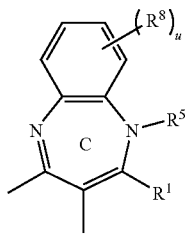

(1c-8)

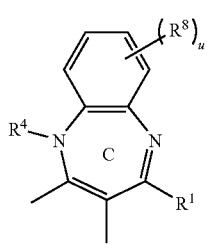

(1c-9)

In the formulae, $R^8$ represents a substituent, u denotes an integer of 0 to 4. The groups $R^1$, $R^4$, and $R^5$ have the same meanings as defined above.

As the substituent of the ring formed by bonding the groups $R^{6d}$ and $R^{6e}$ together (including the substituent $R^8$), there may be exemplified a substituent similar to the substituent $R^3$ of the ring B. The number of the substituents is not particularly limited to a specific one and may be about 0 to 5, preferably about 0 to 4, and more preferably about 0 to 3 (e.g., about 1 or 2). The number u of the substituents $R^8$ in the formulae (1c-8) and (1c-9) may be preferably about 0 to 3 and more preferably about 1 or 2.

In the formulae (1) and (1c-1) to (1c-9), the group $R^1$ is an alkyl group which may have a substituent. The alkyl group may include a straight chain or branched chain $C_{1-20}$alkyl group such as methyl, ethyl, propyl, isopropyl, n-butyl, isobutyl, t-butyl, hexyl, or octyl. Among these alkyl groups, a $C_{1-10}$alkyl group (e.g., a $C_{1-6}$alkyl group), particularly a $C_{1-4}$alkyl group, is preferred.

The substituent of the alkyl group may include a hydroxyl group, a halogen atom, a nitro group, an amino group, an N-substituted amino group, an alkoxy group which may have a substituent (e.g., the substituent exemplified in the paragraph of the above-mentioned $R^2$), a group represented by the following formula (1e), and others.

[Formula 16]

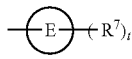

(1e)

In the formula, the ring E, $R^7$, and t have the same meanings as defined above.

In the substituted alkyl group, a halogen atom of the halogen-containing alkyl group may include fluorine, chlorine, bromine, or iodine atom, and others. The N-substituted amino group may include a mono- or di$C_{1-4}$alkylamino group such as methylamino group or dimethylamino group; a $C_{1-4}$acylamino group such as acetylamino group; and others.

The alkyl group may have a plurality of the substituents which may be the same or different from each other. In the alkyl group having the substituent, the number of the substituents is not particularly limited to a specific one and may be about 1 to 6, preferably about 1 to 4, and more preferably about 1 to 3. Moreover, in the alkoxy group having the substituent, the number of the substituents is not particularly limited to a specific one and may be about 1 to 6, preferably about 1 to 4, and more preferably about 1 to 3.

The preferred $R^1$ includes an alkyl group, a nitroalkyl group, an aminoalkyl group, an N-substituted aminoalkyl group, a halogen-containing alkyl group, an alkoxyalkyl group (e.g., a $C_{1-6}$alkoxy-alkyl group), an alkyl group having a halogen-containing alkoxy group (e.g., a halogen-containing $C_{1-6}$alkoxy-alkyl group), an alkyl group having a group represented by the formula (1e), and others.

In the formula (1e), the heterocycle represented by the ring E contains at least one heteroatom selected from the group consisting of a nitrogen atom, an oxygen atom, and a sulfur atom. The heterocycle may be either aromatic or nonaromatic. The heterocycle may include a nitrogen-containing heterocycle (e.g., a nitrogen atom-containing 5-membered ring such as a pyrrole ring, an imidazole ring, a pyrazole ring, an imidazolidine ring, an imidazoline ring, or a pyrazolidine ring; a nitrogen atom-containing 6-membered ring such as a piperidine ring, a piperazine ring, a pyridine ring, a pyrazine ring, a pyrimidine ring, or a pyridazine ring; and a nitrogen atom-containing fused (or condensed) heterocycle such as an indole ring, an isoquinoline ring, a quinoline ring, or a carbazole ring), a sulfur-containing heterocycle (e.g., a sulfur atom-containing 5-membered heterocycle such as a thiophene ring), an oxygen-containing heterocycle (e.g., an oxygen atom-containing 5-membered heterocycle such as a furan ring; an oxygen atom-containing 6-membered heterocycle group such as a pyran ring or a tetrahydropyran ring; an oxygen atom-containing fused heterocycle such as an isochroman ring or a chroman ring), a heterocycle containing different heteroatoms (e.g., a 5-membered or 6-membered heterocycle such as an isothiazole ring, an isoxazole ring, a furazane ring, or a morpholine ring), and others. The heterocycle is practically a nitrogen atom-containing 6-membered ring such as a pyridine ring, a sulfur atom-containing 5-membered heterocycle (particularly, e.g., a sulfur atom-containing 5-membered unsaturated heterocycle such as a thiophene ring), an oxygen-containing 6-membered heterocycle (particularly, e.g., an oxygen atom-containing 6-membered saturated heterocycle such as a tetrahydropyran ring), and others.

In the formula (1e), the carbocycle represented by the ring E may include the carbocycle exemplified in the paragraph of the ring B. As the carbocycle, a cycloalkane ring (e.g., a $C_{3-10}$cycloalkane ring) or an arene ring (e.g., a $C_{6-14}$arene ring), or the like is preferred. Among these carbocycles, usually, a $C_{6-10}$arene ring, particularly a benzene ring, is employed in practical cases.

Incidentally, the ring E may have either a carbon atom or a heteroatom (a nitrogen atom) as a bonding site to which the alkyl group constituting the group $R^1$ bonds. Moreover, the ring E and the ring B may be the same or different from each other. Each of the ring B and the ring E is usually a $C_{6-10}$arene ring (e.g., a benzene ring). As the substituent $R^7$ of the ring E, there may be exemplified a substituent similar to the substituent $R^3$ of the ring B. The preferred substituent $R^7$ includes a substituent similar to the preferred substituent $R^3$. Moreover, the ring E having no the substituent $R^7$ (that is, t=0) is also preferred. Incidentally, the substituent $R^7$ and the substituent $R^3$ may be the same or different. For example, each of the ring B and the ring E may have a substituent such as a halogen atom, a $C_{1-4}$alkyl group, a fluoro$C_{1-4}$alkyl group, a $C_{1-4}$alkoxy group, a fluoro$C_{1-4}$alkoxy group as the substituent $R^3$ and/or $R^7$, and at least one of the ring B and the ring E may have no substituent as the substituent $R^3$ and/or $R^7$. Further, the number t of the substituent $R^7$ may be selected from the same range as that of the number of the substituent $R^2$. Incidentally, when the number t is not less than 2, the species of the substituents $R^3$ may be different or the same.

The group $R^1$ may be, for example, a group represented by the following formula.

[Formula 17]

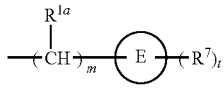

In the formula, $R^{1a}$ is a hydrogen atom or an alkyl group and the species of a plurality of $R^{1a}$s may be the same or different, m denotes an integer of 1 to 10; the ring E is a $C_{6-10}$arene ring, $R^7$ is a substituent selected from the group consisting of a halogen atom, a straight chain or branched chain $C_{1-6}$alkyl group, a straight chain or branched chain fluoro$C_{1-6}$alkyl group, a straight chain or branched chain $C_{1-6}$alkoxy group, and a straight chain or branched chain fluoro$C_{1-6}$alkoxy group; and the number t has the same meaning as defined above.

The alkyl group represented by the group $R^{1a}$ may include a straight chain or branched chain $C_{1-4}$alkyl group such as methyl group, ethyl group, n-propyl group, or isopropyl group, preferably a $C_{1-3}$alkyl group, and more preferably a $C_{1-2}$alkyl group. Moreover, the number m is preferably an integer of 1 to 6, more preferably an integer of 1 to 4 (e.g., 1 to 3), and usually 1 or 2 (particularly, 1).

Further, in a preferred embodiment, at least one of the ring B and the ring E has one substituent selected from the group consisting of the halogen-containing alkyl group (e.g., a chloroalkyl group and a fluoroalkyl group) and the halogen-containing alkoxy group (e.g., a chloroalkoxy group and a fluoroalkoxy group) as the substituent $R^3$ and/or $R^7$. In particular, when the group $R^1$ is a straight chain $C_{1-3}$alkyl group having a benzene ring, a thiophene ring or a pyridine ring as the ring E, the ring B is a benzene ring, the number p is 0, the —$R^6$— is a direct bond (or a single bond), and the fused (or condensed) ring comprising the ring A and the ring D is a fused (or condensed) ring represented by the following formula, the ring B and/or the ring E often has the halogen-containing alkyl group and/or the halogen-containing alkoxy group.

[Formula 18]

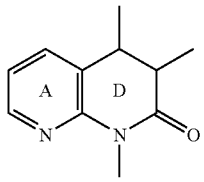

Moreover, when the group $R^1$ is an alkyl group having no substituent, the ring B usually has at least one substituent selected from the group consisting of the halogen-containing alkyl group and the halogen-containing alkoxy group as the substituent $R^3$.

Incidentally, in the halogen-containing alkyl group, at least a part of hydrogen atoms in the alkyl group may be replaced with halogen atom(s). The halogen-containing alkyl group may be a perhaloalkyl group in which all hydrogen atoms may be replaced with the same kind of halogen atoms. The halogen atom of the halogen-containing alkyl group is an iodine atom, a bromine atom, a chlorine atom, or a fluorine atom and is usually a chlorine atom or a fluorine atom.

The halogen-containing alkyl group may include, for example, a straight chain or branched chain halo$C_{1-10}$alkyl group, e.g., a halomethyl group such as chloromethyl, dichloromethyl, trichloromethyl, fluoromethyl, difluoromethyl, or trifluoromethyl; a haloethyl group such as a monochloroethyl, a dichloroethyl, a trichloroethyl, a tetrachloroethyl, pentachloroethyl, amonofluoroethyl, adifluoroethyl, atrifluoroethyl (e.g., 2,2,2-trifluoroethyl and 1,2,2-trifluoroethyl), a tetrafluoroethyl (e.g., 1,2,2,2-tetrafluoroethyl), pentafluoroethyl, or a chlorofluoroethyl (e.g., 1,1-dichloro-2,2,2-trifluoroethyl); a halopropyl group such as a monochloropropyl, a dichloropropyl, a trichloropropyl, atetrachloropropyl, apentachloropropyl, a hexachloropropyl, perchloropropyl, a monofluoropropyl, a difluoropropyl, a trifluoropropyl, a tetrafluoropropyl, a pentafluoropropyl, a hexafluoropropyl, or perfluoropropyl; a haloisopropyl group corresponding to the halopropyl group; a halobutyl group such as a trichlorobutyl, a trifluorobutyl, a tetrafluorobutyl, a hexafluorobutyl, or perfluorobutyl group; a haloisobutyl group, a s-halobutyl group, or a t-halobutyl group each corresponding to the halobutyl group; and perfluorohexyl group.

The halogen-containing alkoxy group may include, for example, a straight chain or branched chain halo$C_{1-10}$alkoxy group corresponding to the above-mentioned halo$C_{1-10}$alkyl group (e.g., a halomethoxy group such as trifluoromethoxy group, a haloethoxy group such as pentafluoroethoxy group, and a halopropoxy group such as perfluoropropoxy group).

At least one of the ring B and the ring E usually has at least one substituent selected from the group consisting of a straight chain or branched chain haloalkyl group and a straight chain or branched chain haloalkoxy group as the substituent $R^3$ and/or $R^7$. The preferred haloalkyl group includes, for example, a halo$C_{1-6}$alkyl group (e.g., a fluoro$C_{1-6}$alkyl group), preferably a halo$C_{1-4}$alkyl group (e.g., a fluoro$C_{1-4}$alkyl group), and particularly a halo$C_{1-3}$alkyl group (e.g., a fluoro$C_{1-3}$alkyl group). The preferred haloalkoxy group includes, for example, a halo$C_{1-6}$alkoxy group (e.g., a fluoro$C_{1-6}$alkoxy group), preferably a halo$C_{1-14}$alkoxy group (e.g., a fluoro$C_{1-4}$alkoxy group), and particularly a halo$C_{1-3}$alkoxy group (e.g., a fluoro$C_{1-3}$alkoxy group).

Moreover, the group $R^3$ and the group $R^7$ may be the same or different. The preferred combination of the group $R^3$ (or number q) and the group $R^7$ (or number t) is as follows.

(i) q: an integer of 1 to 4, $R^3$: a haloalkyl group, t: 0,
(ii) q: an integer of 1 to 4, $R^3$: a haloalkoxy group, t: 0,
(iii) q: 0, t: an integer of 1 to 4, $R^7$: a haloalkyl group,
(iv) q: 0, t: an integer of 1 to 4, $R^7$: a haloalkoxy group,
(v) q: an integer of 1 to 4, $R^3$: a haloalkyl group, t: an integer of 1 to 4, $R^7$: a haloalkyl group,
(vi) q: an integer of 1 to 4, $R^3$: a haloalkyl group, t: an integer of 1 to 4, $R^7$: a haloalkoxy group,
(vii) q: an integer of 1 to 4, $R^3$: a haloalkyl group, t: an integer of 1 to 4, $R^7$: a haloalkoxy group,
(vii) q: an integer of 1 to 4, $R^3$: a haloalkoxy group, t: an integer of 1 to 4, $R^7$: a haloalkyl group, and
(viii) q: an integer of 1 to 4, $R^3$: a haloalkoxy group, t: an integer of 1 to 4, $R^7$: a haloalkoxy group.

The representative examples of the heterocycle compound (1) of the present invention includes a compound represented by the following formula (for example, a pyrazolonaphthyridine derivative and a pyrazoloquinoline derivative).

[Formula 19]

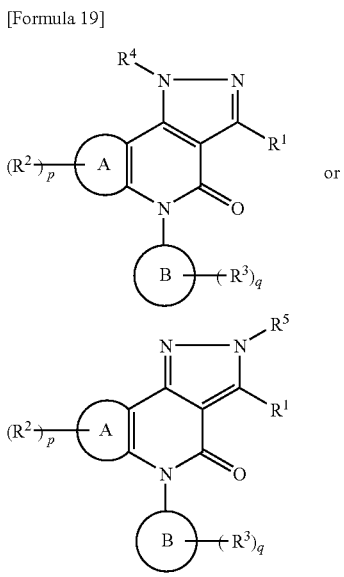

In the formula, the ring A represents a benzene ring or a pyridine ring. The ring B, $R^1$, $R^2$, $R^3$, $R^4$, $R^5$, p, and q have the same meanings as defined above.

The compound having a pyrazolonaphthyridine skeleton or a pyrazoloquinoline skeleton and an alkoxyalkyl group, a cycloalkylalkyl group, a fluorine-containing alkyl group, a phenylalkyl group, a fluoroalkylphenylalkyl group, or a fluoroalkoxyphenylalkyl group as the group $R^1$ may include a compound as described below. Incidentally, when the group $R^1$ is an atom or group other than the above-mentioned group (e.g., an alkyl group, a hydroxyalkyl group, a halogen-containing alkyl group other than a fluorine-containing alkyl group, a nitroalkyl group, an aminoalkyl group, an N-substituted aminoalkyl group, an alkoxyalkyl group having a substituent, and an alkyl group having a group represented by the formula (1e) other than the above-mentioned groups), compounds corresponding to the following compounds may be exemplified.

(i) Compounds in which $R^1$ is an alkoxyalkyl group:
(i-1) a 3-($C_{1-4}$alkoxy-$C_{1-3}$alkyl)-5-phenyl-1H-pyrazolo[4,3-c][1,8]-naphthyridin-4(5H)-one such as 3-(methoxymethyl)-5-phenyl-1H-pyrazolo[4,3-c][1,8]naphthyridin-4(5H)-one,
(i-2) a 3-($C_{1-4}$alkoxy-$C_{1-3}$alkyl)-5-(fluoro$C_{1-4}$alkyl-phenyl)-1H-pyrazolo[4,3-c][1,8]-naphthyridin-4(5H)-one,
(i-3) a 3-($C_{1-4}$alkoxy-$C_{1-3}$alkyl)-5-(fluoro$C_{1-10}$alkoxy-phenyl)-1H-pyrazolo[4,3-c][1,8]-naphthyridin-4(5H)-one, and others.

(ii) Compounds in which $R^1$ is a cycloalkylalkyl group:
(ii-1) a 3-($C_{4-10}$cycloalkyl-$C_{1-3}$alkyl)-5-phenyl-1H-pyrazolo[4,3-c][1,8]-naphthyridin-4(5H)-one such as 3-(cyclohexylmethyl)-5-phenyl-1H-pyrazolo[4,3-c][1,8]naphthyridin-4(5H)-one,
(ii-2) a 3-($C_{4-10}$cycloalkyl-$C_{1-3}$alkyl)-5-(fluoro$C_{1-4}$alkyl-phenyl)-1H-pyrazolo[4,3-c][1,8]-naphthyridin-4(5H)-one,
(ii-3) a 3-($C_{4-10}$cycloalkyl-$C_{1-3}$alkyl)-5-(fluoro$C_{1-4}$alkoxy-phenyl)-1h-pyrazolo[4,3-c][1,8]-naphthyridin-4(5H)-one, (iii) Compounds in which $R^1$ is a fluoroalkyl group:
(iii-1) a 3-(fluoro$C_{1-10}$alkyl)-5-phenyl-1H-pyrazolo[4,3-c][1,8]-naphthyridin-4(5H)-one such as 5-phenyl-3-(3,3,3-trifluoropropyl)-1H-pyrazolo[4,3-c][1,8]-naphthyridin-4(5H)-one,
(iii-2) 3-(fluoro$C_{1-10}$alkyl)-5-(fluoro$C_{1-4}$alkyl-phenyl)-1H-pyrazolo[4,3-c][1,8]-naphthyridin-4(5H)-one
(iii-3) 3-(fluoro$C_{1-10}$alkyl)-5-(fluoro$C_{1-4}$alkoxy-phenyl)-1H-pyrazolo[4,3-c][1,8]-naphthyridin-4(5H)-one, and others, (iv) Compounds in which $R^1$ is a phenylalkyl group:
(iv-1) a 3-(phenyl-$C_{1-6}$alkyl)-5-phenyl-1H-pyrazolo[4,3-c][1,8]-naphthyridin-4(5H)-one such as 3-benzyl-7-methyl-5-phenyl-1H-pyrazolo[4,3-c][1,8]-naphthyridin-4(5H)-one or 5-phenyl-3-(6-phenylhexyl)-1H-pyrazolo[4,3-c][1,8]naphthyridin-4(5H)-one,
(iv-2) a 3-(phenyl-$C_{1-3}$alkyl)-5-(fluoro$C_{1-4}$alkyl-phenyl)-1H-pyrazolo[4,3-c][1,8]-naphthyridin-4(5H)-one such as 3-benzyl-5-(3-trifluoromethylphenyl)-1H-pyrazolo[4,3-c][1,8]-naphthyridin-4(5H)-one or 3-(1-phenylethyl)-5-(3-trifluoromethylphenyl)-1H-pyrazolo[4,3-c][1,8]naphthyridin-4(5H)-one,
(iv-3) a 3-(phenyl-$C_{1-3}$alkyl)-5-(fluoro$C_{1-4}$alkoxy-phenyl)-1H-pyrazolo[4,3-c][1,8]-naphthyridin-4(5H)-one such as 3-benzyl-5-(3-trifluoromethoxyphenyl)-1H-pyrazolo[4,3-c][1,8]-naphthyridin-4(5H)-one or 3-(1-phenylethyl)-5-(3-trifluoromethoxyphenyl)-1H-pyrazolo[4,3-c][1,8]naphthyridin-4(5H)-one,
(iv-4) a 3-(phenyl-branched $C_{2-4}$alkyl)-5-phenyl-1H-pyrazolo[4,3-c][1,8]-naphthyridin-4(5H)-one such as 5-phenyl-3-(1-phenylethyl)-1H-pyrazolo[4,3-c][1,8]naphthyridin-4(5H)-one or 5-phenyl-3-(1-phenylpropyl)-1H-pyrazolo[4,3-c][1,8]naphthyridin-4(5H)-one,
(iv-5) a 3-(phenyl-branched $C_{2-4}$alkyl)-5-(fluoro$C_{1-4}$alkyl-phenyl)-1H-pyrazolo[4,3-c][1,8]-naphthyridin-4(5H)-one,
(iv-6) a 3-(phenyl-branched $C_{2-4}$alkyl)-5-(fluoro$C_{1-4}$alkoxy-phenyl)-1H-pyrazolo[4,3-c][1,8]-naphthyridin-4(5H)-one,
(iv-7) a 3-(phenyl-$C_{1-3}$alkyl)-5-phenyl-1H-pyrazolo[4,3-c][1,7]-naphthyridin-4(5H)-one such as 3-benzyl-5-phenyl-1H-pyrazolo[4,3-c][1,7]naphthyridin-4(5H)-one,
(iv-8) a 3-(phenyl-$C_{1-3}$alkyl)-5-phenyl-1H-pyrazolo[4,3-c][1,6]-naphthyridin-4(5H)-one such as 3-benzyl-5-phenyl-1H-pyrazolo[4,3-c][1,6]naphthyridin-4(5H)-one,
(iv-9) a 3-(phenyl-$C_{1-3}$alkyl)-5-phenyl-1H-pyrazolo[4,3-c][1,5]-naphthyridin-4(5H)-one such as 3-benzyl-5-phenyl-1H-pyrazolo[4,3-c][1,5]naphthyridin-4(5H)-one,
(iv-10) a 3-(phenyl-$C_{1-3}$alkyl)-5-phenyl-1H-pyrazolo[4,3-c]quinolin-4(5H)-one such as 3-benzyl-5-phenyl-1H-pyrazolo[4,3-c]quinolin-4(5H)-one, and others, (v) Compounds in which $R^1$ is a fluoroalkylphenylalkyl group:
(v-1) a 3-[(fluoro$C_{1-4}$-alkyl-phenyl)$C_{1-3}$alkyl]-5-phenyl-1H-pyrazolo[4,3-c][1,8]-naphthyridin-4(5H)-one such as 5-phenyl-3-(4-trifluoromethylbenzyl)-1H-pyrazolo[4,3-c][1,8]naphthyridin-4(5H)-one, 5-phenyl-3-(2-trifluoromethylbenzyl)-1H-pyrazolo[4,3-c][1,8]naphthyridin-4(5H)-one, or 5-phenyl-3-(3-trifluoromethylbenzyl)-1H-pyrazolo[4,3-c][1,8]naphthyridin-4(5H)-one,
(v-2) a 3-[(fluoro$C_{1-4}$alkyl-phenyl)$C_{1-3}$alkyl]-5-(fluoro$C_{1-4}$alkyl-phenyl)-1H-pyrazolo[4,3-c][1,8]-naphthyridin-4(5H)-one such as 3-(2-, 3- or 4-trifluoromethylbenzyl)-5-(3-trifluoromethylphenyl)-1H-pyrazolo[4,3-c][1,8]naphthyridin-4(5H)-one,
(v-3) a 3-[(fluoro$C_{1-4}$alkyl-phenyl)$C_{1-3}$alkyl]-5-(fluoro$C_{1-4}$alkoxy-phenyl)-1H-pyrazolo[4,3-c][1,8]-naphthyridin-4(5H)-one such as 5-(3-trifluoromethoxyphenyl)-3-(2-, 3- or 4-trifluoromethylbenzyl)-1H-pyrazolo[4,3-c][1,8]naphthyridin-4(5H)-one,
(v-4) a 3-[(fluoro$C_{1-4}$alkyl-phenyl) branched $C_{2-4}$alkyl]-5-phenyl-1H-pyrazolo[4,3-c][1,8]-naphthyridin-4(5H)-one, (v-5) a 3-[(fluoroC$_{1-4}$alkyl-phenyl) branched C$_{2-4}$alkyl]-5-(fluoroC$_{1-4}$alkyl-phenyl)-1H-pyrazolo[4,3-c][1,8]-naphthyridin-4(5H)-one, (v-6) a 3-[(fluoroC$_{1-4}$alkyl-phenyl) branched C$_{2-4}$alkyl]-5-(fluoroC$_{1-4}$alkoxy-phenyl)-1H-pyrazolo[4,3-c][1,8]-naphthyridin-4(5H)-one, and others, (vi) Compounds in which R$^1$ is a fluoroalkoxyphenylalkyl group:

(vi-1) a 3-[(fluoroC$_{1-4}$alkoxy-phenyl)C$_{1-3}$alkyl]-5-phenyl-1H-pyrazolo[4,3-c][1,8]-naphthyridin-4(5H)-one such as 5-phenyl-3-(2-trifluoromethoxybenzyl)-1H-pyrazolo[4,3-c][1,8]naphthyridin-4(5H)-one, 5-phenyl-3-(3-trifluoromethoxybenzyl)-1H-pyrazolo[4,3-c][1,8]naphthyridin-4(5H)-one, or 5-phenyl-3-(4-trifluoromethoxybenzyl)-1H-pyrazolo[4,3-c][1,8]naphthyridin-4(5H)-one, (vi-2) a 3-[(fluoroC$_{1-4}$alkoxy-phenyl)C$_{1-3}$alkyl]-5-(fluoroC$_{1-4}$alkyl-phenyl)-1H-pyrazolo[4,3-c][1,8]-naphthyridin-4(5H)-one such as 3-(2-, 3- or 4-trifluoromethoxybenzyl)-5-(3-trifluoromethylphenyl)-1H-pyrazolo[4,3-c][1,8]naphthyridin-4(5H)-one, (vi-3) a 3-[(fluoroC$_{1-4}$alkoxy-phenyl)C$_{1-3}$alkyl]-5-(fluoroC$_{1-4}$alkoxy-phenyl)-1H-pyrazolo[4,3-c][1,8]-naphthyridin-4(5H)-one such as 3-(2-, 3- or 4-trifluoromethoxybenzyl)-5-(3-trifluoromethoxyphenyl)-1H-pyrazolo[4,3-c][1,8]naphthyridin-4(5H)-one, (vi-4) a 3-[(fluoroC$_{1-4}$alkoxy-phenyl) branched C$_{2-4}$alkyl]-5-phenyl-1H-pyrazolo[4,3-c][1,8]-naphthyridin-4(5H)-one, (vi-5) a 3-[(fluoroC$_{1-4}$alkoxy-phenyl) branched C$_{2-4}$alkyl]-5-(fluoroC$_{1-4}$alkyl-phenyl)-1H-pyrazolo[4,3-c][1,8]-naphthyridin-4(5H)-one, (vi-6) a 3-[(fluoroC$_{1-4}$alkoxy-phenyl) branched C$_{2-4}$alkyl]-5-(fluoroC$_{1-4}$alkoxy-phenyl)-1H-pyrazolo[4,3-c][1,8]-naphthyridin-4(5H)-one, and others, (vii) Compounds in which R$^1$ is an alkylphenylalkyl group:

(vii-1) a 3-(C$_{1-4}$alkyl-phenyl-C$_{1-3}$alkyl)-5-(fluoroC$_{1-4}$alkyl-phenyl)-1H-pyrazolo[4,3-c][1,8]-naphthyridin-4(5H)-one such as 3-(2-methylbenzyl)-5-(3-trifluoromethylphenyl)-1H-pyrazolo[4,3-c][1,8]-naphthyridin-4(5H)-one, (vii-2) a 3-(C$_{1-4}$alkyl-phenyl-C$_{1-3}$alkyl)-5-(fluoroC$_{1-4}$alkoxy-phenyl)-1H-pyrazolo[4,3-c][1,8]-naphthyridin-4(5H)-one such as 3-(2-methylbenzyl)-5-(3-trifluoromethoxyphenyl)-1H-pyrazolo[4,3-c][1,8]-naphthyridin-4(5H)-one, and others, (viii) Compounds in which R$^1$ is a nitrophenylalkyl group:

(viii-1) a 3-(nitrophenyl-C$_{1-3}$alkyl)-5-(fluoroC$_{1-4}$alkyl-phenyl)-1H-pyrazolo[4,3-c][1,8]-naphthyridin-4(5H)-one such as 3-(2-nitrobenzyl)-5-(3-trifluoromethylphenyl)-1H-pyrazolo[4,3-c][1,8]-naphthyridin-4(5H)-one, (viii-2) a 3-(nitrophenyl-C$_{1-3}$alkyl)-5-(fluoroC$_{1-4}$alkoxy-phenyl)-1H-pyrazolo[4,3-c][1,8]-naphthyridin-4(5H)-one such as 3-(2-nitrobenzyl)-5-(3-trifluoromethoxyphenyl)-1H-pyrazolo[4,3-c][1,8]-naphthyridin-4(5H)-one, and others, (ix) Compound in which R$^1$ is an alkoxyphenylalkyl group:

(ix-1) a 3-(C$_{1-4}$alkoxy-phenyl-C$_{1-3}$alkyl)-5-(fluoroC$_{1-4}$alkyl-phenyl)-1h-pyrazolo[4,3-c][1,8]-naphthyridin-4(5H)-one such as 3-(2-methoxybenzyl)-5-(3-trifluoromethylphenyl)-1H-pyrazolo[4,3-c][1,8]-naphthyridin-4(5H)-one, (ix-2) a 3-(C$_{1-4}$alkoxy-phenyl-C$_{1-3}$alkyl)-5-(fluoroC$_{1-4}$alkoxy-phenyl)-1H-pyrazolo[4,3-c][1,8]-naphthyridin-4(5H)-one such as 3-(2-methoxybenzyl)-5-(3-trifluoromethoxyphenyl)-1H-pyrazolo[4,3-c][1,8]-naphthyridin-4(5H)-one, and others, (x) Compound in which R$^1$ is a halophenylalkyl group:

(x-1) a 3-(halophenyl-C$_{1-3}$alkyl)-5-(fluoroC$_{1-4}$alkyl-phenyl)-1H-pyrazolo[4,3-c][1,8]-naphthyridin-4(5H)-one such as 3-(4-fluorobenzyl)-5-(3-trifluoromethylphenyl)-1H-pyrazolo[4,3-c][1,8]-naphthyridin-4(5H)-one or 3-(2-chlorobenzyl)-5-(3-trifluoromethylphenyl)-1H-pyrazolo[4,3-c][1,8]-naphthyridin-4(5H)-one, (x-2) a 3-(halophenylC$_{1-3}$alkyl)-5-(fluoroC$_{1-4}$alkoxy-phenyl)-1H-pyrazolo[4,3-c][1,8]-naphthyridin-4(5H)-one such as 3-(4-fluorobenzyl)-5-(3-trifluoromethoxyphenyl)-1H-pyrazolo[4,3-c][1,8]-naphthyridin-4(5H)-one or 3-(2-chlorobenzyl)-5-(3-trifluoromethoxyphenyl)-1H-pyrazolo[4,3-c][1,8]-naphthyridin-4(5H)-one, and others, (xi) Compound in which R$^1$ is an alkyl group having an oxygen-containing 6-membered ring:

a 5-phenyl-3-(tetrahydro-2H-pyran-4-ylC$_{1-3}$alkyl)-1H-pyrazolo[4,3-c][1,8]naphthyridin-4(5H)-one which may have a substituent (e.g., a fluoroC$_{1-4}$alkyl group such as trifluoromethyl group, and a fluoroC$_{1-4}$alkoxy group such as trifluoromethoxy group) on phenyl group at 5-position thereof (e.g., 5-phenyl-3-(tetrahydro-2H-pyran-4-ylmethyl)-1H-pyrazolo[4,3-c][1,8]naphthyridin-4(5H)-one), and others, (xii) Compound in which R$^1$ is an alkyl group having a sulfur-containing 5-membered ring:

(xii-1) a 3-(thienylC$_{1-3}$alkyl)-5-(fluoroC$_{1-4}$alkyl-phenyl)-1H-pyrazolo[4,3-c][1,8]-naphthyridin-4(5H)-one such as 3-(2-thienylmethyl)-5-(3-trifluoromethylphenyl)-1H-pyrazolo[4,3-c][1,8]-naphthyridin-4(5H)-one or 3-(3-thienylmethyl)-5-(3-trifluoromethylphenyl)-1H-pyrazolo[4,3-c][1,8]-naphthyridin-4(5H)-one, (xii-2) a 3-(thienylC$_{1-3}$alkyl)-5-(fluoroC$_{1-4}$alkoxy-phenyl)-1H-pyrazolo[4,3-c][1,8]-naphthyridin-4(5H)-one such as 3-(2-thienylmethyl)-5-(3-trifluoromethoxyphenyl)-1H-pyrazolo[4,3-c][1,8]-naphthyridin-4(5H)-one or 3-(3-thienylmethyl)-5-(3-trifluoromethoxyphenyl)-1H-pyrazolo[4,3-c][1,8]-naphthyridin-4(5H)-one, and others.

The compound of the present invention may form a salt. Such a salt is also included in the present invention. As the salt, various physiologically or pharmacologically acceptable salts are applicable. An acid or base which forms the salt may be selected depending on the species of the compound (1). For example, such an acid or base may include a salt of an inorganic acid (for example, hydrochloric acid, sulfuric acid, nitric acid, and phosphoric acid), a salt of an organic acid (for example, an organic carboxylic acid, e.g., an organic carboxylic acid such as acetic acid, trichloroacetic acid, or trifluoroacetic acid, a hydroxycarboxylic acid such as succinic acid, citric acid, or tartaric acid; an organic sulfonic acid, e.g., an alkanesulfonic acid such as methanesulfonic acid or ethanesulfonic acid, and an arenesulfonic acid such as benzenesulfonic acid or toluenesulfonic acid), an inorganic base (e.g., ammonia, an alkali metal hydroxide such as sodium hydroxide or potassium hydroxide, an alkalimetal carbonate, an alkaline earth metal hydroxide such as calcium hydroxide or magnesium hydroxide, and an alkaline earth metal carbonate), and an organic base (e.g., an alkylamine, an alkanolamine, and a polyamine such as an alkylenediamine).

Incidentally, the compound (1) of the present invention may be the above-mentioned salt, in addition, a hydrate or a solvate (e.g., an ethanol solvate), a prodrug product in which the functional group of the compound (1) is modified to express an activity in a living body. The prodrug product may be a compound which can be transformed into the above-mentioned compound (1) by metabolism such as hydrolysis, oxidation, reduction, or transesterification (e.g., an ester of the compound (1), an ether thereof, an alcohol thereof, an amide thereof, and an amine derivative thereof). Further, the compound (1) of the present invention can be isolated as a hydrate, a solvate (e.g., an ethanol solvate), or a substance having various crystal structures.

Further, the present invention also includes a tautomer of the compound (1) or a salt thereof, an optically active substance having an asymmetric carbon atom (e.g., (R)-form, (S)-form, and a diastereomer), a racemic body, a mixture thereof, and others.

[Process for Producing Heterocycle Compound]

The heterocycle compound (1) or the salt thereof of the present invention may be produced by various processes, for example, in accordance with the following reaction chart.

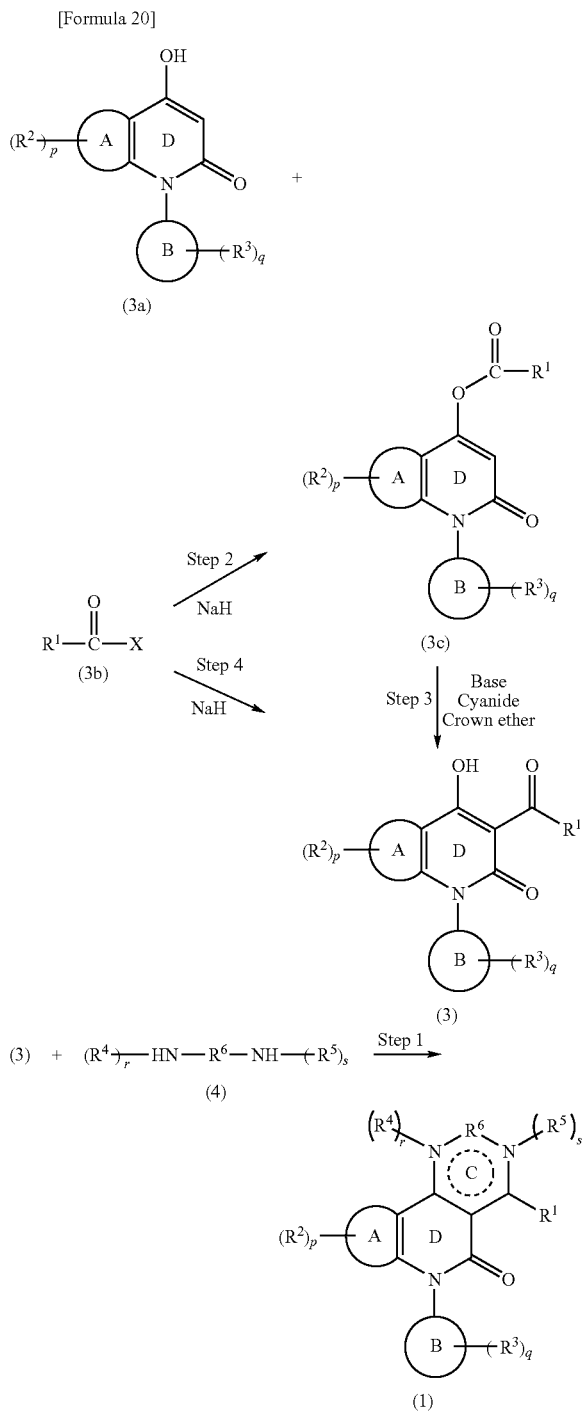

In the formula, X represents a halogen atom such as a chlorine atom or a bromine atom; and the ring A, the ring B, the ring C, the ring D, $R^1$, $R^2$, $R^3$, $R^5$, $R^4$, —$R^6$—, p, q, r, and s have the same meanings as defined above.

The heterocycle compound (1) of the present invention may be produced by synthesizing a compound (3a) according to a known process, allowing the compound (3a) to react with a carboxylic halide (3b) to give a compound (3), and allowing to the compound (3) to react with a diamine compound (4) (step 1).

Provided that, in the reaction chart, the compound represented by the formula (4) is a compound represented by the following formula (4a) or (4b), which corresponds to the above-mentioned formula (1c-1) or (1c-2).

[Formula 21]

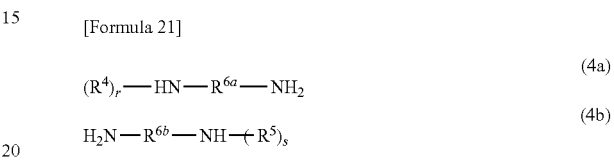

In the formulae, $R^4$, $R^5$, —$R^{6a}$—, —$R^{6b}$—, r, and have the same meanings as defined above.

Incidentally, in the formulae (4a) and (4b), when the —$R^{6a}$— and —$R^{6b}$— are a direct bond or the above-mentioned divalent group, each of r and s is 1. In the formula (4a), when —$R^{6a}$— is a trivalent group (r6-1), r is 0. In the formula (4b), when —$R^{6b}$— is a trivalent group (r6-2), s is 0. Incidentally, hereinafter, sometimes a compound (4) is a general term for the compound (4a) and/or compound (4b)

(Step 1)

In the step 1, from a reaction of the compound (3) with the diamine compound (4), the heterocycle compound of the present invention is synthesized.

The reaction of the compound (3) with the compound (4) may be carried out in the presence or absence of a solvent. The solvent may include various solvents inert to the reaction, for example, a hydrocarbon (e.g., an aliphatic hydrocarbon such as hexane, an alicyclic hydrocarbon such as cyclohexane, and an aromatic hydrocarbon such as toluene), a halogenated hydrocarbon (e.g., chloroform, dichloromethane, and trichloroethane), an alcohol (e.g., methanol, ethanol, and isopropanol), an ether (e.g., a chain ether such as diethyl ether or diisopropyl ether, and a cyclic ether such as dioxane or tetrahydrofuran), a nitrile (e.g., acetonitrile, propionitrile, and benzonitrile), a cellosolve, a carboxylic acid (e.g., acetic acid and propionic acid), an ester (e.g., ethyl acetate), a ketone (e.g., acetone and methyl ethyl ketone (MEK)), an amide (e.g., N,N-dimethylformamide (DMF) and N,N-dimethylacetamide), a sulfoxide (e.g., dimethylsulfoxide (DMSO)), and a sulfolane. These solvents may be used as a mixed solvent. As the solvent, usually, the alcohol, the ether, the carboxylic acid, or the amide is used in practical cases.

The proportion of the compound (3) and the compound (4) is not particularly limited to a specific one. Relative to 1 mol of the compound (3), the proportion of the compound (4) may be about 0.5 to 10 mol (e.g., about 1 to 8 mol, and preferably about 1.2 to 5 mol). In the above-mentioned reaction, if necessary, a base (for example, an inorganic base, e.g., an alkali metal carbonate such as potassium carbonate or sodium carbonate; an alkali metal alkoxide such as sodium methoxide) may be used.

The reaction may be conducted under an inactive (or inert) atmosphere. The reaction temperature may be selected from the range of about 0° C. to 200° C. The reaction temperature is usually about a room temperature (about 15 to 25° C.) to 160° C. and preferably about a room temperature (about 15 to 25° C.) to 120° C.

As the above-mentioned compound (4), there may be used a compound corresponding to the formula (1), that is, a hydrazine compound in which —$R^6$— is a direct bond, a diamine compound in which —$R^6$— is a divalent group, an amidine compound in which —$R^6$— is a trivalent group, and others. Such a compound (4) may include, depending on the species of $R^4$, $R^5$ and —$R^6$—, a hydrazine compound such as a hydrazine or an N-monosubstituted hydrazine; a diamine compound such as an alkanediamine, an N-monosubstituted alkanediamine, an alkenediamine, an N-monosubstituted alkenediamine, an arylenediamine, or a substituted arylenediamine; and others.

Moreover, the above-mentioned amidine compound may be represented by the following formula.

[Formula 22]

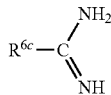

In the formula, the group $R^{6c}$ has the same meaning as defined above.

Such an amidine compound may include, depending on the species of the group $R^{6c}$, an amidinoalkane such as formamidine (HN=CH—$NH_2$) or acetoamidine (e.g., an amidino $C_{1-6}$alkane), an amidinoalkene such as amidinoethylene (e.g., an amidino$C_{2-6}$alkene), an amidinoalkyne such as amidinoethyne (e.g., an amidino$C_{2-6}$alkyne), an amidinoarene such as an amidinobenzene or an amidinotoluene (e.g., an amidino$C_{6-10}$arene), and others.

Incidentally, the above-mentioned compound (4) may be used in the form of a hydrate or a salt (e.g., a salt of an inorganic acid, such as hydrochloride).

The above-mentioned compound (3) may be obtained by a step 4 for allowing the compound (3a) to react with the acyl halide (3b); or by a step 2 for allowing the compound (3a) to react with the acyl halide (3b) and a step 3 for allowing the compound (3c) produced by the step 2 to react with a base, a cyanide, and a crown ether.

(Steps 2 to 4)

In the step 2, the compound (3a) is allowed to react with the acyl halide (3b) in the presence of sodium hydride, and the hydroxyl group of the compound (3a) is esterified to give the compound (3c). Then, in the step 3, the ester compound (3a) is allowed to react in the presence of the base, the crown ether and the cyanide to transform an acyl site constituting an ester site thereof, so that a hydroxy-acyl form (the compound (3)) can be obtained.

Incidentally, in the step 2, the amount of sodium hydride relative to the substrate compound (3a) is about 0.5 to 2 equivalents, preferably about 0.7 to 1.3 equivalents, and usually about 0.8 to 1.2 equivalents.

Incidentally, the compound (3c) may be synthesized by a conventional esterification reaction [for example, a reaction of the compound (3a) and the corresponding carboxylic acid with a condensing agent (e.g., dicyclohexylcarbodiimide)].

Moreover, in the step 3 in which the compound (3) is produced from the compound (3c), the base to be used may include an organic base (for example, an amine, e.g., an alkylamine such as trimethylamine or triethylamine), and in addition, an alkali or alkaline earth metal hydroxide (e.g., sodium hydroxide and potassium hydroxide), an alkali or alkaline earth metal carbonate (e.g., sodium carbonate), and an inorganic base such as ammonia. The crown ether may include a 9- to 30-membered crown ether such as 15-crown-5-ether, 12-crown-4-ether, or 18-crown-6-ether, and others. The cyanide may include, for example, analkali metal cyanide such as lithium cyanide, potassium cyanide, or sodium cyanide, and acetone cyanohydrin. Each of these components may be used singly or in combination. The amount of the base relative to 1 mol of the substrate (3c) is about 0.5 to 10 mol and preferably about 0.7 to 5 mol (e.g., about 1 to 1.5 mol). The amount of the crown ether relative to 1 mol of the substrate (3c) is about 0.01 to 10 mol (e.g., about 0.05 to 5 mol) and preferably about 0.1 to 1 mol (e.g., about 0.1 to 0.4 mol). The amount of the cyanide relative to 1 mol of the substrate (3c) is about 0.5 to 10 mol and preferably about 1 to 5 mol (e.g., about 1.5 to 2.5 mol) Incidentally, in the step 3, the crown ether is not necessarily needed. The base (e.g., an organic base) and the cyanide (e.g., acetone cyanohydrin) may be used in combination. In practice, the three components, that is, the base (e.g., an organic base), the crown ether, and the cyanide (e.g., an alkali metal cyanide) are used in combination.

Incidentally, in the excessive use of sodium hydride relative to the substrate compound (3a) in the reaction of the compound (3a) and the acyl halide (3b), the compound (3) can be sometimes directly obtained through the step 4.

In the step 4, the amount of sodium hydride is excessively lager than that of the substrate compound (3a), for example, about 1.5 to 4 equivalents (e.g., about 1.8 to 4 equivalents), preferably 2 to 3.5 equivalents, and more preferably 2 to 3 equivalents relative to the substrate compound (3a).

Incidentally, in the steps 2 and 4, an alkali metal hydride such as lithium hydride may be used without being limited to sodium hydride (NaH) as described above. The proportion of such an alkali metal hydride may be selected from the same range as described above.

The steps 2 to 4 may be conducted in the absence of a solvent and is conducted in the presence of a solvent in practical cases. As such a solvent, the solvent exemplified in the paragraph of the step 1, particularly the amide, the hydrocarbon (e.g., the aromatic hydrocarbon such as toluene), the nitrile, and others may be used. Moreover, in each step, at least one of the reaction components may be used as a reaction solvent. Each reaction may be usually conducted under an inactive gas, and if necessary by heating or cooling.

The production process of the compound (3) is not limited to the above-mentioned step 4 or the above-mentioned steps 2 and 3, and may be a manner according to these steps or a conventional manner.

Incidentally, the substrate compound (3a) used in the steps 2 and 4 may be produced by a conventional manner, for example, processes described in Japanese Patent Application Laid-Open No. 246183/1986 (JP-61-246183A), J. Med. Chem., 31, 2108 (1988), Japanese Patent Application Laid-Open No. 194515/1993 (JP-5-194515A), and others or processes according to these processes.

Incidentally, in the case of the compound (1) having the substituent ($R^2$, $R^3$, $R^4$, $R^5$, $R^{6c}$, $R^{6d}$, $R^{6e}$, $R^7$, $R^8$, and a substituent on these groups or $R^1$), the compound may be prepared by using a compound in which a substituent has been previously introduced into the compound (3) (also including precursors (3a), (3b), and (3c)) and/or the compound (4) or by introducing a substituent into the compound (1) which does not have the above-mentioned substituent with the use of a conventional manner (e.g., an oxidation, a reduction, a hydrolysis, and a substitution reaction). Moreover, among the above-mentioned substituents, a reactive group (e.g., a carboxyl group, a hydroxyl group, an amino group, an N-substituted amino group, a ureido group, a sulfonic acid group, a sulfinic acid group, and a sulfonamide group) may be protected, if necessary, by a protective group at an appropriate stage in the reaction. In addition, after the protection, the protective group may be removed or eliminated at an appropriate stage.

[Application]

The heterocycle compound or the salt thereof of the present invention has an extremely high phosphodiesterase IV inhibitory activity and is also highly safe. Therefore, the pharmaceutical composition (or pharmaceutical preparation) of the present invention contains the heterocycle compound (1) or a salt thereof (e.g., a pharmaceutically acceptable salt) as an effective ingredient (or an active ingredient). Moreover, the phosphodiesterase IV inhibitor of the present invention comprises the heterocycle compound (1) or a salt thereof. The agent or preparation of the present invention is useful for preventing and/or treating a disease in which phosphodiesterase IV directly or indirectly participates, for example, a respiratory disease.

Incidentally, in a conventional phosphodiesterase IV inhibitor, the difference between a dose for expressing a pharmacological effect such as an antiasthmatic action and a dose for inhibiting a drug metabolizing enzyme is small, or a drug metabolizing enzyme is inhibited in a smaller dose than the dose for expressing a pharmacological effect. Therefore, there is concern over restriction on the use of the inhibitor in a clinical application. On the contrary, the compound or the salt thereof of the present invention has an extremely small inhibitory action on a drug metabolizing enzyme (such as CYP2D6 or CYP3A4) compared with that of the conventional phosphodiesterase IV inhibitor. That is, in the compound or the salt thereof of the present invention, the dose for inhibiting the drug metabolizing enzyme is far higher than the dose for expressing the pharmacological effect. Therefore, the compound or the salt thereof of the present invention is particularly advantageous from the viewpoint of safety.

The respiratory disease may include a disease accompanied by a disorder or inflammation of a respiratory function in the bronchus or the respiratory tract area. Specific examples of the respiratory disease includes a disease selected from a bronchial asthma including chronic bronchial asthma and atopic asthma, acute bronchitis, chronic bronchitis, asthmatic bronchitis, pneumonic disease, pulmonary emphysema, chronic obstructive pulmonary disease (COPD), acute respiratory distress syndrome (ARDS), other bronchitis and respiratory tract inflammation, and the like.

The above-mentioned disease in which phosphodiesterase IV directly or indirectly participates may include, for example, the following diseases in addition to the above-mentioned respiratory disease.

A disease selected from the group consisting of (1) an inflammatory disease, for example, atopic dermatitis, conjunctivitis, urticaria, acquired immunodeficiency syndrome (AIDS), keloid formation, rhinitis, iridocyclitis, gingivitis, periodontitis, alveolar pyorrhea, gastritis, ulcerative colitis, Crohn's disease, gastrointestinal ulceration, esophagitis, myositis, encephalitis, hepetitis, scar tissue formation, a nephritis including proliferative nephritis, peritonitis, pleurisy, hidebound disease (or scleroderma), and burn; (2) a systemic or local joint disease, for example, knee osteoarthritis, urarthritis, chronic rheumatism (or rheumatoid arthritis), malignant rheumatoid arthritis, and psoriatic arthritis; (3) an inflammation after a transplantation, for example, reperfusion damage and graft versus host reaction; (4) a disease relating to dysuria, for example, diabetes insipidus, urethritis, in continence of urine, cystitis, hyper reflexic bladder, neuropathic bladder, uremia, tubular disorder, thamuria, and anuresis; (5) a disease in which tumor necrosis factor (e.g., TNF-$\alpha$) or other cytokines (e.g., IL-1, IL-4, and IL-6) participates, for example, psoriasis, chronic rheumatism, ulcerative colitis, Crohn's disease, sepsis, septic shock, endoteric shock, Gram-negative sepsis, toxic shock syndrome, nephritis, hepatitis, bacterial or viral infection, and a circulation insufficiency [e.g., cardiac incompetence, arteriosclerosis, cardiac infarction (or myocardial infraction), and apoplexia cerebri]; (6) a proliferative disease, for example, malignant tumor, leukemia, and dermatitis vegetans (e.g., keratosis and various types of dermatitis), connective tissue disease; (7) a disease relating to nerve malfunction, for example, a learning or memory disturbance or a cognitive disorder relating to a neurodegenerative disorder such as Alzheimer's disease or Parkinson's disease, multiple lateral sclerosis, multiple sclerosis, neuritis, dementia senilis, amyotrophic lateral sclerosis, acute demyelinating neuritis, and myodystrophy; (8) a disease relating to a mental function disorder, for example, manic-depressive psychosis, schizophrenia, anxiety, and panic; (9) a disease whose treatment needs protecting a nerve or a cell from a damage, for example, cardiac arrest, spinal cord injury, intermittent claudication, and ischemic disorder (e.g., angina pectoris, cardiac infarction, apoplexia cerebri, and head injury); (10) an endocrine disease including diabetes, for example, diabetic retinopathy, diabetic nephropathy, diabetic neuropathy, amyloidosis, pancreatitis, thyroiditis, obesity, and prostatomegaly; (11) an autoimmune disease such as systemic lupus erythematosus, atrophic gastritis, thyroid disease, glomerulonephritis, orchitis, adrenalopathy, hemolytic anemia, oophoritis, or myasthenia gravis; (12) a cardiovascular disease, for example, hypertension, angina pectoris, cardiac incompetence, myocarditis, epicarditis, endocarditis, and cardiovalvulitis; (13) a vascular or hematologic disease, for example, angiitis, aneurysm, intimal inflammation, thromboangiitis inflammation, granulomatosis, cerebrovascular inflammation, arteriosclerosis, perivascular inflammation, leukopenia, thrombocytopenia, and sarcoidosis; (14) a disease relating to an immunological allergic reaction, for example, contact dermatitis, serum sickness, drug allergy, Goodpasture's syndrome, lymphoma, rheumatic fever, AIDS, and anaphylactic shock; and (15) other diseases [e.g., glaucoma, spastic paralysis, impotence, a disease with pain (such as bruise or headache), cervico-omo-brachial syndrome, nephropathy, renal insufficiency, hepatic insufficiency, obesity, female sterility, and alopecia].

In these diseases, the drug (or pharmaceutical preparation) of the present invention is useful as a preventing and/or therapeutic agent for the diseases, particularly, the respiratory disease and the inflammatory disease. Incidentally, phosphodiesterase IV exists in large quantity in tracheal smooth muscle cells and inflammatory cells in a living body. The heterocycle compound or a salt thereof inhibits phosphodiesterase IV in these cells and exhibits a bronchodilator action due to relaxation of the tracheal smooth muscle and an anti-inflammatory action due to inhibition of the inflammatory cell activation. Therefore, particularly, the heterocycle compound or a salt thereof is widely effective for improvement in various adverse responses or symptoms developing in asthma and COPD. Accordingly, the drug (or pharmaceutical preparation) of the present invention is particularly useful for a preventive and/or therapeutic agent (an antasthmatic) for asthma (e.g., bronchial asthma) and a preventive and/or therapeutic agent for COPD.

Hereinafter, one of actions of the heterocycle compound or a salt thereof of the present invention, an antiasthmatic action, will be explained in more detail.

It is known that a series of responses including immediate asthmatic response, late asthmatic response, bronchial hypersensitive response, or the like is induced when a patient with asthma inhales an antigen as a cause of disease.

Firstly, the immediate asthmatic response, which starts right after antigen inhalation, is a typical contraction response of an airway smooth muscle and caused by a chemical transmitter (such as histamine or leukotriene) released from a mast cell due to an antigen antibody reaction. Next, the late asthmatic response is observed, which occurs in 4 to 24 hours after antigen inhalation. As a morbid condition of the response, an infiltration of inflammatory cells to a lung tissue, an edema of a mucous membrane of a respiratory tract, and others are observed. The respiratory tract hypersensitive response which is observed thereafter is a worse state of the respiratory tract response which occurs in 1 to 14 days after antigen inhalation. The respiratory tract contracts even by an extremely weak stimulus and falls into a state that a severe respiratory obstruction develops.

Thus, in asthma, various responses and symptoms are observed right after of antigen inhalation. The heterocycle compound or the salt thereof of the present invention can exert excellent inhibitory or improving actions on the responses and symptoms in each of steps described above due to a bronchodilator action and an anti-inflammatory action based on a phosphodiesterase IV inhibitory action.

The heterocycle compound or the salt thereof may be used alone as a medicine or in the form of a preparation containing a physiologically or pharmacologically acceptable carrier and/or additive, or others.

The form of the preparation is not particularly limited to a specific one and may be a solid preparation (for example, powdered preparations, powders, particles (e.g., granules and microfine particles or powders), spherical or spheroidal pills, pills, tablets, capsules, dry syrups, and suppositories), a semi-solid preparation (for example, creams, ointments, and gels), a liquid preparation (for example, solutions, suspensions, emulsions, gumdrop-like preparations, syrup, elixir, lotions, and injectable solutions (or injections)), and others. Moreover, sprays or aerosols of the powdered preparations and/or the liquid preparation may be also included. Incidentally, the capsules may be a capsule having a liquid filled therein or a capsule having a solid preparation (such as granules) filled therein. Moreover, the preparation may be a lyophilized preparation. Further, an agent contained in the preparation of the present invention may be released at a controlled rate, that is, the preparation of the present invention may be a sustained release preparation or a rapid-release preparation. Incidentally, in aerosols utilized for an inhalant agent and others, a method for generating an aerosol is not particularly limited to a specific one. For example, a medically effective ingredient and a propellant (e.g., an alternative for chlorofluorocarbon) may be filled in a single hermetic container and sprayed. Moreover, a medically effective ingredient and a compressed gas (such as carbon dioxide or nitrogen gas) may be filled in separate containers and sprayed in the form of a nebulizer or an atomizer.

The excipient may include a saccharide or a sugar alcohol such as lactose, white soft sugar or refined sugar, glucose, sucrose, mannitol, or sorbitol; a starch such as a corn starch; a polysaccharide such as a crystalline cellulose (including a microcrystalline cellulose); silicon dioxide or a silicate such as a light silicic anhydride or a synthetic aluminum silicate; and others. The binder may include a water-soluble starch such as a pregelatinized starch or a partially pregelatinized starch; a polysaccharide such as agar, gum acacia (or gum arabic), dextrin, sodium alginate, a tragacanth gum, a xanthan gum, a hyaluronic acid, or a sodium chondroitin sulfate; a synthetic polymer such as a polyvinylpyrrolidone, a polyvinyl alcohol, a carboxyvinyl polymer, a polyacrylic polymer, a polylactic acid, or a polyethylene glycol; a cellulose ether such as a methyl cellulose, an ethyl cellulose, a carboxymethyl cellulose, a carboxymethyl cellulose sodium, a hydroxyethyl cellulose, a hydroxypropyl cellulose, or a hydroxypropylmethyl cellulose; and others. The disintegrant may include calcium carbonate, a carboxymethyl cellulose or a salt thereof (e.g., a carmellose, a carmellose sodium, and a carmellose calcium), a polyvinylpyrrolidone (e.g., a polyvinylpyrrolidone and a crosslinked polyvinylpyrrolidone (crosslinked povidone)), a low-substituted hydroxypropyl cellulose, and others. These carriers may be used singly or in combination.

Incidentally, as a coating agent to be used for the coating, for example, there may be used a saccharide or a sugar, a cellulose derivative such as an ethyl cellulose or a hydroxymethyl cellulose, a polyoxyethylene glycol, a cellulose acetate phthalate, a hydroxypropylmethyl cellulose phthalate, a methyl methacrylate-(meth) acrylic acid copolymer, and eudragit (a copolymer of methacrylic acid and acrylic acid). The coating agent may be an enteric component (e.g., a cellulose phthalate, a hydroxypropylmethyl cellulose phthalate, and a methyl methacrylate-(meth)acrylic acid copolymer) or a gastric soluble component comprising a polymer containing a basic component such as a dialkylaminoalkyl (meth)acrylate (e.g., eudragit). Moreover, the preparation may be a capsule having such an enteric component or gastric soluble component as a capsule shell.

In the carrier of the liquid preparation, an oil-based carrier may include an oil derived from plants or animals (e.g., an oil derived from vegetables such as a jojoba oil, an olive oil, a palm oil, or a cotton seed oil; and an oil derived from animals such as squalene), a mineral oil (e.g., a liquid petrolatum and a silicone oil), and others. An aqueous carrier may include water (e.g., a purified water or a sterile water, a distilled water for injection), a physiological saline, a Ringer's solution, a glucose solution, a water-soluble organic solvent [for example, a lower aliphatic alcohol such as ethanol or isopropanol; a (poly)alkyleneglycol (e.g., ethylene glycol, diethyleneglycol, and a polyethyleneglycol); and glycerin], dimethyl isosorbide, dimethylacetamide, and others. Moreover, the carrier of the semisolid preparation may be selected from the carrier of the solid preparation and/or that of the liquid preparation. Further, the carrier of the semisolid preparation may contain a lipid.

The lipid may include a wax (e.g., a bees wax, a carnauba wax, a lanolin, a paraffin, and a petrolatum), a higher (or long chain) fatty acid ester [e.g., an alkyl ester of a saturated or unsaturated fatty acid, and an ester of a fatty acid with a polyvalent alcohol (such as a polyC$_{2-4}$alkyleneglycol, glycerin, or a polyglycerin) (e.g., a glyceride)], a hardened (or hydrogenated) oil, a higher alcohol (e.g., a saturated aliphatic alcohol such as stearyl alcohol and an unsaturated aliphatic alcohol such as oleyl alcohol), a higher fatty acid (e.g., stearic acid and oleic acid), a metallic soap (e.g., a metal salt of a fatty acid, such as a sodium salt of palm oil fatty acid or calcium stearate), and others.

In the preparation, known additives can be suitably used depending on an administration route, a dosage form, and others. Such an additive may include, for example, a lubricant (e.g., a talc, magnesium stearate, and a polyethylene glycol 6000), a disintegrant aid, an antioxidation agent or an antioxidant, an emulsifier (e.g., a variety of surfactants such as a nonionic surfactant), a dispersing agent, a suspending agent, a dissolving agent, a dissolution aid, a thickener (e.g., a water-soluble polymer such as a carboxyvinyl polymer, a polyvinyl alcohol, a carrageen, or a gelatin; and a cellulose ether such as a carboxymethyl cellulose), a pH adjusting agent or a buffer (e.g., a citric acid-sodium citrate buffer), a stabilizer, an antiseptic agent or a preservative (e.g., a paraben such as methyl paraben or butyl paraben), a fungicide or antibacterial agent (e.g., a benzoic acid compound such as sodium benzoate), an antistatic agent, a corrigent or a masking agent (e.g., sweetening agent), a coloring agent (e.g., a dye and a pigment such as colcothar), a deodorant or a perfume (e.g., an aromatic substance), an algefacient, an antifoaming agent, an isotonizing agent, and a soothing agent. These additives may be used singly or in combination. For example, in the injectable solution, usually, the dissolving agent, the dissolution aid, the suspending agent, the buffer, the stabilizer, the preservative, and others may be used as the additive in practical cases. Incidentally, to powders for an injection, which are dissolved or suspended before administration, may be added conventional additive(s) used for powders for an injection.

Moreover, in a topically administering preparation such as an inhalant preparation or a transdermal absorption preparation, as the additive, usually, the dissolution aid, the stabilizer, the buffer, the suspending agent, the emulsifier, the preservative, and others may be practically used.

The preparation of the present invention may be prepared by using a carrier component in addition to an effective ingredient, and if necessary, an additive and the like, with a conventional preparation manner (for example, a production process described in Japanese Pharmacopoeia 14$^{th}$ edition (JP XIV) or a process in accordance with the production process).

The drug (or pharmaceutical preparation) of the present invention is safely used for human beings and non-humans, usually mammals (e.g., human beings, mice, rats, rabbits, dogs, cats, bovines, horses, pigs, and monkeys).

The amount to be administered (or dose) of the drug (or pharmaceutical preparation) of the present invention may be suitably selected in accordance with the subject of administration, the age, bodyweight, sex, and condition (e.g., a performance status, a condition of a disease, and a presence of a complication) of the subject, the time (or period or schedule) of administration, the dosage form, the method (or route) of administration, and others. Moreover, the method of administration may be also selected in consideration of these items.

The amount to be administered (or dose) to human beings is, for example, in an oral administration, usually about 0.1 to 1,000 mg a day, preferably about 0.1 to 700 mg a day, and more preferably about 0.2 to 500 mg a day, in terms of the amount of the heterocycle compound. Moreover, in an injection, the amount to be administered to human beings is usually about 0.01 to 200 mg a day, preferably about 0.05 to 100 mg a day, and more preferably about 0.1 to 80 mg a day, in terms of the amount of the heterocycle compound. Further, in a topically administering agent, the amount to be administered to human beings is usually about 0.01 to 200 mg a day, preferably about 0.05 to 100 mg a day, and more preferably about 0.1 to 80 mg a day, in terms of the amount of the heterocycle compound.

INDUSTRIAL APPLICABILITY

Since the heterocycle compound or the salt thereof of the present invention has a high phosphodiesterase IV inhibitory activity and is highly safe, the heterocycle compound or the salt thereof is useful for a drug (or a pharmaceutical preparation), particularly, a drug (or pharmaceutical preparation) for preventing and/or treating a disease in which phosphodiesterase IV directly or indirectly participates (for example, a respiratory disease such as bronchial asthma or COPD), an inflammatory disease (e.g., atopic dermatitis), and other diseases.

EXAMPLES

The following examples are intended to describe this invention in further detail and should by no means be interpreted as defining the scope of the invention.

(1) Synthesis of material

Synthesis Example 1

4-Hydroxy-3-phenylacetyl-1-(3-trifluoromethoxyphenyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized, and the synthesized compound (644 mg, 2.0 mmol) was suspended in dimethylformamide (DMF) (16 mL). To the suspension was added sodium hydride (purity of about 60%, 264 mg, 6.6 mmol, 3.3 eq.), and the mixture was stirred until no more hydrogen was generated. Then, phenylacetyl chloride (0.32 mL, 2.4 mmol, 1.2 eq.) was added thereto, and the mixture was stirred at a room temperature for 2 hours. To the mixture was added water. The resulting mixture was acidified with hydrochloric acid, and then the resulting precipitate was separated by filtration and washed with water. The precipitate was purified by a flash column chromatography to give 4-hydroxy-3-phenylacetyl-1-(3-trifluoromethoxyphenyl)-1,8-naphthyridin-2(1H)-one as a form of crystal (254 mg, yield 29%).

mp: 140-142° C.

$^1$H NMR (CDCl$_3$) δ: 4.63 (2H, s), 7.16 (1H, m), 7.22-7.40 (7H, m), 7.23 (1H, dd, J=4.6 Hz, 7.9 Hz), 7.62 (1H, t, J=8.2 Hz), 8.52 (1H, dd, J=1.7 Hz, 7.9 Hz), 8.55 (1H, dd, J=2.0 Hz, 4.6 Hz)

Synthesis Example 2

4-Hydroxy-3-phenylacetyl-1-(3-trifluoromethylphenyl)-1,8-naphthyridin-2(1H)-one

In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (612 mg, 2.0 mmol) in DMF (16 mL) was added sodium hydride (purity of about 60%, 264 mg, 6.6 mmol, 3.3 eq.), and the mixture was stirred until no more hydrogen was generated. Then, phenylacetyl chloride (0.32 mL, 2.4 mmol, 1.2 eq.) was added thereto, and the mixture was stirred at a room temperature for 2 hours. To the mixture was added water. The resulting mixture was acidified with hydrochloric acid, and then the resulting precipitate was separated by filtration and washed with water. The precipitate was purified by a flash column chromatography to give 4-hydroxy-3-phenylacetyl-1-(3-trifluoromethylphenyl)-1,8-naphthyridin-2(1H)-one as a form of crystal (251 mg, yield 30%).

mp: 162-164° C.

¹H NMR (CDCl₃) δ: 4.62 (2H, s), 7.22-7.38 (6H, m), 7.47-7.56 (2H, m), 7.69-7.79 (2H, m), 8.52 (2H, dd, J=2.0 Hz, 4.0 Hz), 8.54 (1H, s)

Synthesis Example 3

4-Hydroxy-7-methyl-1-phenyl-3-phenylacetyl-1,8-naphthyridin-2(1H)-one

In accordance with a process described in JP-61-246183A or J. Med. Chem., 31, 2108 (1988) 4-hydroxy-7-methyl-1-phenyl-1,8-naphthyridin-2(1H)-one was synthesized. To a suspension of the synthesized compound (969 mg, 4.0 mmol) in DMF (16 mL) was added sodium hydride (purity of about 60%, 352 mg, 8.8 mmol, 2.2 eq.), and the mixture was stirred until no more hydrogen was generated. Then, phenylacetyl chloride (0.63 mL, 4.8 mmol, 1.2 eq.) was added thereto while cooling with ice, and the mixture was stirred at a room temperature for 1.5 hours. To the mixture was added water. The resulting mixture was acidified with hydrochloric acid, and then the resulting precipitate was separated by filtration and washed with water. The precipitate was dissolved in chloroform. The solution was dried over anhydrous magnesium sulfate, and the solvent was distilled off from the solution. The resulting residue was purified by a flash column chromatography to give 4-hydroxy-7-methyl-1-phenyl-3-phenylacetyl-1,8-naphthyridin-2(1H)-one as a form of crystal (935 mg, yield 63%).
mp: 163-168° C.
¹H NMR (CDCl₃) δ: 2.42 (3H, s), 4.63 (2H, s), 7.05 (1H, d, J=8.2 Hz), 7.15-7.62 (10H, m), 8.35 (1H, d, J=8.2 Hz).

Synthesis Example 4

4-Hydroxy-1-phenyl-3-(4-trifluoromethoxyphenylacetyl)-1,8-naphthyridin-2(1H)-one In accordance with a process described in JP-61-246183A, 4-hydroxy-1-phenyl-1,8-naphthyridin-2(1H)-one was synthesized. To a suspension of the synthesized compound (893 mg, 3.7 mmol) in DMF (16 mL) was added sodium hydride (purity of about 60%, 360 mg, 9.0 mmol, 2.4 eq.), and the mixture was stirred until no more hydrogen was generated. Then, 4-trifluoromethoxyphenylacetyl chloride (1.2 eq.) was added thereto, and the mixture was stirred at a room temperature for 3 hours. To the mixture was added water and further added a saturated sodium hydrogencarbonate solution, and the resulting mixture was subjected to extraction with dichloromethane. The extract was dried over anhydrous magnesium sulfate, and the solvent was distilled off from the extract. The resulting residue was purified by a flash column chromatography to give 4-hydroxy-1-phenyl-3-(4-trifluoromethoxyphenylacetyl)-1,8-naphthyridin-2(1H)-one (383 mg, yield 23%).
mp: 149-152° C.
¹H NMR (CDCl₃) δ: 4.64 (2H, s), 7.17-7.34 (7H, m), 7.53-7.64 (3H, m), 8.51-8.55 (1H, app-dd, J=2.2 Hz, 8.1 Hz), 8.56-8.58 (1H, app-dd, J=2.2 Hz, 4.6 Hz)

Synthesis Example 5

4-Hydroxy-1-phenyl-3-(2-trifluoromethylphenylacetyl)-1,8-naphthyridin-2(1H)-one

In accordance with a process described in JP-61-246183A, 4-hydroxy-1-phenyl-1,8-naphthyridin-2(1H)-one was synthesized. To a suspension of the synthesized compound (953 mg, 4.0 mmol) in DMF (32 mL) was added sodium hydride (purity of about 60%, 352 mg, 8.8 mmol, 2.2 eq.), and the mixture was stirred at a room temperature for 45 minutes. Then, 2-trifluoromethylphenylacetyl chloride (4.8 mmol, 1.2 eq.) was added thereto with cooling in an ice bath, and the mixture was stirred at a room temperature for 1.5 hours. Thereafter, the resulting mixture was purified by a flash column chromatography to give 4-hydroxy-1-phenyl-3-(2-trifluoromethylphenylacetyl)-1,8-naphthyridin-2(1H)-one as a form of crystal (972 mg, yield 57%).
mp: 140-142° C.
¹H NMR (CDCl₃) δ: 4.83 (2H, s), 7.20-7.25 (1H, dd, J=4.6 Hz, 7.9 Hz), 7.29-7.73 (9H, m), 8.51-8.55 (1H, dd, J=2.0 Hz, 7.9 Hz), 8.58-8.60 (1H, dd, J=2.0 Hz, 4.6 Hz)

Synthesis Example 6

4-Hydroxy-1-phenyl-3-(3-trifluoromethylphenylacetyl)-1,8-naphthyridin-2(1H)-one

In accordance with a process described in JP-61-246183A, 4-hydroxy-1-phenyl-1,8-naphthyridin-2(1H)-one was synthesized. To a suspension of the synthesized compound (953 mg, 4.0 mmol) in DMF (32 mL) was added sodium hydride (purity of about 60%, 352 mg, 8.8 mmol, 2.2 eq.), and the mixture was stirred at a room temperature for 35 minutes. Then, 3-trifluoromethylphenylacetyl chloride (4.8 mmol, 1.2 eq.) was added thereto with cooling in an ice bath, and the mixture was stirred at a room temperature for 1.5 hours. Thereafter, the resulting mixture was purified by a flash column chromatography to give 4-hydroxy-1-phenyl-3-(3-trifluoromethylphenylacetyl)-1,8-naphthyridin-2(1H)-one as a form of crystal (1.04 g, yield 61%).
mp: 201-203° C.
¹H NMR (CDCl₃) δ: 4.70 (2H, s), 7.20-7.25 (1H, dd, J=4.6 Hz, 7.9 Hz), 7.28-7.65 (9H, m), 8.51-8.55 (1H, dd, J=2.0 Hz, 7.9 Hz), 8.56-8.59 (1H, dd, J=2.0 Hz, 4.6 Hz)

Synthesis Example 7

4-Methoxyacetoxy-1-phenyl-1,8-naphthyridin-2(1H)-one

In accordance with a process described in JP-61-246183A, 4-hydroxy-1-phenyl-1,8-naphthyridin-2(1H)-one was synthesized. To a suspension of the synthesized compound (893 mg, 3.7 mmol) in DMF (20 mL) was added sodium hydride (purity of about 60%, 192 mg, 4.8 mmol, 1.3 eq.), and the mixture was stirred until no more hydrogen was generated. Then, methoxyacetyl chloride (1.07 g, 9.9 mmol, 2.6 eq.) was added thereto, and the mixture was stirred at a room temperature for 50 minutes. To the mixture was added water. The resulting mixture was acidified with concentrated hydrochloric acid, and then the resulting precipitate was separated by filtration and dried to give 4-methoxyacetoxy-1-phenyl-1,8-naphthyridin-2(1H)-one (847 mg, yield 73%).
mp: 155-157° C.
¹H NMR (CDCl₃) δ: 3.60 (3H, s), 4.46 (2H, s), 7.17-7.22 (1H, app-dd, J=4.9 Hz, 7.9 Hz), 7.28-7.31 (2H, m), 7.48-7.62 (3H, m), 7.98-8.01 (1H, app-dd, J=2.0 Hz, 7.9 Hz), 8.49-8.51 (1H, app-dd, 2.0 Hz, 4.9 Hz)

Synthesis Example 8

4-Hydroxy-1-phenyl-3-(2-phenylpropionyl)-1,8-naphthyridin-2(1H)-one (i) In accordance with a process described in JP-61-246183A, 4-hydroxy-1-phenyl-1,8-naphthyridin-2(1H)-one was synthesized. To a suspension of the synthesized compound (953 mg, 4.0 mol) in DMF (32 mL) was added sodium hydride (purity of about 60%, 192 mg, 4.8 mmol, 1.2 eq.), and the mixture was stirred until no more hydrogen was generated, to obtain a solution. Then, 2-phenylpropionyl chloride (1.2 eq.) was added thereto, and the mixture was stirred at a room temperature for 1 hour. To the mixture was added a saturated sodium hydrogencarbonate aqueous solution, and the resulting precipitate was separated by filtration, washed with water, and dried to give 1-phenyl-4-(2-phenylpropionyloxy)-1,8-naphthyridin-2(1H)-one as a form of crystal (1.45 g, yield 98%).

mp: 166-168° C.

$^1$H NMR (CDCl$_3$) δ: 1.70 (3H, d, J=7.3 Hz), 4.12 (1H, q, J=6.9 Hz), 6.70 (1H, s), 6.98 (1H, dd, J=4.6 Hz, 7.9 Hz), 7.22-7.27 (2H, m), 7.34-7.60 (9H, m), 8.40 (1H, dd, J=2.0 Hz, 4.6 Hz)

(ii) Dry toluene (50 mL) was added to 1-Phenyl-4-(2-phenylpropionyloxy)-1,8-naphthyridin-2(1H)-one (2.0 g, 5.40 mmol), triethylamine (546 mg, 5.40 mmol, 1 eq.), and potassium cyanide (706 mg, 10.8 mmol, 2 eq.), 18-crown-6 (280 mg), and the mixture was stirred at a room temperature for 3 days. Chloroform was added thereto. The insoluble residue was removed by using Celite, and the solvent of the resulting filtrate was distilled off. The resulting residue was purified by a flash column chromatography to give 4-hydroxy-1-phenyl-3-(2-phenylpropionyl)-1,8-naphthyridin-2(1H)-one as a form of crystal (714 mg, yield 36%).

mp: 140-151° C.

$^1$H NMR (CDCl$_3$) δ: 1.54 (3H, d, J=6.9 Hz), 5.73 (1H, q, J=6.9 Hz), 7.16 (1H, dd, J=4.6 Hz, 7.9 Hz), 7.19-7.61 (10H, m), 8.48 (1H, dd, J=2.0 Hz, 7.9 Hz), 8.51 (1H, dd, J=2.0 Hz, 4.6 Hz)

Synthesis Example 9

4-Hydroxy-1-phenyl-3-(7-phenylheptanoyl)-1,8-naphthyridin-2(1H)-one (i) In accordance with a process described in JP-61-246183A, 4-hydroxy-1-phenyl-1,8-naphthyridin-2(1H)-one was synthesized. To a suspension of the synthesized compound (953 mg, 4.0 mmol) in DMF (32 mL) was added sodium hydride (purity of about 60%, 176 mg, 4.4 mmol, 1.1 eq.), and the mixture was stirred at a room temperature for 40 minutes. Then, 7-phenylheptanoyl chloride (4.8 mmol, 1.2 eq.) was added thereto with cooling in an ice bath, and the mixture was stirred at a room temperature for 1.5 hours. Thereafter, the water was added to the reaction solution, and the precipitate was separated by filtration and dried to give 1-phenyl-4-(7-phenylheptanoyloxy)-1,8-naphthyridin-2(1H)-one as a form of crystal (1.52 g, yield 89%).

mp: 139-140° C.

$^1$H NMR (CDCl$_3$) δ: 1.41-1.53 (4H, m), 1.63-1.74 (2H, m), 1.78-1.89 (2H, m), 2.61-2.67 (2H, t, J=7.6 Hz), 2.69-2.75 (2H, t, J=7.6 Hz), 6.78 (1H, s), 7.15-7.21 (4H, m), 7.27-7.32 (4H, m), 7.47-7.62 (3H, m), 7.95-7.99 (1H, dd, J=2.0 Hz, 7.9 Hz), 8.47-8.50 (1H, dd, J=2.0 Hz, 4.6 Hz)

(ii) Dry toluene (30 mL) was added to 1-phenyl-4-(7-phenylheptanoyloxy)-1,8-naphthyridin-2(1H)-one (1.50 g, 3.52 mmol), triethylamine (0.49 mL, 3.52 mmol, 1 eq.), potassium cyanide (462 mg, 7.09 mmol, 2 eq.), and 18-crown-6 (180 mg), and the mixtures was stirred at a room temperature for 2 days. Dichloromethane was added thereto. The mixture was filtered by using Celite, and then the solvent was distilled off. The resulting residue was purified by a flash column chromatography to give an objective 4-hydroxy-1-phenyl-3-(7-phenylheptanoyl)-1,8-naphthyridin-2(1H)-one as a form of crystal (707 mg, yield 47%).

mp: 153-154° C.

$^1$H NMR (CDCl$_3$) δ: 1.37-1.39 (4H, m), 1.60-1.73 (4H, m), 2.55-2.61 (2H, t, J=7.6 Hz), 3.25-3.30 (2H, t, J=7.3 Hz), 7.14-7.28 (8H, m), 7.47-7.61 (3H, m), 8.51-8.56 (2H, m)

Synthesis Example 10

3-Cyclohexylacetyl-4-hydroxy-1-phenyl-1,8-naphthyridin-2(1H)-one (i) In accordance with a process described in JP-61-246183A, 4-hydroxy-1-phenyl-1,8-naphthyridin-2(1H)-one was synthesized. To a suspension of the synthesized compound (953 mg, 4.0 mmol) in DMF (32 mL) was added sodium hydride (purity of about 60%, 176 mg, 4.4 mmol, 1.1 eq.), and the mixture was stirred at a room temperature for 35 minutes. Then, cyclohexylacetyl chloride (4.8 mmol, 1.2 eq.) was added thereto with cooling in an ice bath, and the mixture was stirred at a room temperature for 80 minutes. Thereafter, water was added to the reaction mixture, and the precipitate was separated by filtration and dried to give 4-cyclohexylacetoxy-1-phenyl-1,8-naphthyridin-2(1H)-one as a form of crystal (1.33 g, yield 91%).

mp: 183-185° C.

$^1$H NMR (CDCl$_3$) δ: 1.06-1.43 (6H, m), 1.70-1.90 (4H, m), 1.94-2.06 (1H, m), 2.59-2.62 (2H, d, J=7.3 Hz), 6.78 (1H, s), 7.16-7.20 (1H, dd, J=4.6 Hz, 7.9 Hz), 7.27-7.30 (2H, m), 7.47-7.61 (3H, m), 7.97-8.00 (1H, dd, J=1.7 Hz, 7.9 Hz), 8.47-8.50 (1H, dd, J=1.7 Hz, 4.6 Hz)

(ii) Dry toluene (30 mL) was added to 4-cyclohexylacetoxy-1-phenyl-1,8-naphthyridin-2(1H)-one (1.31 g, 3.61 mmol), triethylamine (0.50 mL, 3.61 mmol, 1 eq.), potassium cyanide (472 mg, 7.24 mmol, 2 eq.), and 18-crown-6 (190 mg), and the mixtures was stirred at a room temperature for 2 days. Dichloromethane was added thereto. The mixture was filtered by using Celite, and then the solvent was distilled off. The resulting residue was purified by a flash column chromatography to give an objective 3-cyclohexylacetyl-4-hydroxy-1-phenyl-1,8-naphthyridin-2(1H)-one as a form of crystal (625 mg, yield 48%).

mp: 231-233° C.

$^1$H NMR (CDCl$_3$) δ: 0.83-1.36 (6H, m), 1.57-1.78 (4H, m), 1.92-2.08 (1H, m), 3.17-3.20 (2H, d, J=6.9 Hz), 7.18-7.22 (1H, dd, J=4.6 Hz, 7.9 Hz), 7.25-7.28 (2H, m), 7.47-7.62 (3H, m), 8.51-8.55 (2H, m)

Synthesis Example 11

4-Hydroxy-1-phenyl-3-(4,4,4-trifluorobutyryl)-1,8-naphthyridin-2(1H)-one (i) In accordance with a process described in JP-61-246183A, 4-hydroxy-1-phenyl-1,8-naphthyridin-2(1H)-one was synthesized. To a suspension of the synthesized compound (953 mg, 4.0 mmol) in DMF (32 mL) was added sodium hydride (purity of about 60%, 176 mg, 4.4 mmol, 1.1 eq.), and the mixture was stirred at a room temperature for 40 minutes. Then, 4,4,4-trifluorobutyryl chloride (4.4 mmol, 1.1 eq.) was added thereto with cooling in an ice bath, and the mixture was stirred at a room temperature for 2 hours. Thereafter, a sodium hydrogencarbonate aqueous solution and water were added to the reaction solution, and the precipitate was separated by filtration and dried to give 1-phenyl-4-(4,4, 4-trifluorobutyryloxy)-1,8-naphthyridin-2(1H)-one as a form of crystal (955 mg, yield 66%).

mp: 193-195° C.

$^1$H NMR (CDCl$_3$) δ: 2.58-2.75 (2H, m), 3.02-3.08 (2H, t, J=7.3 Hz), 6.80 (1H, s), 7.17-7.22 (1H, dd, J=4.9 Hz, 7.9 Hz), 7.26-7.31 (2H, m), 7.48-7.62 (3H, m), 7.96-7.99 (1H, dd, J=2.0 Hz, 7.9 Hz), 8.49-8.52 (1H, dd, J=2.0 Hz, 4.9 Hz)

(ii) Dry toluene (22 mL) was added to 1-phenyl-4-(4,4,4-trifluorobutyryloxy)-1,8-naphthyridin-2(1H)-one (930 mg, 2.57 mmol), triethylamine (0.36 mL, 2.57 mmol, 1 eq.), potassium cyanide (338 mg, 5.19 mmol, 2 eq.), and 18-crown-6 (136 mg), and the mixtures was stirred at a room temperature for 3 days. Dichloromethane was added thereto. The mixture was filtered by using Celite, and then the solvent was distilled off. The resulting residue was purified by a flash column chromatography to give an objective 4-hydroxy-1-phenyl-3-(4,4,4-trifluorobutyryl)-1,8-naphthyridin-2(1H)-one as a form of crystal (82 mg, yield 9%).

mp: 217-220° C.

$^1$H NMR (CDCl$_3$) δ: 2.46-2.64 (2H, m), 3.57-3.63 (2H, t, J=7.3 Hz), 7.21-7.28 (3H, m), 7.48-7.64 (3H, m), 8.52-8.56 (1H, dd, J=2.0 Hz, 7.9 Hz), 8.57-8.60 (1H, dd, J=2.0 Hz, 4.9 Hz)

Synthesis Example 12

4-Hydroxy-1-phenyl-3-phenylacetyl-1,6-naphthyridin-2(1H)-one

In accordance with a process described in JP-61-246183A or J. Med. Chem., 31, 2108 (1988), 4-hydroxy-1-phenyl-1,6-naphthyridin-2(1H)-one was synthesized. To a suspension of the synthesized compound (477 mg, 2.0 mmol) in DMF (20 mL) was added sodium hydride (purity of about 60%, 176 mg, 4.4 mmol, 2.2 eq.), and the mixture was stirred for 40 minutes. Then, phenylacetyl chloride (0.32 mL, 2.4 mmol, 1.2 eq.) was added thereto, and the mixture was stirred at a room temperature overnight. To the mixture was added water. The resulting mixture was acidified with hydrochloric acid, and then the resulting precipitate was separated by filtration to give 4-hydroxy-1-phenyl-3-phenylacetyl-1,6-naphthyridin-2(1H)-one as a form of crystal (58 mg, yield 8%).

$^1$H NMR (CDCl$_3$) δ: 4.59 (2H, s), 6.46-6.48 (1H, d, J=5.9 Hz), 7.24-7.40 (7H, m), 7.55-7.68 (3H, m), 8.47-8.49 (1H, d, J=5.9 Hz), 9.37 (1H, s)

Synthesis Example 13

4-Hydroxy-1-phenyl-37-phenylacetyl-quinolin-2(1H)-one

In accordance with a process described in JP-61-246183A or J. Med. Chem., 31, 2108 (1988), 4-hydroxy-1-phenylquinolin-2(1H)-one was synthesized. To a suspension of the synthesized compound (475 mg, 2.0 mmol) in DMF (16 mL) was added sodium hydride (purity of about 60%, 176 mg, 4.4 mmol, 2.2 eq.), and the mixture was stirred until no more hydrogen was generated. Then, phenylacetyl chloride (0.32 mL, 2.4 mmol, 1.2 eq.) was added thereto, and the mixture was stirred at a room temperature for 3 hours. To the mixture was added water. The resulting mixture was acidified with hydrochloric acid and filtered by using Celite. The residue was dissolved in chloroform and dried over anhydrous magnesium sulfate, and then the solvent was distilled off. The resulting residue was purified by a flash column chromatography to give 4-hydroxy-1-phenyl-3-phenylacetyl-quinolin-2(1H)-one as a form of crystal (290 mg, yield 41%).

mp: 155-158° C.

$^1$H NMR (CDCl$_3$) δ: 4.64 (2H, s), 6.57-6.60 (1H, d, J=8.2 Hz), 7.16-7.66 (12H, m), 8.22-8.25 (1H, dd, J=1.0 Hz, 7.9 Hz)

Synthesis Example 14

4-Hydroxy-1-(3-trifluoromethylphenyl)-3-(2-trifluoromethylphenylacetyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (919 mg, 3.0 mmol) in DMF (15 mL) was added sodium hydride (purity of about 60%, 264 mg, 6.6 mmol, 2.2 eq.), and the mixture was stirred until no more hydrogen was generated. Then, 2-trifluoromethylphenylacetyl chloride (3.6 mmol, 1.2 eq.) which had been previously prepared was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-1-(3-trifluoromethylphenyl)-3-(2-trifluoromethylphenylacetyl)-1,8-naphthyridin-2(1H)-one as a form of crystal (917 mg, yield 62%).

mp: 178-181° C.

$^1$H NMR (DMSO-d$_6$) δ: 4.77 (2H, s), 7.39-7.54 (3H, m), 7.63-7.88 (6H, m), 8.53-8.62 (2H, m)

Synthesis Example 15

4-Hydroxy-1-(3-trifluoromethylphenyl)-3-(3-trifluoromethylphenylacetyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (919 mg, 3.0 mmol) in DMF (15 mL) was added sodium hydride (purity of about 60%, 264 mg, 6.6 mmol, 2.2 eq.), and the mixture was stirred until no more hydrogen was generated. Then, 3-trifluoromethylphenylacetyl chloride (3.6 mmol, 1.2 eq.) which had been previously prepared was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-1-(3-trifluoromethylphenyl)-3-(3-trifluoromethylphenylacetyl)-1,8-naphthyridin-2(1H)-one as a form of crystal (918 mg, yield 62%).

mp: 118-121° C.

$^1$H NMR (DMSO-d$_6$) δ: 4.66 (2H, s), 7.38-7.42 (1H, dd, J=4.6 Hz, 7.8 Hz), 7.55-7.68 (5H, m), 7.77-7.87 (3H, m), 8.53-8.61 (2H, m)

Synthesis Example 16

4-Hydroxy-1-(3-trifluoromethylphenyl)-3-(4-trifluoromethylphenylacetyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (1.23 g, 4.0 mmol) in DMF (20 mL) was added sodium hydride (purity of about 60%, 353 mg, 8.8 mmol, 2.2 eq.), and the mixture was stirred until no more hydrogen was generated. Then, 4-trifluoromethylphenylacetyl chloride (4.8 mmol, 1.2 eq.) which had been previously prepared was added thereto, and the mixture was stirred at a room temperature for 1 hour. To the mixture was added water. The resulting mixture was acidified with hydrochloric acid, and the precipitate was separated by filtration and washed with water. The precipitate was purified by a flash column chromatography to give 4-hydroxy-1-(3-trifluoromethylphenyl)-3-(4-trifluoromethylphenylacetyl)-1,8-naphthyridin-2(1H)-one (1.06 g, yield 54%).

mp: 72-74° C.
$^1$H NMR (CDCl$_3$) δ: 4.67 (2H, s), 7.23-7.28 (1H, m), 7.36-7.80 (8H, m), 8.52-8.55 (2H, m)

Synthesis Example 17

4-hydroxy-3-(2-trifluoromethoxyphenylacetyl)-1-(3-trifluoromethylphenyl)-1,8-naphthyridine-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (919 mg, 3.0 mmol) in DMF (15 mL) was added sodium hydride (purity of about 60%, 264 mg, 6.6 mmol, 2.2 eq.), and the mixture was stirred until no more hydrogen was generated. Then, 2-trifluoromethoxyphenylacetyl chloride (3.6 mmol, 1.2 eq.) which had been previously prepared was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(2-trifluoromethoxyphenylacetyl)-1-(3-trifluoromethylphenyl)-1,8-naphthyridin-2(1H)-one as a form of crystal (1.07 g, yield 70%).

mp: 98-102° C.
$^1$H NMR (DMSO-d$_6$) δ: 4.63 (2H, s), 7.36-7.47 (5H, m), 7.69 (1H, d, J=7.8 Hz), 7.77-7.87 (3H, m), 8.54-8.61 (2H, m)

Synthesis Example 18

4-Hydroxy-3-(3-trifluoromethoxyphenylacetyl)-1-(3-trifluoromethylphenyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (613 mg, 2.0 mmol) in DMF (10 mL) was added sodium hydride (purity of about 60%, 176 mg, 4.4 mmol, 2.2 eq.), and the mixture was stirred until no more hydrogen was generated. Then, 3-trifluoromethoxyphenylacetyl chloride (2.4 mmol, 1.2 eq.) which had been previously prepared was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(3-trifluoromethoxyphenylacetyl)-1-(3-trifluoromethylphenyl)-1,8-naphthyridine-2(1H)-one as a form of crystal (496 mg, yield 49%).

mp: 51-54° C.
$^1$H NMR (DMSO-d$_6$) δ: 4.60 (2H, s), 7.24-7.32 (3H, m), 7.38-7.48 (2H, m), 7.66 (1H, d, J=7.6 Hz), 7.77-7.87 (3H, m), 8.53-8.60 (2H, m)

Synthesis Example 19

4-Hydroxy-3-(4-trifluoromethoxyphenylacetyl)-1-(3-trifluoromethylphenyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (613 mg, 2.0 mmol) in DMF (15 mL) was added sodium hydride (purity of about 60%, 176 mg, 4.4 mmol, 2.2 eq.), and the mixture was stirred until no more hydrogen was generated. Then, 4-trifluoromethoxyphenylacetyl chloride (2.4 mmol, 1.2 eq.) which had been previously prepared was added thereto, and the mixture was stirred at a room temperature for 1 hour. To the mixture was added water. The resulting mixture was acidified with hydrochloric acid, and the precipitate was separated by filtration and washed with water. The precipitate was purified by a flash column chromatography to give 4-hydroxy-3-(4-trifluoromethoxyphenylacetyl)-1-(3-trifluoromethylphenyl)-1,8-naphthyridin-2(1H)-one (310 mg, yield 30%).

mp: 49-51° C.
$^1$H NMR (CDCl$_3$) δ: 4.61 (2H, s), 7.16-7.33 (5H, m), 7.46-7.54 (2H, m), 7.64-7.79 (2H, m), 8.52-8.55 (2H, m)

Synthesis Example 20

4-Hydroxy-1-(3-trifluoromethoxyphenyl)-3-(2-trifluoromethylphenylacetyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. To a suspension of the synthesized compound (806 mg, 2.5 mmol) in DMF (15 mL) was added sodium hydride (purity of about 60%, 220 mg, 5.5 mmol, 2.2 eq.), and the mixture was stirred until no more hydrogen was generated. Then, 2-trifluoromethylphenylacetyl chloride (3.0 mmol, 1.2 eq.) which had been previously prepared was added thereto, and the mixture was stirred at a room temperature for 1 hour. To the mixture was added water. The resulting mixture was acidified with hydrochloric acid, and the precipitate was separated by filtration and washed with water. The precipitate was purified by a flash column chromatography to give 4-hydroxy-1-(3-trifluoromethoxyphenyl)-3-(2-trifluoromethylphenylacetyl)-1,8-naphthyridin-2(1H)-one as a form of crystal (772 mg, yield 61%).

mp: 76-78° C.
$^1$H NMR (DMSO-d$_6$) δ: 4.77 (2H, s), 7.39-7.54 (6H, m), 7.63-7.75 (3H, m), 8.54 (1H, dd, J=1.3 Hz, 7.8 Hz), 8.62 (1H, dd, J=1.4 Hz, 4.8 Hz)

Synthesis Example 21

4-Hydroxy-1-(3-trifluoromethoxyphenyl)-3-(3-trifluoromethylphenylacetyl)-1,8-naphthyridine-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. To a suspension of the synthesized compound (806 mg, 2.5 mmol) in DMF (15 mL) was added sodium hydride (purity of about 60%, 220 mg, 5.5 mmol, 2.2 eq.), and the mixture was stirred until no more hydrogen was generated. Then, 3-trifluoromethylphenylacetyl chloride (3.0 mmol, 1.2 eq.)

which had been previously prepared was added thereto, and the mixture was stirred at a room temperature for 1 hour. To the mixture was added water. The resulting mixture was acidified with hydrochloric acid, and the precipitate was separated by filtration and washed with water. The precipitate was purified by a flash column chromatography to give 4-hydroxy-1-(3-trifluoromethoxyphenyl)-3-(3-trifluoromethylphenylacetyl)-1,8-naphthyridin-2(1H)-one as a form of crystal (266 mg, yield 21%).

mp: 115-118° C.
$^1$H NMR (DMSO-$d_6$) δ: 4.66 (2H, s), 7.38-7.51 (4H, m), 7.55-7.72 (5H, m), 8.53 (1H, dd, J=1.9 Hz, 7.8 Hz), 8.61 (1H, dd, J=1.6 Hz, 4.6 Hz)

Synthesis Example 22

4-Hydroxy-1-(3-trifluoromethoxyphenyl)-3-(4-trifluoromethylphenylacetyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. To a suspension of the synthesized compound (967 mg, 3.0 mmol) in DMF (20 mL) was added sodium hydride (purity of about 60%, 264 mg, 6.6 mmol, 2.2 eq.), and the mixture was stirred until no more hydrogen was generated. Then, 4-trifluoromethylphenylacetyl chloride (3.6 mmol, 1.2 eq.) which had been previously prepared was added thereto with cooling in an ice bath, and the mixture was stirred at a room temperature for 1 hour. To the mixture was added water. The resulting mixture was acidified with hydrochloric acid, and the precipitate was separated by filtration and washed with water. The precipitate was purified by a flash column chromatography to give 4-hydroxy-1-(3-trifluoromethoxyphenyl)-3-(4-trifluoromethylphenylacetyl)-1,8-naphthyridin-2(1H)-one as a form of crystal (646 mg, yield 42%).

mp: 162-165° C.
$^1$H NMR (CDCl$_3$) δ: 4.68 (2H, s), 7.15-7.27 (3H, m), 7.36-7.42 (3H, m), 7.58-7.68 (3H, m), 8.51-8.57 (2H, m)

Synthesis Example 23

4-Hydroxy-1-(3-trifluoromethoxyphenyl)-3-(2-trifluoromethoxyphenylacetyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. To a suspension of the synthesized compound (806 mg, 2.5 mmol) in DMF (15 mL) was added sodium hydride (purity of about 60%, 220 mg, 5.5 mmol, 2.2 eq.), and the mixture was stirred until no more hydrogen was generated. Then, 2-trifluoromethoxyphenylacetyl chloride (3.0 mmol, 1.2 eq.) which had been previously prepared was added thereto, and the mixture was stirred at a room temperature for 1 hour. To the mixture was added water. The resulting mixture was acidified with hydrochloric acid, and the precipitate was separated by filtration and washed with water. The precipitate was purified by a flash column chromatography to give 4-hydroxy-1-(3-trifluoromethoxyphenyl)-3-(2-trifluoromethoxyphenylacetyl)-1,8-naphthyridin-2(1H)-one as a form of crystal (482 mg, yield 37%).

mp: 110-113° C.
$^1$H NMR (DMSO-$d_6$) δ: 4.63 (2H, s), 7.33-7.51 (8H, m), 7.68 (1H, t, J=8.1 Hz), 8.54 (1H, dd, J=1.9 Hz, 7.8 Hz), 8.61 (1H, dd, J=2.1 Hz, 5.1 Hz)

Synthesis Example 24

4-Hydroxy-1-(3-trifluoromethoxyphenyl)-3-(3-trifluoromethoxyphenylacetyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. To a suspension of the synthesized compound (806 mg, 2.5 mmol) in DMF (15 mL) was added sodium hydride (purity of about 60%, 220 mg, 5.5 mmol, 2.2 eq.), and the mixture was stirred until no more hydrogen was generated. Then, 3-trifluoromethoxyphenylacetyl chloride (3.0 mmol, 1.2 eq.) which had been previously prepared was added thereto, and the mixture was stirred at a room temperature for 1 hour. To the mixture was added water. The resulting mixture was acidified with hydrochloric acid, and the precipitate was separated by filtration and washed with water. The precipitate was purified by a flash column chromatography to give 4-hydroxy-1-(3-trifluoromethoxyphenyl)-3-(3-trifluoromethoxyphenylacetyl)-1,8-naphthyridin-2(1H)-one as a form of crystal (666 mg, yield 51%).

mp: 95-98° C.
$^1$H NMR (DMSO-$d_6$) δ: 4.61 (2H, s), 7.24-7.51 (8H, m), 7.68 (1H, t, J=8.1 Hz), 8.54 (1H, dd, J=1.9 Hz, 7.8 Hz), 8.60 (1H, dd, J=1.9 Hz, 4.6 Hz)

Synthesis Example 25

4-Hydroxy-1-(3-trifluoromethoxyphenyl)-3-(4-trifluoromethoxyphenylacetyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. To a suspension of the synthesized compound (967 mg, 3.0 mmol) in DMF (20 mL) was added sodium hydride (purity of about 60%, 264 mg, 6.6 mmol, 2.2 eq.), and the mixture was stirred until no more hydrogen was generated. Then, 4-trifluoromethoxyphenylacetyl chloride (3.6 mmol, 1.2 eq.) which had been previously prepared was added thereto with cooling in an ice bath, and the mixture was stirred at a room temperature for 1 hour. To the mixture was added water. The resulting mixture was acidified with hydrochloric acid, and the precipitate was separated by filtration and washed with water. The precipitate was purified by a flash column chromatography to give 4-hydroxy-1-(3-trifluoromethoxyphenyl)-3-(4-trifluoromethoxyphenylacetyl)-1,8-naphthyridin-2(1H)-one as a form of crystal (558 mg, yield 35%).

mp: 102-104° C.
$^1$H NMR (CDCl$_3$) δ: 4.62 (2H, s), 7.15-7.40 (8H, m), 7.59-7.65 (1H, m), 8.51-8.56 (2H, m)

Synthesis Example 26

4-Hydroxy-1-phenyl-3-phenylacetyl-1,7-naphthyridin-2(1H)-one

In accordance with a process described in JP-61-246183A or J. Med. Chem., 31, 2108 (1988), 4-hydroxy-1-phenyl-1,7-naphthyridin-2(1H)-one was synthesized. To a solution of the synthesized compound (263 mg, 1.1 mmol) in DMF (5 mL) was added sodium hydride (purity of about 60%, 97 mg, 2.4 mmol, 2.2 eq.), and the mixture was stirred until no more hydrogen was generated. Then, phenylacetyl chloride (175 µL, 1.3 mmol, 1.2 eq.) was added thereto, and the mixture was stirred at a room temperature for 1 hour. The step for adding the same amount of sodium hydride and the step for adding the same amount of phenylacetyl chloride were further conducted twice. To the mixture was added water. The resulting mixture was acidified with hydrochloric acid, and the precipitate was separated by filtration and washed with water. The precipitate was purified by a flash column chromatography to give 4-hydroxy-1-phenyl-3-phenylacetyl-1,7-naphthyridin-2(1H)-one as a form of crystal (186 mg, yield 47%).

mp: 216-219° C.
$^1$H NMR (DMSO-$d_6$) δ: 4.53 (2H, s), 7.24-7.31 (5H, m), 7.44 (2H, d, J=7.8 Hz), 7.60-7.70 (3H, m), 7.88 (1H, s), 8.00 (1H, d, J=5.1 Hz), 8.48 (1H, d, J=4.9 Hz)

Synthesis Example 27

4-Hydroxy-3-(2-methoxyphenylacetyl)-1-(3-trifluoromethoxyphenyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. The synthesized compound (967 mg, 3.0 mmol) was suspended in DMF (24 mL). To the suspension was added sodium hydride (purity of about 60%, 264 mg, 6.6 mmol, 2.2 eq.), and the mixture was stirred until no more hydrogen was generated. Then, 2-methoxyphenylacetyl chloride (3.6 mmol, 1.2 eq.) was added thereto, and the mixture was stirred at a room temperature for 1.5 hours. To the mixture was added water. The resulting mixture was acidified with hydrochloric acid, and the precipitate was separated by filtration and washed with water. The precipitate was purified by a flash column chromatography to give 4-hydroxy-3-(2-methoxyphenylacetyl)-1-(3-trifluoromethoxyphenyl)-1,8-naphthyridin-2(1H)-one as a form of crystal (940 mg, yield 67%).

mp: 60-74° C. (uncertain)
$^1$H NMR (CDCl$_3$) δ: 3.78 (3H, s), 4.59 (2H, s), 6.90-6.98 (2H, m), 7.11-7.39 (6H, m), 7.61 (1H, t, J=7.9 Hz), 8.52 (1H, dd, J=2.0 Hz, 7.9 Hz), 8.55 (1H, dd, J=2.0 Hz, 4.6 Hz)

Synthesis Example 28

3-(4-Fluorophenylacetyl)-4-hydroxy-1-(3-trifluoromethoxyphenyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. The synthesized compound (967 mg, 3.0 mmol) was suspended in DMF (24 mL)
To the suspension was added sodium hydride (purity of about 60%, 264 mg, 6.6 mmol, 2.2 eq.), and the mixture was stirred until no more hydrogen was generated. Then, 4-fluorophenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 3-(4-fluorophenylacetyl)-4-hydroxy-1-(3-trifluoromethoxyphenyl)-1,8-naphthyridin-2(1H)-one as a form of crystal (662 mg, yield 48%).

mp: 137-138° C.
$^1$H NMR (CDCl$_3$) δ: 4.58 (2H, s), 7.00 (2H, app-tt, 8.9 Hz, 2.3 Hz), 7.16-7.29 (5H, m), 7.37 (1H, app-quin. d, J=1.0 Hz, 8.6 Hz), 7.61 (1H, t, J=7.9 Hz), 8.51 (1H, dd, J=2.0 Hz, 7.9 Hz), 8.53 (1H, dd, J=2.0 Hz, 4.6 Hz)

Synthesis Example 29

3-(2-Chlorophenylacetyl)-4-hydroxy-1-(3-trifluoromethoxyphenyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. The synthesized compound (967 mg, 3.0 mmol) was suspended in DMF (24 mL) To the suspension was added sodium hydride (purity of about 60%, 264 mg, 6.6 mmol, 2.2 eq.), and the mixture was stirred until no more hydrogen was generated. Then, 2-chlorophenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(2-chlorophenylacetyl)-1-(3-trifluoromethoxyphenyl)-1,8-naphthyridin-2(1H)-one as a form of crystal (728 mg, yield 67%).

mp: 69-89° C. (uncertain)
$^1$H NMR (CDCl$_3$) δ: 4.74 (2H, s), 7.20-7.33 (6H, m), 7.36-7.46 (2H, m), 7.62 (1H, t, J=7.9 Hz), 8.54 (1H, dd, J=2.0 Hz, 7.9 Hz), 8.57 (1H, dd, J=2.0 Hz, 4.6 Hz)

Synthesis Example 30

4-Hydroxy-3-(2-methylphenylacetyl)-1-(3-trifluoromethoxyphenyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. The synthesized compound (967 mg, 3.0 mmol) was suspended in DMF (24 mL)
To the suspension was added sodium hydride (purity of about 60%, 264 mg, 6.6 mmol, 2.2 eq.), and the mixture was stirred until no more hydrogen was generated. Then, 2-methylphenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(2-methylphenylacetyl)-1-(3-trifluoromethoxyphenyl)-1,8-naphthyridin-2(1H)-one as a form of crystal (641 mg, yield 47%).

mp: 132-134° C.
$^1$H NMR (CDCl$_3$) δ: 2.25 (3H, s), 4.64 (2H, s), 7.10-7.29 (7H, m), 7.38 (1H, app-quin. d, J=1.0 Hz, 8.6 Hz), 7.62 (1H, t, J=8.2 Hz), 8.53 (1H, dd, J=2.0 Hz, 7.9 Hz), 8.56 (1H, dd, J=2.0 Hz, 4.6 Hz)

Synthesis Example 31

4-Hydroxy-3-(2-nitrophenylacetyl)-1-(3-trifluoromethoxyphenyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. The synthesized compound (967 mg, 3.0 mmol) was suspended in DMF (24 mL). To the suspension was added sodium hydride (purity of about 60%, 264 mg, 6.6 mmol, 2.2 eq.), and the mixture was stirred until no more hydrogen was generated. Then, 2-nitrophenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(2-nitrophenylacetyl)-1-(3-trifluoromethoxyphenyl)-1,8-naphthyridin-2(1H)-one as a form of crystal (490 mg, yield 34%).

mp: 188-190° C.

$^1$H NMR (CDCl$_3$) δ: 4.99-5.01 (2H, m), 7.20-7.21 (1H, m), 7.25 (1H, dd, J=4.6 Hz, 7.9 Hz), 7.28 (1H, ddd, J=1.0 Hz, 2.0 Hz, 7.9 Hz), 7.34 (1H, dd, J=1.6 Hz, 7.9 Hz), 7.38 (1H, app-quin. d, J=1.0 Hz, 8.6 Hz), 7.50 (1H, dt, J=1.6 Hz, 7.9 Hz), 7.61 (1H, d, J=7.9 Hz), 7.63 (1H, t, J=7.6 Hz), 8.18 (1H, dd, J=1.6 Hz, 7.9 Hz), 8.53 (1H, dd, J=2.0 Hz, 7.9 Hz), 8.57 (1H, dd, J=2.0 Hz, 4.6 Hz)

Synthesis Example 32

4-Hydroxy-3-(2-phenylpropionyl)-1-(3-trifluoromethoxyphenyl)-1,8-naphthyridin-2(1H)-one (i) In accordance with a process described in JP-61-246183A, 4-hydroxy-1-(3-trifluoromethoxyphenyl)-1,8-naphthyridin-2(1H)-one was synthesized. To a suspension of the synthesized compound (967 mg, 3.0 mmol) in DMF (24 mL) was added sodium hydride (purity of about 60%, 120 mg, 1.0 eq.). The mixture was stirred until no more hydrogen was generated, to obtain a solution. Then, 2-phenylpropionyl chloride (1.2 eq.) was added thereto, and the mixture was stirred at a room temperature for 1 hour. To the mixture was added a saturated sodium hydrogencarbonate aqueous solution, and the resulting precipitate was separated by filtration, washed with water, and dried to give 4-(2-phenylpropionyloxy)-1-(3-trifluoromethoxyphenyl)-1,8-naphthyridin-2(1H)-one as a form of crystal (1.14 g, yield 84%).

mp: 115-117° C.

$^1$H NMR (CDCl$_3$) δ: 1.70 (3H, d, J=7.3 Hz), 4.12 (1H, q, J=7.3 Hz), 6.70 (1H, s), 7.00 (1H, dd, J=4.6 Hz, 7.9 Hz), 7.13 (1H, brs), 7.21 (1H, ddd, J=1.0 Hz, 1.6 Hz, 7.9 Hz), 7.33 (1H, app-quin. d, J=1.0 Hz, 8.6 Hz), 7.37-7.45 (6H, m), 7.57 (1H, d, J=8.2 Hz), 8.39 (1H, dd, J=2.0 Hz, 4.6 Hz)

(ii) Dry toluene (24 mL) was added to 4-(2-phenylpropionyloxy)-1-(3-trifluoromethoxyphenyl)-1,8-naphthyridin-2(1H)-one (1.1 g, 2.4 mmol), triethylamine (249 mg, 2.5 mmol, 1 eq.), potassium cyanide (316 mg, 4.9 mmol, 2 eq.), and 18-crown-6 (128 mg), and the mixture was stirred at a room temperature overnight. Chloroform was added thereto. The insoluble residue was removed by using Celite, and the solvent of the resulting filtrate was distilled off. The resulting residue was purified by a flash column chromatography to give 4-hydroxy-3-(2-phenylpropionyl)-1-(3-trifluoromethoxyphenyl)-1,8-naphthyridin-2(1H)-one as a form of crystal (310 mg, yield 28%).

mp: 136-138° C.

$^1$H NMR (CDCl$_3$) δ: 1.54 (3H, d, J=7.6 Hz), 5.67 (1H, q, J=6.9 Hz), 7.17-7.41 (8H, m), 7.19 (1H, dd, J=4.9 Hz, 7.6 Hz), 7.58 (1H, t, J=7.9 Hz), 8.48 (1H, dd, J=2.0 Hz, 7.9 Hz), 8.50 (1H, dd, J=2.0 Hz, 4.9 Hz)

Synthesis Example 33

4-Hydroxy-3-(2-methoxyphenylacetyl)-1-(3-trifluoromethylphenyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (919 mg, 3.0 mmol) in DMF (24 mL) was added sodium hydride (purity of about 60%, 264 mg, 6.6 mmol, 2.2 eq.), and the mixture was stirred until no more hydrogen was generated. Then, 2-methoxyphenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(2-methoxyphenylacetyl)-1-(3-trifluoromethylphenyl)-1,8-naphthyridin-2(1H)-one as a form of crystal (533 mg, yield 39%).

mp: 166-167° C.

$^1$H NMR (CDCl$_3$) δ: 3.78 (3H, s), 4.58 (2H, s), 6.90-6.98 (2H, m), 7.13 (1H, dd, J=1.6 Hz, 7.3 Hz), 7.21-7.33 (2H, m), 7.50-7.53 (1H, m), 7.58 (1H, brs), 7.71 (1H, t, J=7.6 Hz), 7.75-7.79 (1H, m), 8.52 (1H, dd, J=2.0 Hz, 3.3 Hz) 8.55 (1H, s)

Synthesis Example 34

3-(4-Fluorophenylacetyl)-4-hydroxy-1-(3-trifluoromethylphenyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (918 mg, 3.0 mmol) in DMF (24 mL) was added sodium hydride (purity of about 60%, 264 mg, 6.6 mmol, 2.2 eq.), and the mixture was stirred until no more hydrogen was generated. Then, 4-fluorophenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 3-(4-fluorophenylacetyl)-4-hydroxy-1-(3-trifluoromethylphenyl)-1,8-naphthyridin-2(1H)-one as a form of crystal (650 mg, yield 49%).

mp: 133-134° C.

$^1$H NMR (CDCl$_3$) δ: 4.58 (2H, s), 7.02 (2H, app-tt, J=8.9 Hz, 2.3 Hz), 7.22-7.29 (3H, m), 7.46-7.50 (1H, m), 7.55 (1H, brs), 7.72 (1H, t, J=7.6 Hz), 7.76-7.79 (1H, m), 8.52 (1H, dd, J=2.0 Hz, 4.0 Hz) 8.54 (1H, s)

Synthesis Example 35

3-(2-Chlorophenylacetyl)-4-hydroxy-1-(3-trifluoromethylphenyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (918 mg, 3.0 mmol) in DMF (24 mL) was added sodium hydride (purity of about 60%, 264 mg, 6.6 mmol, 2.2 eq.), and the mixture was stirred until no more hydrogen was generated. Then, 2-chlorophenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 3-(2-chlorophenylacetyl)-4-hydroxy-1-(3-trifluoromethylphenyl)-1,8-naphthyridin-2(1H)-one as a form of crystal (752 mg, yield 55%).

mp: 73-84° C. (uncertain)

$^1$H NMR (CDCl$_3$) δ: 4.74 (2H, s), 7.20-7.33 (4H, m), 7.39-7.45 (1H, m), 7.50-7.54 (1H, m), 7.60 (1H, brs), 7.72 (1H, t, J=7.6 Hz), 7.76-7.80 (1H, m), 8.54 (1H, dd, J=1.6 Hz, 4.3 Hz) 8.56 (1H, s)

Synthesis Example 36

4-Hydroxy-3-(2-methylphenylacetyl)-1-(3-trifluoromethylphenyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (918 mg, 3.0 mmol) in DMF (24 mL) was added sodium hydride (purity of about 60%, 264 mg, 6.6 mmol, 2.2 eq.), and the mixture was stirred until no more hydrogen was generated. Then, 2-methylphenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(2-methylphenylacetyl)-1-(3-trifluoromethylphenyl)-1,8-naphthyridin-2(1H)-one as a form of crystal (610 mg, yield 46%).

mp: 150-152° C.

$^1$H NMR (CDCl$_3$) δ: 2.25 (3H, s), 4.64 (2H, s), 7.10-7.27 (5H, m), 7.50-7.54 (1H, m), 7.58 (1H, brs), 7.72 (1H, t, J=7.6 Hz), 7.76-7.80 (1H, m), 8.53 (1H, dd, J=2.0 Hz, 4.3 Hz) 8.55 (1H, s)

Synthesis Example 37

4-Hydroxy-3-(2-nitrophenylacetyl)-1-(3-trifluoromethylphenyl)-1,8-naphthyridin-2(1H)-one In accordance with a process described in JP-61-246183A or J. Med. Chem., 31, 2108 (1988), 4-hydroxy-1-(3-trifluoromethylphenyl)-1,8-naphthyridin-2(1H)-one was synthesized. To a suspension of the synthesized compound (919 mg, 3.0 mmol) in DMF (24 mL) was added sodium hydride (purity of about 60%, 264 mg, 6.6 mmol, 2.2 eq.), and the mixture was stirred until no more hydrogen was generated. Then, 2-nitrophenylacetyl chloride (3.6 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(2-nitrophenylacetyl)-1-(3-trifluoromethylphenyl)-1,8-naphthyridin-2(1H)-one as a form of crystal (677 mg, yield 48%).

mp: 179-181° C.

$^1$H NMR (CDCl$_3$) δ: 4.91-5.08 (2H, m), 7.26 (1H, dd, J=4.6 Hz, 7.9 Hz), 7.34 (1H, dd, J=1.3 Hz, 7.6 Hz), 7.47-7.80 (6H, m), 8.18 (1H, dd, J=1.6 Hz, 7.9 Hz), 8.53 (1H, dd, J=2.0 Hz, 7.9 Hz), 8.56 (1H, dd, J=2.0 Hz, 4.6 Hz)

Synthesis Example 38

4-Hydroxy-3-(2-phenylpropionyl)-1-(3-trifluoromethylphenyl)-1,8-naphthyridin-2(1H)-one (i) In accordance with a process described in JP-61-246183A, 4-hydroxy-1-(3-trifluoromethylphenyl)-1,8-naphthyridin-2(1H)-one was synthesized. To a suspension of the synthesized compound (919 mg, 3.0 mmol) in DMF (24 mL) was added sodium hydride (purity of about 60%, 120 mg, 3.0 mmol, 1.0 eq.). The mixture was stirred until no more hydrogen was generated, to obtain a solution. Then, 2-phenylpropionyl chloride (1.2 eq.) was added thereto, and the mixture was stirred at a room temperature for 1 hour. To the mixture was added a saturated sodium hydrogencarbonate aqueous solution, and the resulting precipitate was separated by filtration, washed with water, and dried to give 4-(2-phenylpropionyloxy)-1-(3-trifluoromethylphenyl)-1,8-naphthyridin-2(1H)-one as a form of crystal (1.00 g, yield 76%).

mp: 42-57° C. (uncertain)

$^1$H NMR (CDCl$_3$) δ: 1.70 (3H, d, J=7.3 Hz), 4.12 (1H, q, J=7.3 Hz), 6.71 (1H, s), 7.01 (1H, dd, J=4.9 Hz, 7.9 Hz), 7.32-7.48 (7H, m), 7.53 (1H, br), 7.67 (1H, t, J=7.6 Hz), 7.72-7.75 (1H, m), 8.37 (1H, dd, J=2.0 Hz, 4.9 Hz)

(ii) Dry toluene (20 mL) was added to 4-(2-phenylpropionyloxy)-1-(3-trifluoromethylphenyl)-1,8-naphthyridin-2(1H)-one (890 mg, 2.0 mmol), triethylamine (209 mg, 2.1 mmol, 1 eq.), potassium cyanide (266 mg, 4.1 mmol, 2 eq.), and 18-crown-6 (107 mg), and the mixture was stirred at a room temperature for 7.5 hours. Chloroform was added thereto. The insoluble residue was removed by using Celite, and the solvent of the resulting filtrate was distilled off. The resulting residue was purified by a flash column chromatography to give 4-hydroxy-3-(2-phenylpropionyl)-1-(3-trifluoromethylphenyl)-1,8-naphthyridin-2(1H)-one as a form of crystal (150 mg, yield 17%).

mp: 200-201° C.

$^1$H NMR (CDCl$_3$) δ: 1.54 (3H, d, J=6.9 Hz), 5.65 (1H, q, J=6.9 Hz), 7.17-7.51 (8H, m), 7.68 (1H, t, J=7.6 Hz), 7.75 (1H, d, J=7.9Hz), 8.47 (1H, s), 8.50 (1H, dd, J=2.0 Hz, 4.6 Hz)

Synthesis Example 39

4-Hydroxy-1-phenyl-3-(2-phenylbutyryl)-1,8-naphthyridin-2(1H)-one (i) In accordance with a process described in JP-61-246183A, 4-hydroxy-1-phenyl-1,8-naphthyridin-2(1H)-one was synthesized. To a suspension of the synthesized compound (1.19 g, 5.0 mmol) in DMF (40 mL) was added sodium hydride (purity of about 60%, 200 mg, 5.0 mmol, 1.0 eq.). The mixture was stirred until no more hydrogen was generated, to obtain a solution. Then, 2-phenylbutyryl chloride (0.92 mL, 5.5 mmol, 1.1 eq.) was added thereto, and the mixture was stirred at a room temperature for 1 hour. To the mixture was added a saturated sodium hydrogencarbonate aqueous solution, and the resulting precipitate was separated by filtration, washed with water, and dried to give 1-phenyl-4-(2-phenylbutyryloxy)-1,8-naphthyridin-2(1H)-one as a form of crystal (1.63 g, yield 85%).

mp: 166-168° C.

$^1$H NMR (CDCl$_3$) δ: 1.04 (3H, t, J=7.6 Hz), 1.92-20.8 (1H, m), 2.22-2.38 (1H, m), 3.85 (1H, t, J=7.6 Hz), 6.68 (1H, s), 6.98 (1H, dd, J=4.6 Hz, 7.9 Hz), 7.23-7.26 (2H, m), 7.33-7.59 (9H, m), 8.40 (1H, dd, J=1.6 Hz, 4.6 Hz)

(ii) Dry toluene (40 mL) was added to 1-phenyl-4-(2-phenylbutyryloxy)-1,8-naphthyridin-2(1H)-one (1.54 g, 4.0 mmol), triethylamine (407 mg, 4.0 mmol, 1 eq.), potassium cyanide (528 mg, 8.1 mmol, 2 eq.), and 18-crown-6 (211 mg), and the mixture was stirred at a room temperature overnight. Chloroform was added thereto. The insoluble residue was removed by using Celite, and the solvent of the resulting filtrate was distilled off. The resulting residue was purified by a flash column chromatography to give 4-hydroxy-1-phenyl-3-(2-phenylbutyryl)-1,8-naphthyridin-2(1H)-one as a form of crystal (123 mg, yield 8%).

mp: 134-135° C.

$^1$H NMR (CDCl$_3$) δ: 0.87 (3H, d, J=7.6 Hz), 1.79-1.95 (1H, m), 2.13-2.26 (1H, m), 5.56-5.61 (1H, m), 7.15 (1H, dd, J=4.6 Hz, 7.9 Hz), 7.18-7.33 (5H, m), 7.41-7.61 (5H, m), 8.47 (1H, dd, J=2.0 Hz, 7.9 Hz), 8.50 (1H, dd, J=2.0 Hz, 4.6 Hz)

Synthesis Example 40

4-Hydroxy-1-phenyl-3-(tetrahydro-2H-pyran-4-ylacetyl)-1,8-naphthyridin-2(1H)-one (i) In accordance with a process described in JP-61-246183A, 4-hydroxy-1-phenyl-1,8-naphthyridin-2(1H)-one was synthesized. To a suspension of the synthesized compound (715 mg, 3.0 mmol) in DMF (20 mL) was added sodium hydride (purity of about 60%, 120 mg, 3.0 mmol, 1.0 eq.). The mixture was stirred until no more hydrogen was generated, to obtain a solution. Then, tetrahydro-2H-pyran-4-ylacetyl chloride (1.2 eq.) was added thereto, and the mixture was stirred at a room temperature for 1 hour. To the mixture was added a saturated sodium hydrogencarbonate aqueous solution, and the resulting precipitate was separated by filtration, washed with water, and dried to give 1-phenyl-4-(tetrahydro-2H-pyran-4-ylacetoxy)-1,8-naphthyridin-2(1H)-one as a form of crystal (738 mg, yield 67%).

mp: 169-171° C.

$^1$H NMR (CDCl$_3$) δ: 1.42-1.56 (2H, m), 1.75-1.82 (2H, m), 2.14-2.31 (1H, m), 2.68 (2H, d, J=6.9 Hz), 3.43-3.52 (2H, app-dt, J=2.0 Hz, 11.9 Hz), 3.99-4.05 (2H, m), 6.78 (1H, s), 7.18 (1H, dd, J=4.6 Hz, 7.9 Hz), 7.26-7.30 (2H, m), 7.47-7.62 (3H, m), 7.97 (1H, dd, J=2.0 Hz, 7.9 Hz), 8.49 (1H, dd, J=1.6 Hz, 4.6 Hz)

(ii) Dry toluene (20 mL) was added to 1-phenyl-4-(tetrahydro-2H-pyran-4-ylacetoxy)-1,8-naphthyridin-2(1H)-one (691 mg, 1.9 mmol), triethylamine (192 mg, 1.9 mmol, 1 eq.), potassium cyanide (249 mg, 3.8 mmol, 2 eq.), and 18-crown-6 (100 mg), and the mixture was stirred at a room temperature overnight. Chloroform was added thereto. The insoluble residue was removed by using Celite, and the solvent of the resulting filtrate was distilled off. The resulting residue was purified by a flash column chromatography to give 4-hydroxy-1-phenyl-3-(tetrahydro-2H-pyran-4-ylacetyl)-1,8-naphthyridin-2(1H)-one as a form of crystal (137 mg, yield 20%).

mp: 198-203° C.

$^1$H NMR (CDCl$_3$) δ: 1.31-1.46 (2H, m), 1.66-1.72 (2H, m), 2.17-2.33 (1H, m), 3.24 (2H, d, J=6.9 Hz), 3.39-3.48 (2H, app-dt, J=2.0 Hz, 11.9 Hz), 3.91-3.97 (2H, m), 7.21 (1H, dd, J=4.9 Hz, 7.9 Hz), 7.24-7.33 (2H, m), 7.47-7.62 (3H, m), 8.53 (1H, dd, J=2.0 Hz, 7.9 Hz), 8.55 (1H, dd, J=2.0 Hz, 4.6 Hz)

Synthesis Example 41

4-Hydroxy-3-(2-thienylacetyl)-1-(3-trifluoromethoxyphenyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. The synthesized compound (645 mg, 2.0 mmol) was suspended in DMF (10 mL) To the suspension was added sodium hydride (purity of about 60%, 176 mg, 4.4 mmol, 2.2 eq.), and the mixture was stirred until no more hydrogen was generated. Then, 2-thienylacetyl chloride (2.4 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(2-thienylacetyl)-1-(3-trifluoromethoxyphenyl)-1,8-naphthyridin-2(1H)-one as a form of crystal (195 mg, yield 22%).

mp: 55-58° C.

$^1$H NMR (DMSO-d$_6$) δ: 4.75 (2H, S), 6.99 (1H, d, J=3.2 Hz), 7.38-7.51 (5H, m), 7.68 (1H, t, J=8.1 Hz), 8.52-8.60 (2H, m)

Synthesis Example 42

4-Hydroxy-3-(3-thienylacetyl)-1-(3-trifluoromethoxyphenyl)-1,8-naphthyridin-2(1H)-one In accordance with a process described in JP-61-246183A or J. Med. Chem., 31, 2108 (1988), 4-hydroxy-1-(3-trifluoromethoxyphenyl)-1,8-naphthyridin-2(1H)-one was synthesized. The synthesized compound (645 mg, 2.0 mmol) was suspended in DMF (10 mL). To the suspension was added sodium hydride (purity of about 60%, 176 mg, 4.4 mmol, 2.2 eq.), and the mixture was stirred until no more hydrogen was generated. Then, 3-thienylacetyl chloride (2.4 mmol, 1.2 eq.) was added thereto, and the mixture was stirred at a room temperature for 2 hours. To the mixture was added water. The resulting mixture was acidified with hydrochloric acid, and the precipitate was separated by filtration and washed with water. The precipitate was purified by a flash column chromatography to give 4-hydroxy-3-(3-thienylacetyl)-1-(3-trifluoromethoxyphenyl)-1,8-naphthyridin-2(1H)-one as a form of crystal (84 mg, yield 9%).

mp: 116-119° C.

$^1$H NMR (DMSO-d$_6$) δ: 4.53 (2H, s), 7.05 (1H, d, J=4.9 Hz), 7.32-7.49 (6H, m), 7.68 (1H, t, J=8.1 Hz), 8.52 (2H, m)

(2) Synthesis of compound of formula (1)

Example 1

3-Benzyl-5-(3-trifluoromethoxyphenyl)-1H-pyrazolo[4,3-c][1,8]-naphthyridin-4(5H)-one To a suspension of 4-hydroxy-3-phenylacetyl-1-(3-trifluoromethoxyphenyl)-1,8-naphthyridin-2(1H)-one (220 mg, 0.50 mmol) produced in Synthesis Example 1 in DMF (4 mL) was added hydrazine monohydrate (purity of 80%, 80 µL), and the mixture was stirred at 100 to 110° C. for 3 hours. To the reaction solution was added water. The resulting precipitate was separated by filtration, washed with water, and dried to give 3-benzyl-5-(3-trifluoromethoxyphenyl)-1H-pyrazolo[4,3-c][1,8]-naphthyridin-4(5H)-one as a form of crystal (204 mg, yield 94%).

mp: 249-251° C./DMF-H$_2$O $^1$H NMR (DMSO-d$_6$) δ: 4.36 (2H, d, J=1.0), 7.15-7.38 (7H, m), 7.42 (1H, s), 7.46 (1H, app-quin. d, J=1.0 Hz, 8.2 Hz), 7.65 (1H, t, J=8.2 Hz), 8.37 (1H, dd, J=2.0 Hz, 4.6 Hz), 8.51 (1H, dd, J=2.0 Hz, 7.9 Hz), 13-15 (1H, br)

Example 2

3-Benzyl-5-(3-trifluoromethylphenyl)-1H-pyrazolo[4,3-c][1,8]-naphthyridin-4(5H)-one To a suspension of 4-hydroxy-3-phenylacetyl-1-(3-trifluoromethylphenyl)-1,8-naphthyridine-2(1H)-one (212 mg, 0.50 mmol) produced in Synthesis Example 2 in DMF (4 mL) was added hydrazine monohydrate (purity of 80%, 80 μL), and the mixture was stirred at 100 to 110° C. for 3 hours. To the reaction solution was added water. The resulting precipitate was separated by filtration, washed with water, and dried to give 3-benzyl-5-(3-trifluoromethylphenyl)-1H-pyrazolo[4,3-c][1,8]-naphthyridin-4(5H)-one as a form of crystal (172 mg, yield 82%).

mp: 226-228° C./DMF-H$_2$O $^1$H NMR (DMSO-d$_6$) δ: 4.36 (2H, s), 7.15-7.37 (6H, m), 7.62-7.66 (1H, m), 7.73-7.84 (3H, m), 8.36 (1H, dd, J=2.0 Hz, 4.6 Hz), 8.51 (1H, dd, J=2.0 Hz, 7.9 Hz), 13-15 (1H, br)

Example 3

3-Benzyl-7-methyl-5-phenyl-1H-pyrazolo[4,3-c][1,8]-naphthyridin-4(5H)-one

To a suspension of 4-hydroxy-7-methyl-1-phenyl-3-phenylacetyl-1,8-naphthyridin-2(1H)-one (370 mg, 1.0 mmol) produced in Synthesis Example 3 in DMF (8 mL) was added hydrazine monohydrate (purity of 80%, 160 μL), and the mixture was stirred at 100 to 110° C. for 2 hours. To the reaction solution was added a sodium hydrogencarbonate aqueous solution. The resulting precipitate was separated by filtration, washed with water, and dried to give 3-benzyl-7-methyl-5-phenyl-1H-pyrazolo [4,3-c][1,8]-naphthyridin-4(5H)-one as a form of crystal (281 mg, yield 83%).

mp: 300-302° C./DMF-H$_2$O $^1$H NMR (DMSO-d$_6$) δ: 2.30 (3H, s), 4.34 (2H, s), 7.14-7.36 (8H, m), 7.40-7.54 (3H, m), 8.37 (1H, d, J=7.9 Hz), 14 (1H, br)

Example 4

5-Phenyl-3-(2-trifluoromethoxybenzyl)-1H-pyrazolo[4,3-c][1,8]naphthyridin-4(5H)-one In accordance with a process described in JP-61-246183A, 4-hydroxy-1-phenyl-1,8-naphthyridin-2(1H)-one was synthesized. To a suspension of the synthesized compound (477 mg, 2.0 mmol) in DMF (10 mL) was added sodium hydride (purity of about 60%, 200 mg, 5.0 mmol, 2.5 eq.), and the mixture was stirred until no more hydrogen was generated. Then, 2-trifluoromethoxyphenylacetyl chloride (1.9 eq.) was added thereto, and the mixture was stirred at a room temperature for 20 minutes. To the mixture was added water. The resulting syrupy substance was solidified with water, methanol; and isopropyl ether. The resulting solid was separated by filtration, washed with water, and suspended in DMF (8 mL). To the suspension was added hydrazine monohydrate (purity of 80%, 224 μL), and the mixture was stirred at 100 to 110° C. for 3 hours. Hydrazine monohydrate (purity of 80%, 100 μL) was added thereto, and the mixture was stirred at 100 to 110° C. for 1 hour. To the reaction solution was added water. The resulting precipitate was separated by filtration and dried to give 5-phenyl-3-(2-trifluoromethoxybenzyl)-1H-pyrazolo[4,3-c][1,8]naphthyridin-4(5H)-one (520 mg, yield 60%).

mp: 275° C. (dec.)/DMF-H$_2$O $^1$H NMR (DMSO-d$_6$) δ: 4.43 (2H, s), 7.23-7.54 (10H, m), 8.36-8.39 (1H, dd, J=2.0 Hz, 7.9 Hz), 8.50-8.54 (1H, dd, J=2.0 Hz, 4.6 Hz), 14.14 (1H, s)

Example 5

5-Phenyl-3-(3-trifluoromethoxybenzyl)-1H-pyrazolo[4,3-c][1,8]naphthyridin-4(5H)-one In accordance with a process described in JP-61-246183A, 4-hydroxy-1-phenyl-1,8-naphthyridin-2(1H)-one was synthesized. To a suspension of the synthesized compound (447 mg, 1.9 mmol) in DMF (10 mL) was added sodium hydride (purity of about 60%, 220 mg, 5.5 mmol, 2.9 eq.), and the mixture was stirred until no more hydrogen was generated. Then, 3-trifluoromethoxyphenylacetyl chloride (1.2 eq.) was added thereto, and the mixture was stirred at a room temperature for 3 hours. To the mixture was added water and further added a saturated sodium hydrogencarbonate solution. The resulting mixture was extracted with chloroform. The extract was dried over anhydrous magnesium sulfate, and chloroform was distilled off. To the resulting product was added DMF (8 mL) and further added hydrazine monohydrate (purity of 80%, 224 μL). The mixture was stirred at 100 to 110° C. overnight. To the reaction solution were added water and concentrated hydrochloric acid, and the resulting precipitate was separated by filtration and dried to give 5-phenyl-3-(3-trifluoromethoxybenzyl)-1H-pyrazolo[4,3-c][1,8]naphthyridin-4(5H)-one (157 mg, yield 19%).

mp: 253-254° C./DMF-H$_2$O $^1$H NMR (DMSO-d$_6$) δ: 4.41 (2H, s), 7.24-7.52 (10H, m), 8.36-8.38 (1H, m), 8.49-8.52 (1H, m), 14.22 (1H, s)

Example 6

5-Phenyl-3-(4-trifluoromethoxybenzyl)-1H-pyrazolo[4,3-c][1,8]naphthyridin-4(5H)-one To 4-hydroxy-1-phenyl-3-(4-trifluorophenylacetyl)-1,8-naphthyridine-2(1H)-one (206 mg, 0.47 mmol) produced in Synthesis Example 4 was added DMF (2 mL) to prepare a suspension. Hydrazine monohydrate (purity of 80%, 56 μL) was added thereto, and the mixture was stirred at 100 to 110° C. overnight. To the reaction solution was added water. The resulting precipitate was separated by filtration and dried to give 5-phenyl-3-(4-trifluoromethoxybenzyl)-1H-pyrazolo[4,3-c][1,8]naphthyridin-4(5H)-one (193 mg, yield 94%).

mp: 216-218° C./DMF-H$_2$O $^1$H NMR (DMSO-d$_6$) δ: 4.39 (2H, s), 7.25-7.36 (5H, m), 7.44-7.52 (5H, m), 8.36-8.38 (1H, dd, J=1.7 Hz, 4.9 Hz), 8.49-8.52 (1H, dd, J=1.7 Hz, 7.6 Hz), 14.22 (1H, s)

Example 7

5-Phenyl-3-(4-trifluoromethylbenzyl)-1H-pyrazolo[4,3-c][1,8]naphthyridin-4(5H)-one In accordance with a process described in JP-61-246183A, 4-hydroxy-1-phenyl-1,8-naphthyridin-2(1H)-one was synthesized. To a suspension of the synthesized compound (953 mg, 4.0 mmol) in DMF (32 mL) was added sodium hydride (purity of about 60%, 352 mg, 8.8 mmol, 2.2 eq.), and the mixture was stirred at a room temperature for 1 hour. Then, 4-trifluoromethylphenylacetyl chloride (4.8 mmol, 1.2 eq.) was added there to with cooling in an ice bath, and the mixture was stirred at a room temperature for 1.5 hours. To the mixture was added water. The resulting mixture was acidified with hydrochloric acid, and then the resulting precipitate was separated by filtration and suspended in DMF (30 mL) without purification. To the suspension was added hydrazine monohydrate (purity of 80%, 0.64 mL), and the mixture was stirred at 100 to 110° C. for 4 hours. To the reaction solution was added water, and the resulting precipitate was separated by filtration and dried to give 5-phenyl-3-(4-trifluoromethylbenzyl)-1H-pyrazolo[4,3-c][1,8]naphthyridin-4(5H)-one as a form of crystal (547 mg, yield 33%).

mp: 216-219° C.

$^1$H NMR (DMSO-d$_6$) δ: 4.45 (2H, s), 7.23-7.28 (2H, m), 7.31-7.36 (1H, dd, J=4.8 Hz, 7.8 Hz), 7.40-7.67 (7H, m), 8.35-8.38 (1H, dd, J=1.8 Hz, 4.8 Hz), 8.49-8.53 (1H, dd, J=1.8 Hz, 7.8 Hz)

Example 8

5-Phenyl-3-(2-trifluoromethylbenzyl)-1H-pyrazolo[4,3-c][1,8]naphthyridin-4(5H)-one A mixture of 4-hydroxy-1-phenyl-3-(2-trifluoromethylphenylacetyl)-1,8-naphthyridin-2(1H)-one (647 mg, 1.52 mmol) produced in Synthesis Example 5, DMF (10 mL), and hydrazine monohydrate (purity of 80%, 0.27 mL) was stirred at 100 to 110° C. for 4.5 hours. Then, water was added to the reaction solution. The resulting precipitate was separated by filtration and dried to give 5-phenyl-3-(2-trifluoromethylbenzyl)-1H-pyrazolo[4,3-c][1,8]naphthyridin-4(5H)-one as a form of crystal (486 mg, yield 76%).

mp: 292-294° C.

$^1$H NMR (DMSO-d$_6$) δ: 4.57 (2H, s), 7.24-7.28 (3H, m), 7.34-7.39 (1H, dd, J=4.8 Hz, 7.8 Hz), 7.40-7.59 (5H, m), 7.72-7.75 (1H, app-d, J=8.2 Hz), 8.38-8.40 (1H, dd, J=1.8 Hz, 4.8 Hz), 8.52-8.55 (1H, dd, J=1.8 Hz, 7.8 Hz)

Example 9

5-Phenyl-3-(3-trifluoromethylbenzyl)-1H-pyrazolo[4,3-c][1,8]naphthyridin-4(5H)-one A mixture of 4-hydroxy-1-phenyl-3-(3-trifluoromethylphenylacetyl)-1,8-naphthyridine-2(1H)-one (882 mg, 2.08 mmol) produced in Synthesis Example 6, DMF (15 mL), and hydrazine monohydrate (purity of 80%, 0.37 mL) was stirred at 100 to 110° C. for 4.5 hours. Then, water was added to the reaction solution. The resulting precipitate was separated by filtration and dried to give 5-phenyl-3-(3-trifluoromethylbenzyl)-1H-pyrazolo[4,3-c][1,8]naphthyridin-4(5H)-one as a form of crystal (598 mg, yield 68%).

mp: 303-305° C.

$^1$H NMR (DMSO-d$_6$) δ: 4.46 (2H, s), 7.24-7.28 (2H, m), 7.32-7.37 (1H, dd, J=5.0 Hz, 7.8 Hz), 7.41-7.65 (6H, m), 7.71 (1H, s), 8.36-8.38 (1H, dd, J=1.7 Hz, 5.0 Hz), 8.48-8.52 (1H, dd, J=1.7 Hz, 7.8 Hz)

Example 10

3-(Methoxymethyl)-5-phenyl-1H-pyrazolo[4,3-c][1,8]naphthyridin-4(5H)-one

Dry toluene (20 mL) was added to 4-methoxyacetoxy-1-phenyl-1,8-naphthyridine-2(1H)-one (775 mg, 2.5 mmol) produced in Synthesis Example 7, triethylamine (253 mg, 2.5 mmol, 1 eq.), potassium cyanide (326 mg, 5.0 mmol, 2 eq.), and 18-crown-6 (125 mg), and the mixture was stirred at a room temperature for 3 days. Chloroform was added thereto. The mixture was stirred, and the insoluble residue was separated by filtration. The insoluble residue was dissolved in water, and the solution was washed with chloroform. The chloroform layers were combined and washed with water. The solvent was distilled off, and the resulting residue (630 mg, 2.0 mmol) was suspended in DMF (8 mL). To the suspension was added hydrazine monohydrate (purity of 80%, 224 μL), and the mixture was stirred at 100 to 110° C. overnight. To the reaction solution was added water. The resulting precipitate was separated by filtration, recrystallized from DMF, methanol, and water, and then dried to give 3-(methoxymethyl)-5-phenyl-1H-pyrazolo[4,3-c][1,8]naphthyridin-4(5H)-one (191 mg, yield 25%).

mp: 263-265° C./DMF-MeOH—H$_2$O $^1$H NMR (DMSO-d$_6$) δ: 4.78 (2H, s), 7.29-7.55 (6H, m), 8.37-8.41 (1H, m), 8.51-8.54 (1H, m), 14.30 (1H, s)

Example 11

5-Phenyl-3-(1-phenylethyl)-1H-pyrazolo[4,3-c][1,8]naphthyridin-4(5H)-one

To a suspension of 4-hydroxy-1-phenyl-3-(2-phenylpropionyl)-1,8-naphthyridin-2(1H)-one (370 mg, 1.0 mmol) produced in Synthesis Example 8 in DMF (8 mL) was added hydrazine monohydrate (purity of 80%, 160 μL), and the mixture was stirred at 100 to 110° C. for 3 hours. To the reaction solution was added water. The resulting precipitate was separated by filtration, washed with water, and dried to give 5-phenyl-3-(1-phenylethyl)-1H-pyrazolo[4,3-c][1,8]naphthyridin-4(5H)-one as a form of crystal (306 mg, yield 84%).

mp: 267-268° C./DMF-H$_2$O $^1$H NMR (DMSO-d$_6$) δ: 1.71 (3H, d, J=7.3 Hz), 4.95 (1H, q, J=7.3 Hz), 7.13-7.53 (11H, m), 8.34 (1H, dd, J=1.7 Hz, 4.6 Hz), 8.51 (1H, dd, J=1.7 Hz, 7.9 Hz), 14.14 (1H, br)

Example 12

5-Phenyl-3-(6-phenylhexyl)-1H-pyrazolo[4,3-c][1,8]naphthyridin-4(5H)-one

A mixture of 4-hydroxy-1-phenyl-3-(7-phenylheptanoyl)-1,8-naphthyridin-2(1H)-one (500 mg, 1.17 mmol) produced in Synthesis Example 9, DMF (12 mL), hydrazine monohydrate (purity of 80%, 0.19 mL) was stirred at 100 to 110° C. for 3 hours. Then, a sodium hydrogencarbonate aqueous solution and water were added to the reaction solution. The resulting precipitate was separated by filtration and dried to give 5-phenyl-3-(6-phenylhexyl)-1H-pyrazolo[4,3-c][1,8]naphthyridin-4(5H)-one as a form of crystal (475 mg, yield 96%).

mp: 150-151° C.

$^1$H NMR (DMSO-d$_6$) δ: 1.32-1.34 (4H, m), 1.49-1.60 (2H, m), 1.66-1.77 (2H, m), 2.51-2.56 (2H, m), 2.94-3.00 (2H, t, J=7.6 Hz), 7.11-7.26 (7H, m), 7.28-7.33 (1H, dd, J=4.6 Hz, 7.6 Hz), 7.40-7.54 (3H, m), 8.33-8.35 (1H, dd, J=1.6 Hz, 4.6 Hz), 8.47-8.50 (1H, dd, J=1.6 Hz, 7.6 Hz), 13.95 (1H, br)

Example 13

3-Cyclohexylmethyl-5-phenyl-1H-pyrazolo[4,3-c][1,8]naphthyridin-4(5H)-one

A mixture of 3-cyclohexylacetyl-4-hydroxy-1-phenyl-1,8-naphthyridin-2(1H)-one (500 mg, 1.38 mmol) produced in Synthesis Example 10, DMF (14 mL), hydrazine monohydrate (purity of 80%, 0.22 mL) was stirred at 100 to 110° C. for 4 hours. Then, a sodium hydrogencarbonate aqueous solution and water were added to the reaction solution. The resulting precipitate was separated by filtration and dried to give 3-cyclohexylmethyl-5-phenyl-1H-pyrazolo[4,3-c][1,8]naphthyridin-4(5H)-one as a form of crystal (451 mg, yield 91%).

mp: 280-281° C.

$^1$H NMR (DMSO-$d_6$) δ: 0.91-1.23 (5H, m), 1.60-1.81 (6H, m), 2.86-2.89 (2H, d, J=7.3 Hz), 7.24-7.33 (3H, m), 7.40-7.54 (3H, m), 8.32-8.35 (1H, dd, J=1.3 Hz, 4.6 Hz), 8.47-8.50 (1H, dd, J=1.3 Hz, 7.6 Hz), 13.93 (1H, br)

Example 14

5-Phenyl-3-(3,3,3-trifluoropropyl)-1H-pyrazolo[4,3-c][1,8]naphthyridin-4(5H)-one A mixture of 4-hydroxy-1-phenyl-3-(4,4,4-trifluorobutyryl)-1,8-naphthyridin-2(1H)-one (65.4 mg, 0.18 mmol) produced in Synthesis Example 11, DMF (3 mL), hydrazine monohydrate (purity of 80%, 30 μL) was stirred at 100 to 110° C. for 6 hours. Then, a sodium hydrogencarbonate aqueous solution and water were added to the reaction solution. The resulting precipitate was separated by filtration and dried to give 5-phenyl-3-(3,3,3-trifluoropropyl)-1H-pyrazolo[4,3-c][1,8]naphthyridin-4(5H)-one as a form of crystal (37.5 mg, yield 58%).

mp: 272-274° C.

$^1$H NMR (DMSO-$d_6$) δ: 2.66-2.87 (2H, m), 3.13-3.27 (2H, m), 7.24-7.30 (2H, m), 7.34-7.39 (1H, dd, J=4.9 Hz, 7.6 Hz), 7.43-7.53 (3H, m), 8.31-8.40 (1H, m), 8.48-8.51 (1H, dd, J=1.7 Hz, 7.6 Hz), 14.05-14.16 (1H, m)

Example 15

3-Benzyl-5-phenyl-1H-pyrazolo[4,3-c][1,6]naphthyridin-4(5H)-one

To a suspension of 4-hydroxy-1-phenyl-3-phenylacetyl-1,6-naphthyridin-2(1H)-one (42 mg, 0.12 mmol) produced in Synthesis Example 12 in DMF (3 mL) was added hydrazine monohydrate (purity of 80%, 19 μL), and the mixture was stirred at 100 to 110° C. overnight. To the reaction solution was added a sodium hydrogencarbonate aqueous solution. The resulting precipitate was separated by filtration and dried to give 3-benzyl-5-phenyl-1H-pyrazolo[4,3-c][1,6]naphthyridin-4(5H)-one as a form of crystal (11 mg, yield 25%).

mp: 284-287° C.

$^1$H NMR (DMSO-$d_6$) δ: 4.35 (2H, brs), 6.41-6.43 (1H, app-d, J=4.9 Hz), 7.18-7.39 (7H, m), 7.55-7.66 (3H, m), 8.37-8.39 (1H, app-d, J=5.6 Hz), 9.28 (1H, s), 14.20 (1H, brs)

Example 16

3-Benzyl-5-phenyl-1H-pyrazolo[4,3-c]quinolin-4(5H)-one

To a suspension of 4-hydroxy-1-phenyl-3-phenylacetyl-quinolin-2(1H)-one (255 mg, 0.72 mmol) produced in Synthesis Example 13 in DMF (7 mL) was added hydrazine monohydrate (purity of 80%, 0.12 mL), and the mixture was stirred at 100 to 110° C. for 4 hours. To the reaction solution was added a sodium hydrogencarbonate aqueous solution. The resulting precipitate was separated by filtration and dried to give 3-benzyl-5-phenyl-1H-pyrazolo[4,3-c]quinolin-4(5H)-one as a form of crystal (177 mg, yield 70%).

mp: 255-257° C.

$^1$H NMR (DMSO-$d_6$) δ: 4.36 (2H, s), 6.51-6.55 (1H, dd, J=1.0 Hz, 8.2 Hz), 7.12-7.36 (9H, m), 7.49-7.64 (3H, m), 8.13-8.17 (1H, dd, J=1.7 Hz, 7.6 Hz), 13.76 (1H, br)

Example 17

3-(2-Trifluoromethylbenzyl)-5-(3-trifluoromethylphenyl)-1H-pyrazolo[4,3-c][1,8]naphthyridin-4(5H)-one To a suspension of 4-hydroxy-1-(3-trifluoromethylphenyl)-3-(2-trifluoromethylphenylacetyl)-1,8-naphthyridin-2(1H)-one (740 mg, 1.5 mmol) produced in Synthesis Example 14 in DMF (5 mL) was added hydrazine monohydrate (purity of 80%, 291 μL), and the mixture was stirred at 100 to 110° C. for 1 hour. To the reaction solution was added a sodium hydrogencarbonate aqueous solution. The resulting precipitate was separated by filtration, recrystallized from ethanol, and dried to give 3-(2-trifluoromethylbenzyl)-5-(3-trifluoromethylphenyl)-1H-pyrazolo[4,3-c][1,8]naphthyridin-4(5H)-one (489 mg, yield 67%).

mp: 260-264° C./EtOH (ethanol)

$^1$H NMR (DMSO-$d_6$) δ: 4.57 (2H, s), 7.37-7.47 (2H, m), 7.54-7.65 (2H, m), 7.72-7.83 (5H, m), 8.39-8.41 (1H, m), 8.53-8.56 (1H, dd, J=1.6 Hz, 7.6 Hz)

Example 18

3-(3-Trifluoromethylbenzyl)-5-(3-trifluoromethylphenyl)-1H-pyrazolo[4,3-c][1,8]naphthyridin-4(5H)-one To a suspension of 4-hydroxy-1-(3-trifluoromethylphenyl)-3-(3-trifluoromethylphenylacetyl)-1,8-naphthyridin-2(1H)-one (740 mg, 1.5 mmol) produced in Synthesis Example 15 in DMF (5 mL) was added hydrazine monohydrate (purity of 80%, 291 μL), and the mixture was stirred at 100 to 110° C. for 1 hour. To the reaction solution was added a sodium hydrogencarbonate aqueous solution. The resulting precipitate was separated by filtration, recrystallized from ethanol, and dried to give 3-(3-trifluoromethylbenzyl)-5-(3-trifluoromethylphenyl)-1H-pyrazolo[4,3-c][1,8]naphthyridin-4(5H)-one (364 mg, yield 50%).

mp: 206-208° C./EtOH $^1$H NMR (DMSO-$d_6$) δ: 4.46 (2H, s), 7.36 (1H, dd, J=4.9 Hz, 7.6 Hz), 7.49-7.84 (8H, m), 8.37 (1H, d, J=4.3 Hz), 8.51 (1H, d, J=7.8 Hz)

Example 19

3-(4-Trifluoromethylbenzyl)-5-(3-trifluoromethylphenyl)-1H-pyrazolo[4,3-c][1,8]naphthyridin-4(5H)-one To a suspension of 4-hydroxy-1-(3-trifluoromethylphenyl)-3-(4-trifluoromethylphenylacetyl)-1,8-naphthyridin-2(1H)-one (985 mg, 2.0 mmol) produced in Synthesis Example 16 in DMF (10 mL) was added hydrazine monohydrate (purity of 80%, 388 μL), and the mixture was stirred at 100 to 110° C. for 2 hours. To the reaction solution was added a sodium hydrogencarbonate aqueous solution. The resulting precipitate was separated by filtration, recrystallized from ethanol, and dried to give 3-(4-trifluoromethylbenzyl)-5-(3- trifluoromethylphenyl)-1H-pyrazolo[4,3-c][1,8]naphthyridin-4(5H)-one (342 mg, yield 35%).

mp: 145-148° C./EtOH $^1$H NMR (DMSO-d$_6$) δ: 4.45 (2H, s), 7.34-7.38 (1H, m), 7.53-7.67 (5H, m), 7.73-7.84 (3H, m), 8.38 (1H, dd, J=1.6 Hz, 4.6 Hz), 8.52 (1H, dd, J=1.1 Hz, 7.8 Hz)

Example 20

3-(2-Trifluoromethoxybenzyl)-5-(3-trifluoromethylphenyl)-1H-pyrazolo[4,3-c][1,8]naphthyridin-4(5H)-one To a suspension of 4-hydroxy-3-(2-trifluoromethoxyphenylacetyl)-1-(3-trifluoromethylphenyl)-1,8-naphthyridin-2(1H)-one (1.01 g, 2.0 mmol) produced in Synthesis Example 17 in DMF (5 mL) was added hydrazine monohydrate (purity of 80%, 388 μL), and the mixture was stirred at 100 to 110° C. for 1 hour. To the reaction solution was added a sodium hydrogencarbonate aqueous solution. The resulting precipitate was separated by filtration, recrystallized from ethanol, and dried to give 3-(2-trifluoromethoxybenzyl)-5-(3-trifluoromethylphenyl)-1H-pyrazolo[4,3-c][1,8]naphthyridin-4(5H)-one (516 mg, yield 51%).

mp: 247-252° C./EtOH $^1$H NMR (DMSO-d$_6$) δ: 4.43 (2H, s), 7.31-7.40 (5H, m), 7.61-7.63 (1H, d, J=7.6 Hz), 7.73-7.83 (3H, m), 8.39 (1H, d, J=3.8 Hz), 8.53 (1H, dd, J=1.6 Hz, 7.8 Hz)

Example 21

3-(3-Trifluoromethoxybenzyl)-5-(3-trifluoromethylphenyl)-1H-pyrazolo[4,3-c][1,8]naphthyridin-4(5H)-one To a suspension of 4-hydroxy-3-(3-trifluoromethoxyphenylacetyl)-1-(3-trifluoromethylphenyl)-1,8-naphthyridin-2(1H)-one (477 mg, 0.94 mmol) produced in Synthesis Example 18 in DMF (5 mL) was added hydrazine monohydrate (purity of 80%, 184 μL), and the mixture was stirred at 100 to 110° C. for 1 hour. To the reaction solution was added a sodium hydrogencarbonate aqueous solution. The resulting precipitate was separated by filtration, recrystallized from ethanol, and dried to give 3-(3-trifluoromethoxybenzyl)-5-(3-trifluoromethylphenyl)-1H-pyrazolo[4,3-c][1,8]naphthyridin-4(5H)-one (241 mg, yield 51%).

mp: 129-132° C./EtOH $^1$H NMR (DMSO-d$_6$) δ: 4.41 (2H, s), 7.18 (1H, d, J=7.6 Hz), 7.34-7.45 (4H, m), 7.63 (1H, d, J=7.6 Hz), 7.73-7.84 (3H, m), 8.37-8.52 (2H, m), 14.21 (1H, br)

Example 22

3-(4-Trifluoromethoxybenzyl)-5-(3-trifluoromethylphenyl)-1H-pyrazolo[4,3-c][1,8]naphthyridin-4(5H)-one To a suspension of 4-hydroxy-3-(4-trifluoromethoxyphenylacetyl)-1-(3-trifluoromethylphenyl)-1,8-naphthyridin-2(1H)-one (307 mg, 0.60 mmol) produced in Synthesis Example 19 in DMF (5 mL) was added hydrazine monohydrate (purity of 80%, 120 μL), and the mixture was stirred at 100 to 110° C. for 2 hours. To the reaction solution was added a sodium hydrogencarbonate aqueous solution. The resulting precipitate was separated by filtration, recrystallized from ethanol, and dried to give 3-(4-trifluoromethoxybenzyl)-5-(3-trifluoromethylphenyl)-1H-pyrazolo[4,3-c][1,8]naphthyridin-4(5H)-one (190 mg, yield 63%).

mp: 134-137° C./EtOH $^1$H NMR (DMSO-d$_6$) δ: 4.39 (2H, s), 7.27-7.47 (5H, m), 7.63-7.84 (4H, m), 8.37 (1H, dd, J=1.9 Hz, 4.9 Hz), 8.51 (1H, dd, J=1.6 Hz, 7.6 Hz)

Example 23

5-(3-Trifluoromethoxyphenyl)-3-(2-trifluoromethylbenzyl)-1H-pyrazolo[4,3-c][1,8]naphthyridin-4(5H)-one To a suspension of 4-hydroxy-1-(3-trifluoromethoxyphenyl)-3-(2-trifluoromethylphenylacetyl)-1,8-naphthyridin-2(1H)-one (763 mg, 1.5 mmol) produced in Synthesis Example 20 in DMF (5 mL) was added hydrazine monohydrate (purity of 80%, 291 μL), and the mixture was stirred at 100 to 110° C. for 1 hour. To the reaction solution was added a sodium hydrogencarbonate aqueous solution. The resulting precipitate was separated by filtration, recrystallized from ethanol, and dried to give 5-(3-trifluoromethoxyphenyl)-3-(2-trifluoromethylbenzyl)-1H-pyrazolo[4,3-c][1,8]naphthyridin-4(5H)-one (520 mg, yield 69%).

mp: 252-255° C./EtOH $^1$H NMR (DMSO-d$_6$) δ: 4.57 (2H, s), 7.26 (1H, m), 7.34-7.47 (5H, m), 7.57 (1H, t, J=7.3 Hz), 7.64 (1H, t, J=8.1 Hz), 7.74 (1H, d, J=7.0 Hz), 8.41 (1H, dd, J=1.6 Hz, 4.6 Hz), 8.53 (1H, dd, J=1.9 Hz, 7.8 Hz)

Example 24

5-(3-Trifluoromethoxyphenyl)-3-(3-trifluoromethylbenzyl)-1H-pyrazolo[4,3-c][1,8]naphthyridin-4(5H)-one To a suspension of 4-hydroxy-1-(3-trifluoromethoxyphenyl)-3-(3-trifluoromethylphenylacetyl)-1,8-naphthyridin-2(1H)-one (254 mg, 0.50 mmol) produced in Synthesis Example 21 in DMF (5 mL) was added hydrazine monohydrate (purity of 80%, 97 μL), and the mixture was stirred at 100 to 110° C. for 1 hour. To the reaction solution was added a sodium hydrogencarbonate aqueous solution. The resulting precipitate was separated by filtration, recrystallized from ethanol, and dried to give 5-(3-trifluoromethoxyphenyl)-3-(3-trifluoromethylbenzyl)-1H-pyrazolo[4,3-c][1,8]naphthyridin-4(5H)-one (12 mg, yield 4.8%).

mp: 206-209° C./EtOH $^1$H NMR (DMSO-d$_6$) δ: 4.46 (2H, s), 7.34-7.71 (9H, m), 8.39 (1H, m), 8.50 (1H, m)

Example 25

5-(3-Trifluoromethoxyphenyl)-3-(4-trifluoromethylbenzyl)-1H-pyrazolo[4,3-c][1,8]naphthyridin-4(5H)-one To a suspension of 4-hydroxy-1-(3-trifluoromethoxyphenyl)-3-(4-trifluoromethylphenylacetyl)-1,8-naphthyridine-2(1H)-one (508 mg, 1.0 mmol) produced in Synthesis Example 22 in DMF (8 mL) was added hydrazine monohydrate (purity of 80%, 194 μL), and the mixture was stirred at 100 to 110° C. for 2 hours. To the reaction solution was added a sodium hydrogencarbonate aqueous solution. The resulting precipitate was separated by filtration, recrystallized from ethanol, and dried to give 5-(3-trifluoromethoxyphenyl)-3-

(4-trifluoromethylbenzyl)-1H-pyrazolo[4,3-c][1,8]naphthyridin-4(5H)-one (162 mg, yield 32%).

mp: 227-231° C./EtOH $^1$H NMR (DMSO-d$_6$) δ: 4.45 (2H, s), 7.33-7.47 (4H, m), 7.53-7.67 (5H, m), 8.38 (1H, dd, J=1.6 Hz, 4.6 Hz), 8.51 (1H, dd, J=1.6 Hz, 7.6 Hz)

Example 26

3-(2-Trifluoromethoxybenzyl)-5-(3-trifluoromethoxyphenyl)-1H-pyrazolo[4,3-c][1,8]naphthyridin-4(5H)-one To a suspension of 4-hydroxy-1-(3-trifluoromethoxyphenyl)-3-(2-trifluoromethoxyphenylacetyl)-1,8-naphthyridin-2(1H)-one (420 mg, 0.80 mmol) produced in Synthesis Example 23 in DMF (5 mL) was added hydrazine monohydrate (purity of 80%, 155 µL), and the mixture was stirred at 100 to 110° C. for 1 hour. To the reaction solution was added a sodium hydrogencarbonate aqueous solution. The resulting precipitate was separated by filtration, recrystallized from ethanol, and dried to give 3-(2-trifluoromethoxybenzyl)-5-(3-trifluoromethoxyphenyl)-1H-pyrazolo[4,3-c][1,8]naphthyridin-4(5H)-one (233 mg, yield 56%).

mp: 233-236° C./EtOH $^1$H NMR (DMSO-d$_6$) δ: 4.43 (2H, s), 7.33-7.47 (8H, m), 7.65 (1H, t, J=8.1 Hz), 8.39 (1H, m), 8.52 (1H, dd, J=1.1 Hz, 7.6 Hz), 14.17 (1H, br)

Example 27

3-(3-Trifluoromethoxybenzyl)-5-(3-trifluoromethoxyphenyl)-1H-pyrazolo[4,3-c][1,8]naphthyridin-4(5H)-one To a suspension of 4-hydroxy-1-(3-trifluoromethoxyphenyl)-3-(3-trifluoromethoxyphenylacetyl)-1,8-naphthyridin-2(1H)-one (630 mg, 1.2 mmol) produced in Synthesis Example 24 in DMF (5 mL) was added hydrazine monohydrate (purity of 80%, 233 µL), and the mixture was stirred at 100 to 110° C. for 1 hour. To the reaction solution was added a sodium hydrogencarbonate aqueous solution. The resulting precipitate was separated by filtration, recrystallized from ethanol, and dried to give 3-(3-trifluoromethoxybenzyl)-5-(3-trifluoromethoxyphenyl)-1H-pyrazolo[4,3-c][1,8]naphthyridin-4(5H)-one (101 mg, yield 16%).

mp: 174-177° C./EtOH $^1$H NMR (DMSO-d$_6$) δ: 4.41 (2H, s), 7.16-7.20 (1H, m), 7.34-7.47 (7H, m), 7.65 (1H, t, J=8.1 Hz), 8.39 (1H, m), 8.50 (1H, m), 14-15 (1H, br)

Example 28

3-(4-Trifluoromethoxybenzyl)-5-(3-trifluoromethoxyphenyl)-1H-pyrazolo[4,3-c][1,8]naphthyridin-4(5H)-one To a suspension of 4-hydroxy-1-(3-trifluoromethoxyphenyl)-3-(4-trifluoromethoxyphenylacetyl)-1,8-naphthyridin-2(1H)-one (524 mg, 1.0 mmol) produced in Synthesis Example 25 in DMF (5 mL) was added hydrazine monohydrate (purity of 80%, 194 µL), and the mixture was stirred at 100 to 110° C. for 2 hours. To the reaction solution was added a sodium hydrogencarbonate aqueous solution. The resulting precipitate was separated by filtration, recrystallized from ethanol, and dried to give 3-(4-trifluoromethoxybenzyl)-5-(3-trifluoromethoxyphenyl)-1H-pyrazolo[4,3-c][1,8]naphthyridin-4(5H)-one (301 mg, yield 58%).

mp: 129-132° C./EtOH $^1$H NMR (DMSO-d$_6$) δ: 4.39 (2H, s), 7.26-7.47 (8H, m), 7.65 (1H, t, J=7.8 Hz), 8.36-8.38 (1H, m), 8.48-8.52 (1H, dd, J=1.1 Hz, 7.6 Hz)

Example 29

3-Benzyl-5-phenyl-1H-pyrazolo[4,3-c][1,7]naphthyridin-4(5H)-one

To a suspension of 4-hydroxy-1-phenyl-3-phenylacetyl-1,7-naphthyridin-2(1H)-one (100 mg, 0.28 mmol) produced in Synthesis Example 26 in DMF (3 mL) was added hydrazine monohydrate (purity of 80%, 68 µL), and the mixture was stirred at 100 to 110° C. for 2 hours. To the reaction solution was added a sodium hydrogencarbonate aqueous solution. The resulting precipitate was separated by filtration, recrystallized from ethanol, and dried to give 3-benzyl-5-phenyl-1H-pyrazolo[4,3-c][1,7]naphthyridin-4(5H)-one (78 mg, 79%).

mp: 303-307° C./MeOH $^1$H NMR (DMSO-d$_6$) δ: 4.38 (2H, s), 7.18-7.43 (7H, m), 7.58-7.67 (3H, m), 7.80 (1H, s), 8.04 (1H, d, J=4.6 Hz), 8.42 (1H, d, J=5.4 Hz), 14.32 (1H, brs)

Example 30

3-Benzyl-5-phenyl-1H-pyrazolo[4,3-c][1,5]naphthyridin-4(5H)-one

In accordance with a process described in JP-61-246183A or J. Med. Chem., 31, 2108 (1988), 4-hydroxy-1-phenyl-1,5-naphthyridin-2(1H)-one was synthesized. To a solution of the synthesized compound (477 mg, 2.0 mmol) in DMF (16 mL) was added sodium hydride (purity of about 60%, 176 mg, 4.4 mmol, 2.2 eq.), and the mixture was stirred until no more hydrogen was generated. The suspended mixture was heated at 40° C., and phenylacetyl chloride (0.31 mL, 2.3 mmol, 1.2 eq.) was added thereto, and the mixture was stirred at a room temperature for 2 hours. To the resulting mixture were added dichloromethane and water, and the organic layer was separated. The organic layer was washed with a sodium hydrogencarbonate aqueous solution, water, and a saturated sodium chloride aqueous solution. The organic layer was dried over anhydrous magnesium sulfate, and the solvent was distilled off to give a residue.

The resulting residue was dissolved in DMF (5 mL), and hydrazine monohydrate (purity of 80%, 250 µL) was added thereto while cooling with ice. The reaction suspension was stirred at a room temperature for 30 minutes, and then stirred at 100 to 110° C. for 1 hour. The insoluble residue was filtered by hot filtration, and the filtrate was washed with hexane. Then, to the filtrate was added a sodium hydrogencarbonate aqueous solution. The resulting precipitate was separated by filtration, washed with water, and dried to give 3-benzyl-5-phenyl-1H-pyrazolo[4,3-c][1,5]naphthyridin-4(5H)-one as a form of crystal (111 mg, 16%).

mp: 269-272° C./DMF-H$_2$O $^1$H NMR (DMSO-d$_6$) δ: 4.33 (2H, s), 6.91 (1H, dd, J=1.0 Hz, 8.6 Hz), 7.13-7.40 (7H, m), 7.43 (1H, dd, J=4.3 Hz, 8.6 Hz), 7.51-7.67 (3H, m), 8.50 (1H, dd, J=1.0 Hz, 4.3 Hz)

Example 31

3-(2-Methoxybenzyl)-5-(3-trifluoromethoxyphenyl)-1H-pyrazolo[4,3-c][1,8]-naphthyridin-4(5H)-one To a suspension of 4-hydroxy-3-(2-methoxyphenylacetyl)-1-(3-trifluoromethoxyphenyl)-1,8-naphthyridin-2 (1H)-one (840 mg, 1.8 mmol) produced in Synthesis Example 27 in DMF (7 mL) was added hydrazine monohydrate (purity of 80%, 285 µL), and the mixture was stirred at 110 to 120° C. for 2 hours. To the reaction solution was added a sodium hydrogencarbonate aqueous solution. The resulting precipitate was separated by filtration, washed with water, and dried to give 3-(2-methoxybenzyl)-5-(3-trifluoromethoxyphenyl)-1H-pyrazolo[4,3-c][1,8]-naphthyridin-4 (5H)-one as a form of crystal (770 mg, yield 92%).

mp: 243-245° C./DMF-$H_2O$ $^1$H NMR (DMSO-$d_6$) δ: 3.80 (3H, s), 4.31 (2H, s), 6.82 (1H, dt, J=1.0 Hz, 7.3 Hz), 6.97 (1H, d, J=7.6 Hz), 7.02 (1H, dd, J=1.6 Hz, 7.3 Hz), 7.20 (1H, dt, J=1.6 Hz, 7.9 Hz), 7.31-7.39 (3H, m), 7.42-7.47 (1H, m), 7.63 (1H, t, J=7.9 Hz), 8.36 (1H, dd, J=1.6 Hz, 4.6 Hz), 8.51 (1H, dd, J=1.6 Hz, 7.6 Hz)

Example 32

3-(4-Fluorobenzyl)-5-(3-trifluoromethoxyphenyl)-1H-pyrazolo[4,3-c][1,8]-naphthyridin-4(5H)-one To a suspension of 3-(4-fluorophenylacetyl)-4-hydroxy-1-(3-trifluoromethoxyphenyl)-1,8-naphthyridin-2(1H)-one (229 mg, 0.5 mmol) produced in Synthesis Example 28 in DMF (4 mL) was added hydrazine monohydrate (purity of 80%, 80 µL), and the mixture was stirred at 110 to 120° C. for 3 hours. To the reaction solution was added a sodium hydrogencarbonate aqueous solution. The resulting precipitate was separated by filtration, washed with water, and dried to give 3-(4-fluorobenzyl)-5-(3-trifluoromethoxyphenyl)-1H-pyrazolo[4,3-c][1,8]-naphthyridin-4(5H)-one as a form of crystal (203 mg, yield 89%).

mp: 226-228° C./DMF-$H_2O$ $^1$H NMR (DMSO-$d_6$) δ: 4.34 (2H, s), 7.10 (2H, app-tt, 8.9 Hz, 2.3 Hz), 7.32-7.41 (5H, m), 7.44-7.48 (1H, m), 7.65 (1H, t, J=7.9 Hz), 8.37 (1H, dd, J=2.0 Hz, 4.6 Hz), 8.50 (1H, dd, J=2.0 Hz, 7.9 Hz)

Example 33

3-(2-Chlorobenzyl)-5-(3-trifluoromethoxyphenyl)-1H-pyrazolo[4,3-c][1,8]-naphthyridin-4(5H)-one To a suspension of 3-(2-chlorophenylacetyl)-4-hydroxy-1-(3-trifluoromethoxyphenyl)-1,8-naphthyridine-2(1H)-one (622 mg, 1.3 mmol) produced in Synthesis Example 29 in DMF (6 mL) was added hydrazine monohydrate (purity of 80%, 210 µL), and the mixture was stirred at 110 to 120° C. for 3 hours. To the reaction solution was added a sodium hydrogencarbonate aqueous solution. The resulting precipitate was separated by filtration, washed with water, and dried to give 3-(2-chlorobenzyl)-5-(3-trifluoromethoxyphenyl)-1H-pyrazolo[4,3-c][1,8]-naphthyridin-4(5H)-one as a form of crystal (579 mg, yield 94%).

mp: 273-275° C./DMF-$H_2O$ $^1$H NMR (DMSO-$d_6$) δ: 4.47 (2H, s), 7.20-7.30 (3H, m), 7.33-7.48 (5H, m), 7.64 (1H, t, J=7.9 Hz), 8.39 (1H, dd, J=1.6 Hz, 4.6 Hz), 8.53 (1H, dd, J=1.6 Hz, 7.9 Hz)

Example 34

3-(2-Methylbenzyl)-5-(3-trifluoromethoxyphenyl)-1H-pyrazolo[4,3-c][1,8]-naphthyridin-4(5H)-one To a suspension of 4-hydroxy-3-(2-methylphenylacetyl)-1-(3-trifluoromethoxyphenyl)-1,8-naphthyridin-2(1H)-one (521 mg, 1.1 mmol) produced in Synthesis Example 30 in DMF (5 mL) was added hydrazine monohydrate (purity of 80%, 183 µL), and the mixture was stirred at 110 to 120° C. for 2 hours. To the reaction solution was added a sodium hydrogencarbonate aqueous solution. The resulting precipitate was separated by filtration, washed with water, and dried to give 3-(2-methylbenzyl)-5-(3-trifluoromethoxyphenyl)-1H-pyrazolo[4,3-c][1,8]-naphthyridin-4(5H)-one as a form of crystal (496 mg, yield 96%).

mp: 240-242° C./DMF-$H_2O$ $^1$H NMR (DMSO-$d_6$) δ: 2.36 (3H, s), 4.35 (2H, s), 7.04-7.18 (4H, m), 7.33-7.37 (2H, m), 7.40 (1H, brs), 7.45 (1H, app-quin. d, J=1.0 Hz, 8.6 Hz), 7.64 (1H, t, J=8.2 Hz), 8.37 (1H, dd, J=2.0 Hz, 4.6 Hz), 8.52 (1H, dd, J=2.0 Hz, 7.9 Hz)

Example 35

3-(2-Nitrobenzyl)-5-(3-trifluoromethoxyphenyl)-1H-pyrazolo[4,3-c][1,8]-naphthyridin-4(5H)-one To a suspension of 4-hydroxy-3-(2-nitrophenylacetyl)-1-(3-trifluoromethoxyphenyl)-1,8-naphthyridin-2(1H)-one (450 mg, 0.93 mmol) produced in Synthesis Example 31 in DMF (4 mL) was added hydrazine monohydrate (purity of 80%, 148 µL), and the mixture was stirred at 110 to 120° C. for 3 hours. To the reaction solution was added a sodium hydrogencarbonate aqueous solution. The resulting precipitate was separated by filtration, washed with water, and dried to give 3-(2-nitrobenzyl)-5-(3-trifluoromethoxyphenyl)-1H-pyrazolo[4,3-c][1,8]-naphthyridin-4(5H)-one as a form of crystal (373 mg, yield 84%).

mp: 274-276° C./DMF-$H_2O$ $^1$H NMR (DMSO-$d_6$) δ: 4.69 (2H, s), 7.33-7.40 (3H, m), 7.44-7.55 (3H, m), 7.62-7.68 (2H, m), 8.00 (1H, dd, J=1.3 Hz, 8.2 Hz), 7.40 (1H, dd, J=2.0 Hz, 4.6 Hz), 8.49 (1H, dd, J=2.0 Hz, 7.9 Hz), 13-15 (1H, br)

Example 36

3-(1-Phenylethyl)-5-(3-trifluoromethoxyphenyl)-1H-pyrazolo[4,3-c][1,8]naphthyridin-4(5H)-one To a suspension of 4-hydroxy-3-(2-phenylpropionyl)-1-(3-trifluoromethoxyphenyl)-1,8-naphthyridin-2(1H)-one (276 mg, 0.61 mmol) produced in Synthesis Example 32 in DMF (3 mL) was added hydrazine monohydrate (purity of 80%, 100 µL), and the mixture was stirred at 110 to 120° C. for 2 hours. To the reaction solution was added a sodium hydrogencarbonate aqueous solution, and an oily substance was collected. To the oily substance was added isopropyl ether, and the mixture was heated. Then the resulting matter was allowed to stand to a room temperature for crystallization. The resulting crystal was separated by filtration and dried to give 3-(1-phenylethyl)-5-(3-trifluoromethoxyphenyl)-1H-pyrazolo[4,3-c][1,8]naphthyridin-4(5H)-one as a form of crystal (140 mg, yield 51%).

mp: 183-185° C./i-$Pr_2O$ $^1$H NMR (DMSO-$d_6$) δ: 1.71 (3H, d, J=7.3 Hz), 4.95 (1H, q, J=7.6 Hz), 7.16 (1H, app-tt, J=7.3 Hz, 1.3 Hz), 7.23-7.38

(7H, m), 7.45 (1H, app-quin. d, J=1.0 Hz, 8.6 Hz), 7.63 (1H, t, J=7.9 Hz), 8.35 (1H, dd, J=2.0 Hz, 4.6 Hz), 8.51 (1H, dd, J=2.0 Hz, 7.9 Hz)

Example 37

3-(2-Methoxybenzyl)-5-(3-trifluoromethylphenyl)-1H-pyrazolo[4,3-c][1,8]-naphthyridin-4(5H)-one To a suspension of 4-hydroxy-3-(2-methoxyphenylacetyl)-1-(3-trifluoromethylphenyl)-1,8-naphthyridin-2(1H)-one (493 mg, 1.1 mmol) produced in Synthesis Example 33 in DMF (4.5 mL) was added hydrazine monohydrate (purity of 80%, 175 μL), and the mixture was stirred at 110 to 120° C. for 2 hours. To the reaction solution was added a sodium hydrogencarbonate aqueous solution. The resulting precipitate was separated by filtration, washed with water, and dried to give 3-(2-methoxybenzyl)-5-(3-trifluoromethylphenyl)-1H-pyrazolo[4,3-c][1,8]-naphthyridin-4(5H)-one as a form of crystal (418 mg, yield 86%).

mp: 229-231° C./DMF-H$_2$O $^1$H NMR (DMSO-d$_6$) δ: 3.81 (3H, s), 4.32 (2H, s), 6.82 (1H, dt, J=1.0 Hz, 7.6 Hz), 6.97 (1H, dd, J=1.0 Hz, 8.2 Hz), 7.02 (1H, dd, J=1.6 Hz, 7.6 Hz), 7.20 (1H, dt, J=2.0 Hz, 8.2 Hz), 7.34 (1H, dd, J=4.6 Hz, 7.6 Hz), 7.60-7.64 (1H, m), 7.72-7.83 (3H, m), 8.35 (1H, dd, J=1.6 Hz, 4.6 Hz), 8.52 (1H, dd, J=1.6 Hz, 7.6 Hz)

Example 38

3-(4-Fluorobenzyl)-5-(3-trifluoromethylphenyl)-1H-pyrazolo[4,3-c][1,8]-naphthyridin-4(5H)-one To a suspension of 3-(4-fluorophenylacetyl)-4-hydroxy-1-(3-trifluoromethylphenyl)-1,8-naphthyridin-2(1H)-one (604 mg, 1.4 mmol) produced in Synthesis Example 34 in DMF (5.5 mL) was added hydrazine monohydrate (purity of 80%, 220 μL), and the mixture was stirred at 110 to 120° C. for 2 hours. To the reaction solution was added a sodium hydrogencarbonate aqueous solution. The resulting precipitate was separated by filtration, washed with water, and dried to give 3-(4-fluorobenzyl)-5-(3-trifluoromethylphenyl)-1H-pyrazolo[4,3-c][1,8]-naphthyridin-4(5H)-one as a form of crystal (536 mg, yield 90%).

mp: 243-245° C./DMF-H$_2$O $^1$H NMR (DMSO-d$_6$) δ: 4.34 (2H, s), 7.10 (2H, app-tt, J=8.9 Hz, 2.3 Hz), 7.32-7.40 (3H, m), 7.62-7.65 (1H, m), 7.73-7.84 (3H, m), 8.36 (1H, dd, J=2.0 Hz, 4.6 Hz), 8.51 (1H, dd, J=2.0 Hz, 7.9 Hz)

Example 39

3-(2-Chlorobenzyl)-5-(3-trifluoromethylphenyl)-1H-pyrazolo[4,3-c][1,8]-naphthyridin-4(5H)-one To a suspension of 3-(2-chlorophenylacetyl)-4-hydroxy-1-(3-trifluoromethylphenyl)-1,8-naphthyridin-2(1H)-one (687 mg, 1.5 mmol) produced in Synthesis Example 35 in DMF (6 mL) was added hydrazine monohydrate (purity of 80%, 240 μL), and the mixture was stirred at 110 to 120° C. for 2 hours. To the reaction solution was added a sodium hydrogencarbonate aqueous solution. The resulting precipitate was separated by filtration, washed with water, and dried to give 3-(2-chlorobenzyl)-5-(3-trifluoromethylphenyl)-1H-pyrazolo[4,3-c][1,8]-naphthyridin-4(5H)-one as a form of crystal (632 mg, yield 93%).

mp: 276-278° C./DMF-H$_2$O $^1$H NMR (DMSO-d$_6$) δ: 4.47 (2H, s), 7.20-7.30 (3H, m), 7.37 (1H, dd, J=4.6 Hz, 7.9 Hz), 7.42-7.48 (1H, m), 7.62-7.65 (1H, m), 7.72-7.83 (3H, m), 8.39 (1H, dd, J=2.0 Hz, 4.6 Hz), 8.54 (1H, dd, J=2.0 Hz, 7.9 Hz), 13-15 (1H, br)

Example 40

3-(2-Methylbenzyl)-5-(3-trifluoromethylphenyl)-1H-pyrazolo[4,3-c][1,8]-naphthyridin-4(5H)-one To a suspension of 4-hydroxy-3-(2-methylphenylacetyl)-1-(3-trifluoromethylphenyl)-1,8-naphthyridin-2(1H)-one (568 mg, 1.3 mmol) produced in Synthesis Example 36 in DMF (5.5 mL) was added hydrazine monohydrate (purity of 80%, 207 μL), and the mixture was stirred at 110 to 120° C. for 2 hours. To the reaction solution was added a sodium hydrogencarbonate aqueous solution. The resulting precipitate was separated by filtration, washed with water, and dried to give 3-(2-methylbenzyl)-5-(3-trifluoromethylphenyl)-1H-pyrazolo[4,3-c][1,8]-naphthyridin-4(5H)-one as a form of crystal (519 mg, yield 92%).

mp: 249-252° C./DMF-H$_2$O $^1$H NMR (DMSO-d$_6$) δ: 2.36 (3H, s), 4.35 (2H, s), 7.04-7.18 (4H, m), 7.36 (1H, dd, J=4.6 Hz, 7.9 Hz), 7.62-7.65 (1H, m), 7.72-7.83 (3H, m), 8.37 (1H, dd, J=2.0 Hz, 4.6 Hz), 8.53 (1H, dd, J=2.0 Hz, 7.9 Hz)

Example 41

3-(2-Nitrobenzyl)-5-(3-trifluoromethylphenyl)-1H-pyrazolo[4,3-c][1,8]-naphthyridin-4(5H)-one To a suspension of 4-hydroxy-3-(2-nitrophenylacetyl)-1-(3-trifluoromethylphenyl)-1,8-naphthyridin-2(1H)-one (619 mg, 1.3 mmol) produced in Synthesis Example 37 in DMF (6 mL) was added hydrazine monohydrate (purity of 80%, 233 μL), and the mixture was stirred at 110 to 120° C. for 2 hours. To the reaction solution was added a sodium hydrogencarbonate aqueous solution. The resulting precipitate was separated by filtration, washed with water, and dried to give 3-(2-nitrobenzyl)-5-(3-trifluoromethylphenyl)-1H-pyrazolo[4,3-c][1,8]-naphthyridin-4(5H)-one as a form of crystal (565 mg, yield 92%).

mp: 282-284° C./DMF-H$_2$O $^1$H NMR (DMSO-d$_6$) δ: 4.69 (2H, s), 7.38 (1H, dd, J=4.6 Hz, 7.9 Hz), 7.46-7.55 (2H, m), 7.62-7.68 (2H, m), 7.73-7.85 (3H, m), 8.00 (1H, dd, J=1.3 Hz, 7.9 Hz), 8.39 (1H, dd, J=2.0 Hz, 4.6 Hz), 8.50 (1H, dd, J=2.0 Hz, 7.9 Hz)

Example 42

3-(1-Phenylethyl)-5-(3-trifluoromethylphenyl)-1H-pyrazolo[4,3-c][1,8]naphthyridin-4(5H)-one To a suspension of 4-hydroxy-3-(2-phenylpropionyl)-1-(3-trifluoromethylphenyl)-1,8-naphthyridin-2(1H)-one (119 mg, 0.27 mmol) produced in Synthesis Example 38 in DMF (1 mL) was added hydrazine monohydrate (purity of 80%, 43 μL), and the mixture was stirred at 110 to 120° C. for 2 hours. To the reaction solution was added a sodium hydrogencarbonate aqueous solution, and an oily substance was collected. To the oily substance was added isopropyl ether, and the mixture was heated. Then the resulting matter was allowed to stand to a room temperature for crystallization. The resulting crystal was separated by filtration and dried to give 3-(1- phenylethyl)-5-(3-trifluoromethylphenyl)-1H-pyrazolo[4,3-c][1,8]naphthyridin-4(5H)-one as a form of crystal (69 mg, yield 59%).

mp: 235-237° C./i-Pr$_2$O $^1$H NMR (DMSO-d$_6$) δ: 1.71 (3H, d, J=7.3 Hz), 4.95 (1H, q, J=7.3 Hz), 7.16 (1H, t, J=7.3 Hz), 7.24-7.38 (5H, m), 7.61 (1H, t, J=7.6 Hz), 7.74-7.83 (3H, m), 8.35 (1H, dd, J=1.6 Hz, 4.6 Hz), 8.52 (1H, dd, J=1.6 Hz, 7.6 Hz)

Example 43

5-Phenyl-3-(1-phenylpropyl)-1H-pyrazolo[4,3-c][1,8]naphthyridin-4(5H)-one

To a suspension of 4-hydroxy-1-phenyl-3-(2-phenylbutyryl)-1,8-naphthyridin-2(1H)-one (98 mg, 0.25 mmol) produced in Synthesis Example 39 in DMF (2 mL) was added hydrazine monohydrate (purity of 80%, 40 μL), and the mixture was stirred at 110 to 120° C. for 2 hours. To the reaction solution was added a sodium hydrogencarbonate aqueous solution. The resulting precipitate was separated by filtration and washed with water. The precipitate was recrystallized from ethanol and diisopropyl ether to give 5-phenyl-3-(1-phenylpropyl)-1H-pyrazolo[4,3-c][1,8]naphthyridin-4(5H)-one as a form of crystal (51 mg, yield 53%).

mp: 233-235° C./EtOH-i-Pr$_2$O $^1$H NMR (DMSO-d$_6$) δ: 0.85 (3H, t, J=7.3 Hz), 2.05-2.33 (2H, m), 4.70 (1H, t, J=7.9 Hz), 7.13-7.53 (11H, m), 8.33 (1H, dd, J=2.0 Hz, 4.6 Hz), 8.49 (1H, dd, J=2.0 Hz, 7.9 Hz)

Example 44

5-Phenyl-3-(tetrahydro-2H-pyran-4-ylmethyl)-1H-pyrazolo[4,3-c][1,8]naphthyridin-4(5H)-one To a suspension of 4-hydroxy-1-phenyl-3-(tetrahydro-2H-pyran-4-ylacetyl)-1,8-naphthyridin-2(1H)-one (120 mg, 0.33 mmol) produced in Synthesis Example 40 in DMF (2 mL) was added hydrazine monohydrate (purity of 80%, 53 μL), and the mixture was stirred at 110 to 120° C. for 2 hours. To the reaction solution was added a sodium hydrogen carbonate aqueous solution. The resulting precipitate was separated by filtration, washed with water, and dried to give 5-phenyl-3-(tetrahydro-2H-pyran-4-ylmethyl)-1H-pyrazolo[4,3-c][1,8]naphthyridin-4(5H)-one as a form of crystal (66 mg, yield 55%).

mp: 228-234° C./DMF-H$_2$O $^1$H NMR (CDCl$_3$) δ: 1.18-1.33 (2H, m), 1.47-1.53 (2H, m), 1.95-2.05 (1H, m), 2.93 (2H, d, J=7.3 Hz), 3.18-3.27 (2H, m), 3.78-3.83 (2H, m), 7.24-7.27 (2H, m), 7.31 (1H, dd, J=4.9 Hz, 7.9 Hz), 7.40-7.54 (3H, m), 8.34 (1H, dd, J=2.0 Hz, 4.6 Hz), 8.49 (1H, dd, J=2.0 Hz, 7.9 Hz)

Example 45

3-(2-Thienylmethyl)-5-(3-trifluoromethoxyphenyl)-1H-pyrazolo[4,3-c][1,8]-naphthyridin-4(5H)-one To a suspension of 4-hydroxy-3-(2-thienylacetyl)-1-(3-trifluoromethoxyphenyl)-1,8-naphthyridin-2(1H)-one (180 mg, 0.40 mmol) produced in Synthesis Example 41 in DMF (3 mL) was added hydrazine monohydrate (purity of 80%, 97 μL), and the mixture was stirred at 110 to 120° C. for 2 hours. To the reaction solution was added a sodium hydrogencarbonate aqueous solution. The resulting precipitate was separated by filtration, washed with water, recrystallized from methanol, and dried to give 3-(2-thienylmethyl)-5-(3-trifluoromethoxyphenyl)-1H-pyrazolo[4,3-c][1,8]-naphthyridin-4(5H)-one as a form of crystal (109 mg, yield 61%).

mp: 234-238° C./MeOH $^1$H NMR (DMSO-d$_6$) δ: 4.55 (2H, s), 6.90-6.95 (2H, m), 7.31-7.41 (5H, m), 7.65 (1H, t, J=8.4 Hz), 8.39 (1H, d, J=4.1 Hz), 8.49-8.53 (1H, m)

Example 46

3-(3-Thienylmethyl)-5-(3-trifluoromethoxyphenyl)-1H-pyrazolo[4,3-c][1,8]-naphthyridin-4(5H)-one To a suspension of 4-hydroxy-3-(3-thienylacetyl)-1-(3-trifluoromethoxyphenyl)-1,8-naphthyridin-2(1H)-one (80 mg, 0.18 mmol) produced in Synthesis Example 42 in DMF (3 mL) was added hydrazine monohydrate (purity of 80%, 44 μL), and the mixture was stirred at 110 to 120° C. for 2 hours. To the reaction solution was added a sodium hydrogencarbonate aqueous solution. The resulting precipitate was separated by filtration, washed with water, recrystallized from methanol, and dried to give 3-(3-thienylmethyl)-5-(3-trifluoromethoxyphenyl)-1H-pyrazolo[4,3-c][1,8]-naphthyridin-4(5H)-one as a form of crystal (47 mg, yield 60%).

mp: 247-251° C./MeOH $^1$H NMR (DMSO-d$_6$) δ: 4.35 (2H, s), 7.07 (1H, d, J=4.9 Hz), 7.23 (1H, s), 7.32-7.47 (5H, m), 7.65 (1H, t, J=8.4 Hz), 8.36-8.37 (1H, m), 8.49-8.51 (1H, m)

(3) Pharmacological Test Method and Test Results

Hereinafter, methods of results pharmacological tests concerning the validity and safety of the heterocycle compound or the salt thereof of the present invention will be illustrated and explained.

Test Example 1

PDE IV Inhibitory Action

A PDE IV activity was measured in accordance with Nicholson et al. [Br. J. Pharmacol., 97, 889 (1989)].

PDE IV isozyme separated from U937 cultured cell by an ion exchange chromatography was used. The PDE IV isozyme was added to ethylene glycol so that the final concentration of the isozyme was 30% by weight, and the solution was stored at −20° C. The stored solution was dissolved in use. The enzyme activity was measured by using cAMP as a substrate.

To an incubation buffer having the following formulation were added 25 μL (100,000 cpm) of [$^3$H]-cAMP (962 Bq/mmol; manufactured by Amarsham Bioscience) and 25 μL of PDE IV isozyme, and the total volume was adjusted to 250 μL (Solution A). On the other hand, the test compound was dissolved in dimethylsulfoxide (DMSO) so that the final concentration of the test compound was 1% by weight (2.5 μL/tube), and the resulting solution was named Solution B.

Formulation of the incubation buffer (pH 7.5): Tris-hydrochloric acid (50 mM), magnesium chloride (6 mM), dithiothreitol (2.5 mM), 5-nucleotidase (4 μg/mL), bovine serum albumin (0.23 mg/mL), and cAMP (1 μM)

A mixture of the Solution B of the test compound and the Solution A was incubated at 30° C. for 20 minutes. Then, 1 mL of a slurry of an anion exchange resin (AG1-X8, 200-400 mesh, chloride form; manufactured by Bio-Rad Laboratories, Inc.) was added thereto, and the reaction was stopped by adsorption of an unreacted substrate on the resin.

After the stop of the reaction, the reaction mixture was centrifuged at a centrifugal acceleration of 800×g for 10 minutes, and 250 μL of the resulting supernatant was transferred in a vial. To the vial was added 5 mL of ACS-II (a scintillator manufactured by Amarsham Bioscience), and a [$^3$H]-adenosine radio activity was measured as a PDE IV activity by a liquid scintillation counter.

A inhibition rate (%) of the PDE IV activity of the test compound relative to a control was calculated, and the value of the 50% inhibition concentration ($IC_{50}$) was determined based on Probit method. The results are shown in Table 1. Incidentally, as a control compound for this test, (−)-4-[3-(cyclopentyloxy)-4-methoxyphenyl]-2-pyrolizidinone (rolipram), which has been known as a PDE IV inhibitor, was used.

[Table 1]

TABLE 1

| Test compounds | PDE IV inhibitory action ($IC_{50}$; μM) |
| --- | --- |
| Example 1 | 0.003 |
| Example 2 | 0.007 |
| Example 8 | 0.003 |
| Example 11 | 0.014 |
| rolipram | 0.80 |

As apparent from the Table, it was proved that the example compounds of the present invention showed an excellent inhibitory activity to PDE IV.

Test Example 2

Inhibitory Action on Galactosamine- and LPS-Induced TNFα Production

A dose (0.5 mg/kg) of the test compound suspended in 0.5% (W/V) CMC-Na aqueous solution was orally administered to a mouse. After one hour, galactosamine (800 mg/kg) and LPS (5 μg/kg) were intravenously administered to induce TNFα production. The amount of TNFα in serum one hour after the administration of galactosamine and LPS was measured by ELISA method. The results are shown in Table 2.

[Table 2]

TABLE 2

| Test compounds | Inhibitory rate (%) of TNFα production in 0.5 mg/kg |
| --- | --- |
| Example 1 | 47 |
| Example 2 | 55 |
| Example 8 | 51 |
| Example 11 | 49 |
| Roflumilast | 50 |

As apparent from the Table, it was proved that all of example compounds and roflumilast had a high inhibitory action on TNFα production.

Test Example 3

Inhibitory Action on Drug Metabolizing Enzyme

Inhibitory actions on CYP2D6 and CYP3A4 were measured by using a CYP2D6/AMMC high throughput inhibitor screening kit and a CYP3A4/BFC high throughput inhibitor screening kit (both manufactured by BD Bioscience), respectively. That is, an NADPH generation system, a cofactor, and the test compound were dispersed in a 96-well plate, and AMMC (CYP2D6) and BFC (CYP3A4), which were fluorescent substrates, were added to each well. Further, CYP2D6 expression system microsome and CYP3A4 expression system microsome were added to each well and incubated at 37° C. for 30 minutes. Then, from a fluorescence measurement (CYP2D6: excitation wavelength 390 nm, fluorescence wavelength 460 nm, CYP3A4: excitation wavelength 409 nm, fluorescence wavelength 538 nm) for each well, enzyme inhibitory actions on CYP2D6 and CYP3A4 were determined and showed in Table 3. Incidentally, as a control substance of this test, roflumilast was used.

[Table 3]

TABLE 3

| | Inhibitory action on drug metabolizing enzyme ($IC_{50}$; μM) | |
| --- | --- | --- |
| Test compounds | CYP2D6 | CYP3A4 |
| Compound of Example 8 | >10 | >10 |
| Compound of Example 11 | >10 | 8.9 |
| Roflumilast | 9.1 | 0.98 |

As apparent from the Table, it was proved that the compounds of Example 8 and Example 11 had weaker inhibitory action on the drug metabolizing enzymes (CYP2D6 and CYP3A4).

Test Example 4

Toxicity Test

As the test compound, the compounds of Examples 1, 2, 8, and 11 of the present invention were orally administered to four groups, five mice per group, and the performance status observation and the measurement of the body-weight were conducted for one week. Incidentally, the test compound was suspended in 0.5% CMC-Na and orally administered at a dose of 300 mg/10 mL/kg forcibly.

In each compound, neither death nor significant inhibition of weight increase was observed. Moreover, concerning other characteristics, apparent abnormality was not observed.

(4) Preparation Examples

Preparation Example 1

Using the following formulation, a tablet was obtained in accordance with a known manner described in General Rules for Preparations of JP XIV.

Formulation example per tablet (total amount 150 mg):

| | |
| --- | --- |
| Compound of the present invention | 30 mg |
| Crystalline cellulose | 90 mg |
| Corn starch | 28 mg |
| Magnesium stearate | 2 mg |

Preparation Example 2

Using the following formulation, a capsule was obtained in accordance with a known manner described in General Rules for Preparations of JP XIV.

Formulation example per capsule (total amount 180 mg):

| Compound of the present invention | 50 mg |
|---|---|
| Lactose | 100 mg |
| Corn starch | 28 mg |
| Magnesium stearate | 2 mg |

Preparation Example 3

The compound of the present invention (10 mg) was dissolved in 3 mL of a physiological saline, and the solution was adjusted to pH 7 with a 0.1 N sodium hydroxide aqueous solution. Then, a physiological saline was further added thereto so that the total volume of the solution was 5 mL. The resulting solution was divided in ampoules, and the ampoules were heat-sterilized to give injectable solutions.

Preparation Example 4

To the compound of the present invention (1 g), yolk lecithin (1.2 g), α-tocopherol (20 mg), and ascorbic acid (33 mg) was added a purified water, and the total volume thereof was adjusted to 100 mL to prepare an aerosol preparation.

The invention claimed is:

1. A compound represented by the following formula (1):

wherein the ring A represents a 6-membered heterocycle containing a nitrogen atom as a heteroatom;
the ring B represents a benzene ring;
—$R^6$— represents a direct bond,
the ring C is an aromatic or nonaromatic ring and represents a heterocycle represented by the following formula (1c-1) or (1c-2):

wherein each of $R^4$ and $R^5$ represents a hydrogen atom;
each of —$R^{6a}$— and —$R^{6b}$— corresponds to the —$R^6$—,
the —$R^{6a}$— represents a direct bond,
the —$R^{6b}$— represents a direct bond,
r is 1,
s is 1;
the ring D represents a nitrogen atom-containing unsaturated 6-membered ring having an oxo group at 2-position;
$R^1$ represents an alkyl group comprising a substituent represented by the following formula (1e):

$$-\!\!\!\fbox{E}\!\!\!-(R^7)_t \qquad (1e)$$

wherein the ring E represents a heterocycle containing at least one heteroatom selected from the group consisting of a nitrogen atom, an oxygen atom, and a sulfur atom, or a carbocycle;
$R^7$ represents a substituent selected from the group consisting of a halogen atom, a hydroxyl group, a cyano group, a nitro group, an alkyl group, a halogencontaining alkyl group, an alkoxy group, a halogen-containing alkoxy group, a carboxyl group, an alkoxycarbonyl group, an acyl group, an acyloxy group, a carboxyalkyl group, an alkoxycarbonylalkyl group, an amino group, an N-substituted amino group, a ureido group, a sulfonic acid group, a sulfinic acid group, an alkylsulfonyl group, and a sulfonamide group; and t denotes 0 or 1;
$R^2$ represents a methyl group;
$R^3$ represents a substituent selected from the group consisting of a halogen-containing alkyl group and a halogen-containing alkoxy group;
p and q are the same or different and each denotes 0 or 1;
when the group $R^1$ is a straight chain $C_{1-3}$alkyl group having a benzene ring, a thiophene ring, or a pyridine ring as the ring E, p is 0, and a fused ring comprising the ring A and the ring D is a fused ring represented by the following formula:

at least one of the ring B and the ring E has at least one member selected from the group consisting of a halogen-containing alkyl group and a halogen-containing alkoxy group as the substituent $R^3$ and/or $R^7$; and
$R^4$, $R^5$, —$R^6$—, r, s, and t have the same meanings as defined above; or a salt thereof.

2. The compound or salt thereof according to claim 1, wherein
in the formula (1e), the ring E is a cycloalkane ring or an arene ring, the group $R^7$ is a substituent selected from the group consisting of a halogen atom, an alkyl group, a halogen-containing alkyl group, an alkoxy group, and a halogen-containing alkoxy group.

3. The compound or salt thereof according to claim 1, wherein the group $R^1$ is a $C_{1-6}$alkyl group comprising a substituent represented by the formula (1e), and in the formula (1e), the ring E is a cycloalkane ring or an arene ring, the group $R^7$ is a substituent selected from the group consisting of a halogen atom, a $C_{1-6}$alkyl group, a halogen-containing $C_{1-6}$alkyl group, a $C_{1-6}$alkoxy group, and a halogen-containing $C_{1-6}$alkoxy group.

4. The compound or salt thereof according to claim 1, wherein at least one of the ring B and the ring E has at least one member selected from the group consisting of a fluoroalkyl group and a fluoroalkoxy group as the substituent $R^3$ and/or $R^7$.

5. The compound or salt thereof according to claim 1, wherein at least one of the ring B and the ring E has at least one member selected from the group consisting of a straight chain or branched chain fluoro$C_{1-6}$alkyl group and a straight chain or branched chain fluoro$C_{1-6}$alkoxy group as the substituent $R^3$ and/or $R^7$.

6. The compound or salt thereof according to claim 1, wherein
the ring A is any one of the rings represented by the following formulae

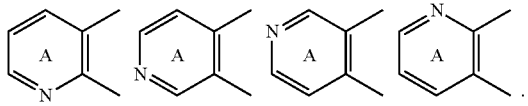

.

7. The compound or salt thereof according to claim 1, which is selected from the group consisting of
- a 3-($C_{1-4}$alkoxy-$C_{1-3}$alkyl)-5-phenyl-1H-pyrazolo[4,3-c][1,8]-naphthyridin-4(5H)-one,
- a 3-($C_{1-4}$alkoxy-$C_{1-3}$alkyl)-5-(fluoro$C_{1-4}$alkyl-phenyl)-1H-pyrazolo[4,3-c][1,8]-naphthyridin-4(5H)-one,
- a 3-($C_{1-4}$alkoxy-$C_{1-3}$alkyl)-5-(fluoro$C_{1-4}$alkoxy-phenyl)-1H-pyrazolo[4,3-c][1,8]-naphthyridin-4(5H)-one,
- a 3-$C_{4-10}$cycloalkyl-$C_{1-3}$alkyl-5-phenyl-1H-pyrazolo[4,3-c][1,8]-naphthyridin-4(5H)-one,
- a 3-($C_{4-10}$cycloalkyl-$C_{1-3}$alkyl)-5-(fluoro$C_{1-4}$alkyl-phenyl)-1H-pyrazolo[4,3-c][1,8]-naphthyridin-4(5H)-one,
- a 3-$C_{4-10}$cycloalkyl-$C_{1-3}$alkyl-5-(fluoro$C_{1-4}$alkoxy-phenyl)-1H-pyrazolo[4,3-c][1,8]-naphthyridin-4(5H)-one,
- a 3-(fluoro$C_{1-10}$alkyl)-5-phenyl-1H-pyrazolo[4,3-c][1,8]-naphthyridin-4(5H)-one,
- a 3-(fluoro$C_{1-10}$alkyl)-5-(fluoro$C_{1-4}$ alkyl-phenyl)-1H-pyrazolo[4,3-c][1,8]-naphthyridin-4(5H)-one,
- a 3-(fluoro$C_{1-10}$alkyl)-5-(fluoro$C_{1-4}$alkoxy-phenyl)-1H-pyrazolo[4,3-c][1,8]-naphthyridin-4(5H) -one,
- a 3-(phenyl-$C_{1-3}$alkyl)-5-(fluoro$C_{1-4}$alkyl-phenyl)-1H-pyrazolo[4,3-c][1,8]-naphthyridin-4(5H) -one,
- a 3-(phenyl-$C_{1-3}$alkyl)-5(fluoro$C_{1-4}$alkoxy-phenyl)-1H-pyrazolo[4,3 -c][1,8]-naphthyridin-4(5H) -one,
- a 3-(phenyl-branched $C_{2-4}$alkyl)-5-phenyl-1H-pyrazolo[4,3-c][1,8]-naphthyridin-4(5H)-one,
- a 3-(phenyl-branched $C_{2-4}$alkyl)-5-(fluoro$C_{1-4}$alkyl-phenyl)-1H-pyrazolo[4,3-c][1,8]-naphthyridin-4(5H)-one,
- a 3-(phenyl-branched $C_{2-4}$alkyl)-5-(fluoro$C_{1-4}$alkoxy-phenyl)-1H-pyrazolo[4,3-c][1,8]-naphthyridin-4(5H)-one,
- a 3-(phenyl-$C_{1-3}$alkyl)-5-phenyl-1H-pyrazolo[4,3-c][1,7]-naphthyridin-4(5H)-one,
- a 3-(phenyl-$C_{1-3}$alkyl)-5-phenyl-1H-pyrazolo[4,3-c][1,6]-naphthyridin-4(5H)-one,
- a 3-(phenyl-$C_{1-3}$alkyl)-5-phenyl-1H-pyrazolo[4,3-c][1,5]-naphthyridin-4(5H)-one,
- a 3-[(fluoro$C_{1-4}$alkyl-phenyl)$C_{1-3}$alkyl]-5-phenyl-1H-pyrazolo[4,3-c][1,8]-naphthyridin-4(5) -one,
- a 3-[(fluoro$C_{1-4}$alkyl-phenyl)$C_{1-3}$alkyl]-5-(fluoro$C_{1-4}$alkyl-phenyl)-1H-pyrazolo[4,3-c][1,8]-naphthyridin-4(5H)-one,
- a 3-[(fluoro$C_{1-4}$alkyl-phenyl)$C_{1-3}$alkyl]-5-(fluoro$C_{1-4}$alkoxy-phenyl)-1H-pyrazolo[4,3-c][1,8]-naphthyridin-4(5H)-one,
- a 3-[(fluoro$C_{1-4}$alkyl-phenyl) branched $C_{2-4}$alkyl]-5-phenyl-1H-pyrazolo[4,3-c][1,8]-naphthyridin-4(5H)-one,
- a 3-[(fluoro$C_{1-4}$alkyl-phenyl) branched $C_{2-4}$alkyl]-5-(fluoro$C_{1-4}$alkyl-phenyl)-1H-pyrazolo[4,3-c][1,8]-naphthyridin-4(5H)-one,
- a 3-[(fluoro$C_{1-4}$alkyl-phenyl) branched $C_{2-4}$alkyl]-5-(fluoro$C_{1-4}$alkoxy-phenyl)-1H-pyrazolo[4,3-c][1,8]-naphthyridin-4(5H)-one,
- a 3-[(fluoro$C_{1-4}$alkoxy-phenyl)$C_{1-3}$alkyl]-5-phenyl-1H-pyrazolo[4,3-c][1,8]-naphthyridin-4(5H)-one,
- a 3-[(fluoro$C_{1-4}$alkoxy-phenyl)$C_{1-3}$alkyl]-5-(fluoro$C_{1-4}$alkyl-phenyl)-1H-pyrazolo[4,3-c][1,8]naphthyridin-4(5H)-one,
- a 3-[(fluoro$C_{1-4}$alkoxy-phenyl)$C_{1-3}$alkyl]-5-(fluoro$C_{1-4}$alkoxy-phenyl)-1H-pyrazolo[4,3-c][1,8]naphthyridin-4(5H)-one,
- a 3-[(fluoro$C_{1-4}$alkoxy-phenyl) branched $C_{2-4}$alkyl]-5-phenyl-1H-pyrazolo[4,3-c][1,8]-naphthyridin-4(5H)-one,
- a 3-[(fluoro$C_{1-4}$alkoxy-phenyl) branched $C_{2-4}$alkyl]-5-(fluoro$C_{1-4}$alkyl-phenyl)-1H-pyrazolo[4,3-c][1,8]-naphthyridin-4(5H)-one,
- a 3-[(fluoro$C_{1-4}$alkoxy-phenyl) branched $C_{2-4}$alkyl]-5-(fluoro$C_{1-4}$alkoxy-phenyl)-1H-pyrazolo [4,3-c][1,8]-naphthyridin-4(5H)-one,
- a 3-($C_{1-4}$alkyl-phenyl-$C_{1-3}$alkyl)-5-(fluoro $C_{1-4}$alkyl-phenyl)- 1H-pyrazolo[4,3-c][1,8]-naphthyridin-4(5H)-one,
- a 3-($C_{1-4}$alkyl-phenyl-$C_{1-3}$alkyl)-5-(fluoro$C_{1-4}$alkoxy-phenyl)-1H-pyrazolo[4,3-c][1,8]-naphthyridin-4(5H)-one,
- a 3-(nitrophenyl-$C_{1-3}$alkyl)-5-(fluoro$C_{1-4}$-phenyl)-1H-pyrazolo[4,3-c][1,8]-naphthyridin-4(5H)-one,
- a 3-(nitrophenyl-$C_{1-3}$alkyl)-5-(fluoro$C_{1-4}$alkoxy-phenyl)-1H-pyrazolo[4,3-c][1,8]-naphthyridin-4(5H)-one,
- a 3-($C_{1-4}$alkoxy-phenyl-$C_{1-3}$alkyl)-5-(fluoro $C_{1-4}$alkyl-phenyl)- 1H-pyrazolo[4,3-c][1,8]-naphthyridin-4(5H)-one,
- a 3-($C_{1-4}$alkoxy-phenyl-$C_{1-3}$alkyl)-5 -(fluoro$C_{1-4}$alkoxy-phenyl)- 1H-pyrazolo[4,3-c][1,8]-naphthyridin-4(5H)-one,
- a 3-(halophenyl-$C_{1-3}$alkyl)-5-(fluoro$C_{1-4}$alkyl-phenyl)-1H-pyrazolo[4,3-c][1,8]-naphthyridin-4(5H)-one,
- a 3-(halophenyl-$C_{1-3}$alkyl)-5-(fluoro$C_{1-4}$alkoxy-phenyl)-1H-pyrazolo[4,3 -c][1,8]-naphthyridin4(5H)-one,
- a 5-phenyl-3-(tetrahydro-2H-pyran-4-yl$C_{1-3}$alkyl)-1H-pyrazolo[4,3-c][1,8]naphthyridin-4(5H)-one which may have a fluoro$C_{1-4}$alkyl group or a fluoro$C_{1-4}$alkoxy group at the phenyl group of 5-position,
- a 3-(thienyl$C_{1-3}$alkyl)-5-(fluoro$C_{1-4}$alkyl-phenyl)-1H-pyrazolo[4,3-c][1,8]-naphthyridin-4(5H)-one,
- a 3-(thienyl$C_{1-3}$alkyl)-5-(fluoro$C_{1-4}$alkoxy-phenyl)-1H-pyrazolo[4,3-c][1,8]-naphthyridin-4(5H)-one; and salts thereof.

8. A pharmaceutical composition containing a compound or a salt thereof recited in claim 1.

* * * * *